(12) United States Patent
Hyde et al.

(10) Patent No.: US 8,430,831 B2
(45) Date of Patent: Apr. 30, 2013

(54) DEVICE, SYSTEM, AND METHOD FOR CONTROLLABLY REDUCING INFLAMMATORY MEDIATORS IN A SUBJECT

(75) Inventors: Roderick A. Hyde, Redmond, WA (US); Muriel Y. Ishikawa, Livermore, CA (US); Edward K. Y. Jung, Bellevue, WA (US); Robert Langer, Newton, MA (US); Eric C. Leuthardt, St. Louis, MO (US); Nathan P. Myhrvold, Medina, WA (US); Elizabeth A. Sweeney, Seattle, WA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 486 days.

(21) Appl. No.: 12/380,399

(22) Filed: Feb. 25, 2009

(65) Prior Publication Data
US 2012/0109039 A1 May 3, 2012

Related U.S. Application Data

(63) Continuation-in-part of application No. 12/380,400, filed on Feb. 25, 2009.

(51) Int. Cl.
*A61M 37/00* (2006.01)
*A61M 31/00* (2006.01)
*C02F 1/44* (2006.01)
*C02F 1/00* (2006.01)
*B01D 39/00* (2006.01)

(52) U.S. Cl.
USPC ....... 604/4.01; 604/6.06; 604/6.09; 604/6.11; 604/507; 604/508; 210/645; 210/739; 210/502.1

(58) Field of Classification Search ............... 604/4.01, 604/5.01, 5.04, 6.09; 210/645, 501, 502.1, 210/745
See application file for complete search history.

(56) References Cited

U.S. PATENT DOCUMENTS
5,092,886 A 3/1992 Dobos-Hardy
5,281,199 A 1/1994 Ensminger et al.
(Continued)

FOREIGN PATENT DOCUMENTS
EP 1550454 A1 * 7/2005
WO WO 98/14243 A1 4/1998
WO WO 2004/000387 A2 12/2003
WO WO 2004/004707 A1 1/2004

OTHER PUBLICATIONS

Ng, David C. et al.; Real time in vivo imaging and measurement of serine protease activity in the mouse hippocampus using a dedicated complementary metal-oxide semiconductor imaging device'; Journal of Neuroscience Methods; 2006; pp. 23-30; vol. 156; Elsevier B.V.

(Continued)

*Primary Examiner* — Leslie Deak

(57) ABSTRACT

Devices, systems, and methods are provided for controlling an inflammatory response in a subject. Extracorporeal devices, systems, and methods are provided that alter the functional structure of one or more inflammatory mediators in the peripheral blood of the subject. The device or system is useful in a method for treating an inflammatory disease or condition in the subject.

38 Claims, 8 Drawing Sheets

U.S. PATENT DOCUMENTS

| | | |
|---|---|---|
| 5,470,570 A | 11/1995 | Taylor et al. |
| 5,702,432 A | 12/1997 | Chen et al. |
| 5,804,563 A | 9/1998 | Still et al. |
| 5,831,012 A | 11/1998 | Nilsson et al. |
| 5,843,440 A | 12/1998 | Pouletty et al. |
| 6,039,946 A | 3/2000 | Strahilevitz |
| 6,099,730 A | 8/2000 | Ameer et al. |
| 6,190,691 B1 | 2/2001 | Mak |
| 6,240,312 B1 | 5/2001 | Alfano et al. |
| 6,255,461 B1 | 7/2001 | Mosbach et al. |
| 6,287,516 B1 | 9/2001 | Matson et al. |
| 6,387,674 B1 | 5/2002 | Trasciatti et al. |
| 6,425,867 B1 | 7/2002 | Vaezy et al. |
| 6,670,427 B1 | 12/2003 | Ulbricht et al. |
| 6,673,596 B1 | 1/2004 | Sayler et al. |
| 6,733,471 B1 | 5/2004 | Ericson et al. |
| 6,797,522 B1 | 9/2004 | Still et al. |
| 6,881,408 B1 | 4/2005 | Heinrich et al. |
| 7,057,189 B2 | 6/2006 | Coogan |
| 7,097,662 B2 | 8/2006 | Evans, III et al. |
| 7,153,473 B2 | 12/2006 | Ericson et al. |
| 7,169,303 B2 | 1/2007 | Sullivan et al. |
| 7,201,730 B2 | 4/2007 | Davidner et al. |
| 7,207,964 B2 | 4/2007 | Davidner et al. |
| 7,244,232 B2 | 7/2007 | Connelly et al. |
| 7,282,358 B2 | 10/2007 | Coogan et al. |
| 7,291,122 B2 | 11/2007 | Matson |
| 7,303,875 B1 | 12/2007 | Bock et al. |
| 7,309,786 B2 | 12/2007 | Zhang et al. |
| 7,319,038 B2 | 1/2008 | Southard |
| 7,413,846 B2 | 8/2008 | Maloney et al. |
| 7,415,359 B2 | 8/2008 | Hill et al. |
| 7,892,766 B2 | 2/2011 | King et al. |
| 8,000,784 B2 | 8/2011 | Ferren et al. |
| 2002/0034757 A1 | 3/2002 | Cubicciotti |
| 2002/0141979 A1 | 10/2002 | Chen et al. |
| 2002/0177118 A1 | 11/2002 | Coogan, Jr. et al. |
| 2003/0130194 A1 | 7/2003 | Altrichter et al. |
| 2003/0215454 A1 | 11/2003 | Colb et al. |
| 2003/0231981 A1 | 12/2003 | Johnson et al. |
| 2004/0018508 A1 | 1/2004 | Friedman |
| 2004/0115612 A1 | 6/2004 | Coogan et al. |
| 2004/0121302 A1 | 6/2004 | Coogan |
| 2004/0182783 A1 | 9/2004 | Walker et al. |
| 2004/0186410 A1 | 9/2004 | Davidner et al. |
| 2004/0186411 A1 | 9/2004 | Mallett et al. |
| 2004/0186412 A1 | 9/2004 | Mallett et al. |
| 2004/0191246 A1 | 9/2004 | Connelly et al. |
| 2005/0249724 A1 | 11/2005 | Lihme et al. |
| 2005/0250716 A1 | 11/2005 | Schmidt et al. |
| 2005/0265996 A1 | 12/2005 | Lentz |
| 2005/0271653 A1 | 12/2005 | Strahilevitz |
| 2005/0272974 A1 | 12/2005 | Iddan |
| 2005/0288744 A1 | 12/2005 | Pilla et al. |
| 2006/0018912 A1 | 1/2006 | Finberg et al. |
| 2006/0025713 A1 | 2/2006 | Rosengart et al. |
| 2006/0047283 A1 | 3/2006 | Evans, III et al. |
| 2006/0057142 A1 | 3/2006 | Brady et al. |
| 2006/0083716 A1 | 4/2006 | Kaufman et al. |
| 2006/0147895 A1 | 7/2006 | Purdum |
| 2006/0183223 A1 | 8/2006 | King et al. |
| 2006/0234369 A1 | 10/2006 | Sih |
| 2006/0241040 A1 | 10/2006 | Visintin et al. |
| 2007/0010868 A1 | 1/2007 | Ferren et al. |
| 2007/0021458 A1 | 1/2007 | Ishikawa et al. |
| 2007/0021923 A1 | 1/2007 | Ishikawa et al. |
| 2007/0021927 A1 | 1/2007 | Ishikawa et al. |
| 2007/0066929 A1 | 3/2007 | Ferren et al. |
| 2007/0093739 A1 | 4/2007 | Brady et al. |
| 2007/0106281 A1 | 5/2007 | Hood et al. |
| 2007/0156211 A1 | 7/2007 | Ferren et al. |
| 2007/0178084 A1 | 8/2007 | King et al. |
| 2007/0203573 A1 | 8/2007 | Rudakov et al. |
| 2007/0225633 A1 | 9/2007 | Ferren et al. |
| 2007/0225634 A1 | 9/2007 | Ferren et al. |
| 2007/0244520 A1 | 10/2007 | Ferren et al. |
| 2007/0265787 A1 | 11/2007 | Bangera et al. |
| 2007/0265788 A1 | 11/2007 | Bangera et al. |
| 2007/0265818 A1 | 11/2007 | Bangera et al. |
| 2007/0265819 A1 | 11/2007 | Bangera et al. |
| 2007/0269489 A1 | 11/2007 | Humes |
| 2007/0276208 A1 | 11/2007 | Connelly et al. |
| 2007/0294150 A1 | 12/2007 | Jung et al. |
| 2008/0058785 A1 | 3/2008 | Boyden et al. |
| 2008/0058788 A1 | 3/2008 | Boyden et al. |
| 2008/0069738 A1 | 3/2008 | Ishikawa et al. |
| 2008/0103440 A1 | 5/2008 | Ferren et al. |
| 2008/0110830 A1 | 5/2008 | Matson |
| 2008/0154101 A1 | 6/2008 | Jain et al. |
| 2008/0201122 A1 | 8/2008 | Kelly et al. |
| 2008/0275376 A1 | 11/2008 | Howell et al. |
| 2009/0022768 A1 | 1/2009 | King et al. |
| 2010/0167372 A1 | 7/2010 | King et al. |

OTHER PUBLICATIONS

Alexander et al.; "Molecular imprinting science and technology: a survey of the literature for the years up to and including 2003"; Journal of Molecular Recognition; 2006; pp. 106-180; vol. 19; John Wiley & Sons, Ltd.

An, Gary; "Introduction of an agent-based multi-scale modular architecture for dynamic knowledge representation of acute inflammation"; Theoretical Biology and Medical Modelling; May 27, 2008; pp. 1-20; vol. 5, No. 11; BioMed Central Ltd.

Benson et al.; "GenBank"; Nucleic Acids Research; 2007, pp. D21-D25; vol. 35, Database issue.

Cao et al.; "Molecular Beacon Aptamers for Protein Monitoring in Real-Time and in Homogeneous Solutions"; Current Proteomics; 2005; pp. 31-40; vol. 2, No. 1; Bentham Science Publishers Ltd.

Charles et al.; "Investigating the Feasibility of Stem Cell Enrichment Mediated by Immobilized Selectins"; Biotechnol. Prog.; 2007; pp. 1463-1472; vol. 23, No. 6; American Chemical Society and American Institute of Chemical Engineers.

Chen et al.; "Ubiquitin-associated (UBA) domains in Rad23 bind ubiquitin and promote inhibition of multi-ubiquitin chain assembly"; EMBO reports; 2001; pp. 933-938; vol. 2, No. 10; European Molecular Biology Organization.

Colas et al.; "Targeted modification and transportation of cellular proteins"; PNAS; Dec. 5, 2000; pp. 13720-13725 (with attached correction page); vol. 97, No. 25.

Crawford et al.; "Peptide aptamers: Tools for biology and drug discovery"; Briefings in Functional Genomics and Proteomics; Apr. 2003; pp. 72-79; vol. 2, No. 1; Henry Stewart Publications.

Curtis et al.; "T-cell interleukin 1 receptor cDNA expressed in Chinese hamster ovary cells regulates functional responses to interleukin 1"; Proc. Natl. Acad. Sci. USA; May 1989; pp. 3045-3049; vol. 86.

Davies, Michael J.; "Singlet oxygen-mediated damage to proteins and its consequences"; BBRC; 2003; pp. 761-770; vol. 305; Elsevier Science (USA).

De Vriese et al.; "Cytokine Removal during Continuous Hemofiltration in Septic Patients"; J Am Soc Nephrol; 1999; pp. 846-853; vol. 10; American Society of Nephrology.

Dinarello, Charles A.; "Proinflammatory and Anti-inflammatory Cytokines as Mediators in the Pathogenesis of Septic Shock"; CHEST; Dec. 1997 Supplement; pp. 321S-329S; American College of Chest Physicians.

Durick et al.; "Cellular biosensors for drug discovery"; Biosensors & Bioelectronics; 2001; pp. 587-592; vol. 16; Elsevier Science B.V.

Economides et al.; "Cytokine traps: multi-component, high-affinity blockers of cytokine action"; Nature Medicine; Jan. 2003; pp. 47-52; vol. 9, No. 1; Nature Publishing Group.

Fan et al.; "Sensitive optical biosensors for unlabeled targets: A review"; Analytica Chimica Acta 620; 2008; pp. 8-26; Elsevier B.V.

Francisco et al.; "Production and fluorescence-activated cell sorting of *Escherichia coli* expressing a functional antibody fragment on the external surface"; Proc. Natl. Acad. Sci. USA; Nov. 1993; pp. 10444-10448; vol. 90.

Frangioni, John V.; "In vivo near-infrared fluorescence imaging"; Current Opinion in Chemical Biology; 2003; pp. 626-634; vol. 7; Elsevier Inc.

Fujii et al.; "Serum cytokine concentrations and acute graft-versus-host disease after allogeneic peripheral blood stem cell transplantation: Concurrent measurement of ten cytokines and their respective ratios using cytometric bead array"; International Journal of Molecular Medicine; 2006; pp. 881-885; vol. 17.
Guthrie et al.; "Assays for cytokines using aptamers"; METHODS; 2006; pp. 324-330; vol. 38; Elsevier Inc.
Heath et al.; "Antibody-targeted liposomes: Increase in specific toxicity of methotrexate-γ-aspartate"; Proc. Natl. Acad. Sci. USA; Mar. 1983; pp. 1377-1381; vol. 80.
Heeschen et al.; "Serum Level of the Antiinflammatory Cytokine Interleukin-10 Is an Important Prognostic Determinant in Patients With Acute Coronary Syndromes"; Circulation; Apr. 29, 2003; pp. 2109-2114; vol. 107; American Heart Association.
Ho et al.; "Isolation of anti-CD22 Fv with high affinity by Fv display on human cells"; PNAS; Jun. 20, 2006; pp. 9637-9642 (with attached correction page); vol. 103, No. 25.
Hou et al.; "Disintegration of Biomacromolecules by Dielectric Barrier Discharge Plasma in Helium at Atmospheric Pressure"; IEEE Transactions on Plasma Science; Aug. 2008; pp. 1633-1637; vol. 36, No. 4; IEEE.
Hu et al.; "Preparation of a biochip on porous silicon and application for label-free detection of small molecule-protein interactions"; Rapid Communications in Mass Spectrometry.; 2007; pp. 1277-1281; vol. 21; John Wiley & Sons, Ltd.
Hume et al.; "The mononuclear phagocyte system revisited"; Journal of Leukocyte Biology; Oct. 2002; pp. 621-627; vol. 72.
Hussein et al.; "Effect of Hemoperfusion Using Polymyxin B-Immobilized Fiber on IL-6, HMGB-1, and IFN Gamma in a Neonatal Sepsis Model"; Pediatric Research; 2005; pp. 309-314; vol. 58, No. 2; International Pediatric Research Foundation, Inc.
Janda et al.; "Induction of an Antibody That Catalyzes the Hydrolysis of an Amide Bond"; Science; Sep. 2, 1988; pp. 1188-1191; vol. 241.
Jayasena, Sumedha D.; "Aptamers: An Emerging Class of Molecules That Rival Antibodies in Diagnostics"; Clinical Chemistry; 1999; pp. 1628-1650; vol. 45, No. 9.
Jin et al.; "Immobilization of plasmid DNA on an anti-DNA antibody modified coronary stent for intravascular site-specific gene therapy"; The Journal of Gene Medicine; 2008; pp. 421-429; vol. 10; John Wiley & Sons, Ltd.
Kam et al.; "Carbon nanotubes as multifunctional biological transporters and near-infrared agents for selective cancer cell destruction"; PNAS; Aug. 16, 2005; pp. 11600-11605; vol. 102, No. 33; The National Academy of Sciences of the USA.
Kaneko et al.; "Successful treatment of digoxin intoxication by haemoperfusion with specific columns for β2-microglobin-adsorption (Lixelle™) in a maintenance haemodialysis patient"; Nephrol Dial Transplant; 2001; pp. 195-196; vol. 16.
Katial et al.; "Deleterious effects of electron beam radiation on allergen extracts"; J Allergy Clin Immunol; Aug. 2002; pp. 215-219; vol. 110, No. 2.
Kellum et al.; "Understanding the Inflammatory Cytokine Response in Pneumonia and Sepsis"; Arch Intern Med; Aug. 13/27, 2007; pp. 1655-1663; vol. 167, No. 15; American Medical Association.
Knappik et al.; "Fully Synthetic Human Combinatorial Antibody Libraries (HuCAL) Based on Modular Consensus Frameworks and CDRs Randomized with Trinucleotides"; J. Mol. Biol.; 2000; pp. 57-86; vol. 296; Academic Press.
Koo et al.; "Development of a Streptavidin-Conjugated Single-Chain Antibody That Binds *Bacillus cereus* Spores"; Applied and Environmental Microbiology; Jul. 1998; pp. 2497-2502; vol. 64, No. 7; American Society for Microbiology.
Kupper et al.; "Generation of human antibody fragments against *Streptococcus mutans* using a phage display chain shuffling approach"; BMC Biotechnology; 2005; pp. 1-12; vol. 5, No. 4; BioMed Central Ltd.
Kurt et al.; "Serum IL-1β, IL-6, IL-8, and TNF-α Levels in Early Diagnosis and Management of Neonatal Sepsis"; Mediators of Inflammation; pp. 1-5; vol. 2007; Hindawi Publishing Corporation.
Kushi et al.; "Early hemoperfusion with an immobilized polymyxin B fiber column eliminates humoral mediators and improves pulmonary oxygenation"; Critical Care, pp. R653-R661; vol. 9, No. 6.
Lacroix-Desmazes et al.; "Catalytic IgG from Patients with Hemophilia A Inactivate Therapeutic Factor VIII"; The Journal of Immunology; 2006; pp. 1355-1363; The American Association of Immunologists, Inc.
Lee et al.; "Performance of an Immobilized Trypsin System for Improving Oxidative Stability of Milk"; Journal of Dairy Science; Aug. 30, 1974; pp. 473-476; vol. 58, No. 4.
Li et al.; "A Patient-Specific in silico Model of Inflammation and Healing Tested in Acute Vocal Fold Injury"; PLoS ONE; Jul. 2008; pp. 1-11; vol. 3, Issue 7.
Lill et al.; "Microwave-Assisted Proteomics"; Mass Spectrometry Reviews; 2007; pp. 657-671; vol. 26; Wiley Periodicals, Inc.
López-Ferrer et al.; "Rapid Sample Processing for LC-MS-Based Quantitative Proteomics Using High Intensity Focused Ultrasound"; Journal of Proteome Research; 2008; pp. 3860-3867; vol. 7, No. 9; American Chemical Society.
Maloney et al.; "Implantable Microchips for Controlled Drug Delivery"; Proceedings of the 26th Annual International Conference of the IEEE EMBS; Sep. 1-5, 2004; pp. 2668-2669; IEEE.
Mesnil De Rochemont et al.; "Diffusion-Weighted MR Imaging Lesions after Filter-Protected Stenting of High-Grade Symptomatic Carotid Artery Stenoses"; AJNR Am J Neuroradiol; Jun.-Jul. 2006; pp. 1321-1325; vol. 27.
Miyata et al.; "Tumor marker-responsive behavior of gels prepared by biomolecular imprinting"; PNAS; Jan. 31, 2006; pp. 1190-1193; vol. 103, No. 5; The National Academy of Sciences of the USA.
Nakada et al.; "Continuous Hemodiafiltration with PMMA Hemofilter in the Treatment of Patients with Septic Shock"; Mol Med; May-Jun. 2008; pp. 257-263; vol. 14, No. 5-6.
Nakada et al.; "Blood Purification for hypercytokinemia"; Transfusion and Apheresis Science; 2006; pp. 253-264; vol. 35; Elsevier Ltd.
Narasipura et al.; "P-Selectin-Coated Microtube for Enrichment of CD34+ Hematopoietic Stem and Progenitor Cells from Human Bone Marrow"; Clinical Chemistry; 2008; pp. 77-85; vol. 54, No. 1; American Association for Clinical Chemistry.
Nitin et al.; "Peptide-linked molecular beacons for efficient delivery and rapid mRNA detection in living cells"; Nucleic Acids Research; 2004; pp. 1-8; vol. 32, No. 6; Oxford University Press.
Nowlan et al.; "Systemic cytokine levels and the effects of etanercept in TNF receptor-associated periodic syndrome (TRAPS) involving a C33Y mutation in TNFRSF1A"; Rheumatology; 2006; pp. 31-37; vol. 45; Oxford University Press on behalf of the British Society for Rheumatology.
Oda et al.; "Cytokine Adsorptive Property of Various Adsorbents in Immunoadsorption Columns and a Newly Developed Adsorbent: An in vitro Study"; Blood Purification; 2004; pp. 530-536; vol. 22; S. Karger AG, Basel.
Ozaki et al.; "Cytokine and Cytokine Receptor Pleiotropy and Redundancy"; The Journal of Biological Chemistry; Aug. 16, 2002; pp. 29355-29358; vol. 277, No. 33.
Peppas et al.; "Polymers and Gels as Molecular Recognition Agents"; Pharmaceutical Research; May 2002; pp. 578-587; vol. 19, No. 5; Plenum Publishing Corporation.
Pervan et al.; "Proteasome Structures Affected by Ionizing Radiation"; Mol Cancer Res; Jul. 2005; pp. 381-390; vol. 3, No. 7.
Piehler et al.; "Fast Transient Cytokine-Receptor Interactions Monitored in Real Time by Reflectometric Interference Spectroscopy"; Analytical Biochemistry; 2001; pp. 173-186; vol. 289; Academic Press.
Ponomarenko et al.; "Autoantibodies to myelin basic protein catalyze site-specific degradation of their antigen"; PNAS; Jan. 10, 2006; pp. 281-286; vol. 103, No. 2; The National Academy of Sciences of the USA.
Proske et al.; "Aptamers-basic research, drug development, and clinical applications"; Appl Microbiol Biotechnol; 2005; pp. 367-374; vol. 69; Springer-Verlag.
Raghavan et al.; "BIAcore: a microchip-based system for analyzing the formation of macromolecular complexes"; Structure; Apr. 15, 1995; pp. 331-333; vol. 3; No. 4; Current Biology Ltd.
Remick, Daniel G.; "Cytokine Therapeutics for the Treatment of Sepsis: Why has Nothing Worked?"; Current Pharmaceutical Design; 2003; pp. 1-8; vol. 9, No. 1; Bentham Science Publishers Ltd.

Renneisen et al.; "Inhibition of Expression of Human Immunodeficiency Virus-1 in Vitro by Antibody-targeted Liposomes Containing Antisense RNA to the *env* Region"; The Journal of Biological Chemistry; Sep. 25, 1990; pp. 16337-16342; vol. 265, No. 27; The American Society for Biochemistry and Molecular Biology, Inc.

Samia et al.; "Quantum Dot-based Energy Transfer: Perspectives and Potential for Applications in Photodynamic Therapy"; Photochemistry and Photobiology; 2006; pp. 617-625; vol. 82; American Society for Photobiology.

Simmons et al.; "Insights into Inflammation and Influenza"; The New England Journal of Medicine; Oct. 9, 2008; pp. 1621-1623; Massachusetts Medical Society.

Spear et al.; "Isolation, characterization, and recovery of small peptide phage display epitopes selected against viable malignant glioma cells"; Cancer Gene Therapy; 2001; pp. 506-511; vol. 8, No. 7; Nature Publishing Group.

Sriskandan et al.; "The immunology of sepsis"; J Pathol; 2008; pp. 211-223; vol. 214; John Wiley & Sons, Ltd.

Stegmayr, Bernd G.; "Is There a Future for Adsorption Techniques in Sepsis?"; Blood Purification; 2000; pp. 149-155; vol. 18; S. Karger AG, Basel.

Stegmayr, Bernd G.; "Is There a Place for Apheresis in Patients with Severe Sepsis or Multi Organ Dysfunction Syndrome?"; Turk J Haematol; 2000; pp. 5-11; vol. 17, No. 1.

Suntharalingam et al.; "Cytokine Storm in a Phase 1 Trial of the Anti-CD28 Monoclonal Antibody TGN1412"; The New England Journal of Medicine; Sep. 7, 2006; pp. 1018-1028; vol. 355, No. 10; Massachusetts Medical Society.

Szodoray et al.; "Programmed Cell Death in Rheumatoid Arthritis Peripheral Blood T-Cell Subpopulations Determined by Laser Scanning Cytometry"; Laboratory Investigation; Dec. 2003; pp. 1839-1848; vol. 83, No. 12; The United States and Canadian Academy of Pathology, Inc.

Takenaka et al.; "Lixelle ameliorates idiopathic thrombocytopenic purpura"; Nephrol Dial Transplant; 2003; pp. 1032-1033; vol. 18.

Taniguchi et al.; "A novel adsorbent of circulating bacterial toxins and cytokines: The effect of direct hemoperfusion with CTR column for the treatment of experimental endotoxemia"; Crit Care Med; 2006; pp. 800-806; vol. 34, No. 3; Lippincott Williams & Wilkins.

Tetta et al.; "Do circulating cytokines really matter in sepsis?"; Kidney International; 2003; pp. S69-S71; vol. 63, Supplement 84; International Society of Nephrology.

Tsuchida et al.; "Direct hemoperfusion by using Lixelle column for the treatment of systemic inflammatory response syndrome"; International Journal of Molecular Medicine; 2002; pp. 485-488; vol. 10.

Tsuchida et al.; "Blood Purification for Critical Illness: Cytokines Adsorption Therapy"; Therapeutic Apheresis and Dialysis; 2006; pp. 25-31; vol. 10, No. 1; Blackwell Publishing Asia Pty Ltd.

Vashist, Sandeep Kumar; "A Review of Microcantilevers for Sensing Applications"; Journal of Nanotechnology Online; Jun. 2007; pp. 1-15; vol. 3.

Venkataraman et al.; "Clinical review: Extracorporeal blood purification in severe sepsis"; Critical Care; Apr. 2003; pp. 139-145; vol. 7, No. 2; Biomed Central Ltd.

Vincent et al.; "A Pilot-Controlled Study of a Polymyxin B-Immobilized Hemoperfusion Cartridge in Patients with Severe Sepsis Secondary to Intra-Abdominal Infection"; SHOCK, 2005; pp. 400-405; vol. 23, No. 5.

Vodovotz et al.; "Mathematical models of the acute inflammatory response"; Current Opinion in Critical Care; 2004; pp. 383-390; vol. 10; Lippincott Williams & Wilkins.

Vodovotz et al.; "Translational Systems Biology of Inflammation"; PLoS Computational Biology; Apr. 2008; pp. 1-6; vol. 4, Issue 4.

Vuckovic et al.; "Gamma-radiation induced damage of proteins in the thick fraction of egg white"; J. Serb. Chem. Soc.; 2005; pp. 1255-1262; vol. 70, No. 11.

Walsh et al.; "Atmospheric Dielectric-Barrier Discharges Scalable From 1 mm to 1 m"; IEEE Transactions on Plasma Science; Aug. 2008; pp. 1314-1315; vol. 36, No. 4; IEEE.

Wang et al.; "Time course of plasma gelsolin concentrations during severe sepsis in critically ill surgical patients"; Critical Care; 2008; pp. 1-6; vol. 12, No. 4; Biomed Central Ltd.

Weber et al.; "Extracorporeal Removal of Proinflammatory Cytokines by Specific Adsorption onto Microspheres"; ASAIO Journal; 1996; pp. M908-M911; vol. 42.

Wentworth et al.; "Antibodies have the intrinsic capacity to destroy antigens"; PNAS; Sep. 26, 2000; pp. 10930-10935; vol. 97, No. 20.

Wentworth, Jr. et al.; "Antibody Catalysis of the Oxidation of Water"; Science; Sep. 7, 2001; pp. 1806-1811; vol. 293; American Association for the Advancement of Science.

Wentworth, Jr., Paul; "Antibody Design by Man and Nature"; Science; Jun. 21, 2002; pp. 2247-2249; vol. 296.

Wojciechowski et al.; "Capture and enrichment of CD34-positive haematopoietic stem and progenitor cells from blood circulation using P-selectin in an implantable device"; British Journal of Haematology; Jan. 23, 2008; pp. 673-681; vol. 140; Blackwell Publishing Ltd.

Yang et al.; "On-Chip Electrochemical Impedance Spectroscopy for Biosensor Arrays"; IEEE Sensors; Oct. 22-25, 2006; pp. 93-96; ICEE.

Yang et al.; "Engineering Target-Responsive Hydrogels Based on Aptamer-Target Interactions"; J. Am. Chem. Soc.; 2008; pp. 6320-6321; vol. 130, No. 20; American Chemical Society.

Ye et al.; "Molecularly imprinted polymers as antibody and receptor mimics for assays, sensors and drug discovery"; Anal Bioanal Chem; 2004; pp. 1887-1897; vol. 378; Springer-Verlag.

Zenker et al.; "From Inverse Problems in Mathematical Physiology to Quantitative Differential Diagnoses"; PLoS Computational Biology; Nov. 2007; pp. 2072-2086; vol. 3, Issue 11.

Zhao et al.; "Cytokine Production by Skin-Derived Mast Cells: Endogenous Proteases Are Responsible for Degradation of Cytokines"; The Journal of Immunology; 2005; pp. 2635-2642; vol. 175; The American Association of Immunologists, Inc.

"Molecule pages live"; Nature Cell Biology; Jan. 2004; p. 1; vol. 6, No. 1; Nature Publishing Group.

* cited by examiner $x_1, x_2, x_3, x_4\ldots$ = concentrations of inflammatory mediator $X$ $y_1, y_2, y_3, y_4\ldots$ = concentrations of inflammatory mediator $Y$ $\sigma_1, \sigma_2, \sigma_3 \ldots$ = standard deviation $$f = \frac{(x_1-y_1)^2}{(\sigma_1)^2} + \frac{(x_2-y_2)^2}{(\sigma_2)^2} + \frac{(x_3-y_3)^2}{(\sigma_3)^2} + \cdots$$

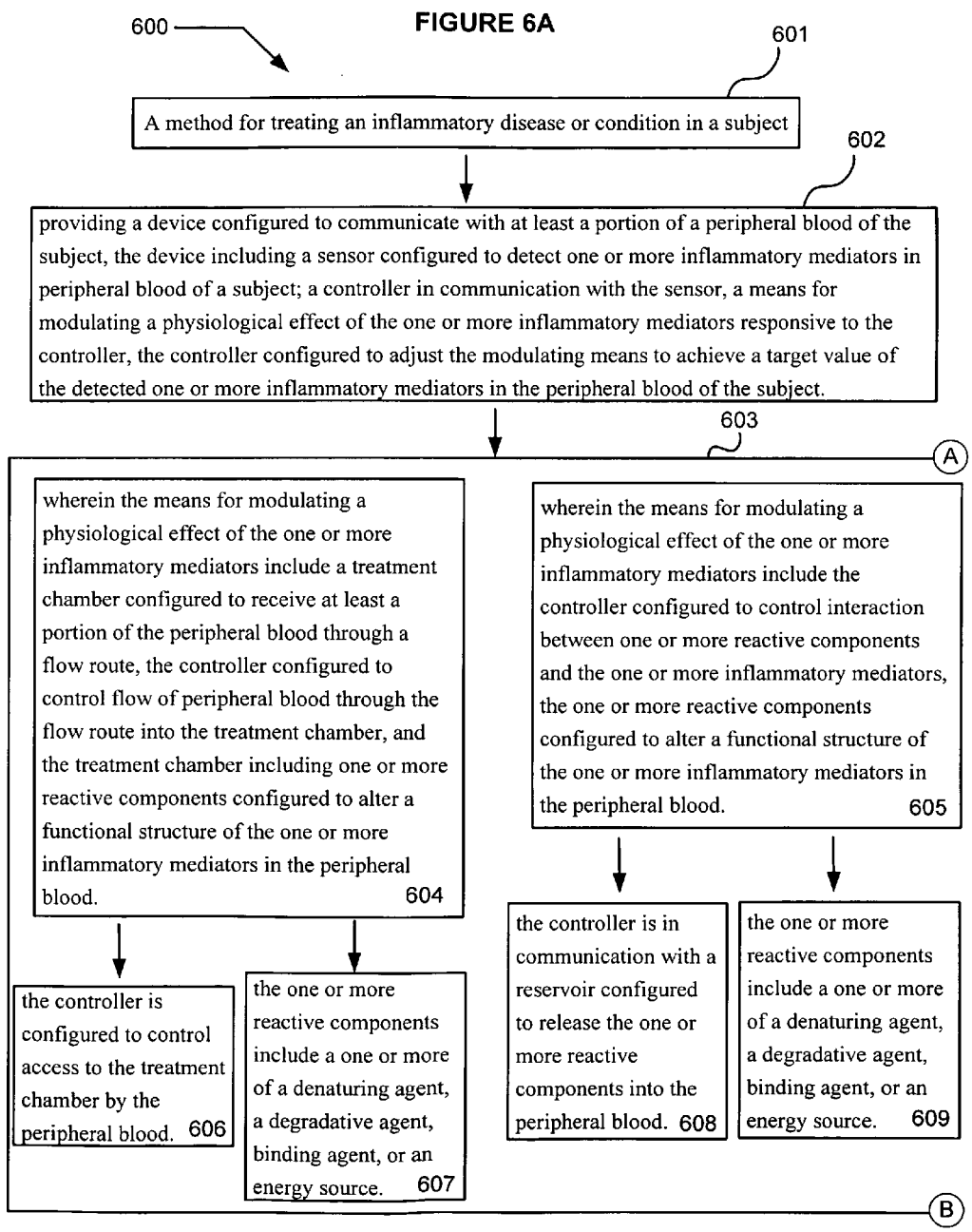

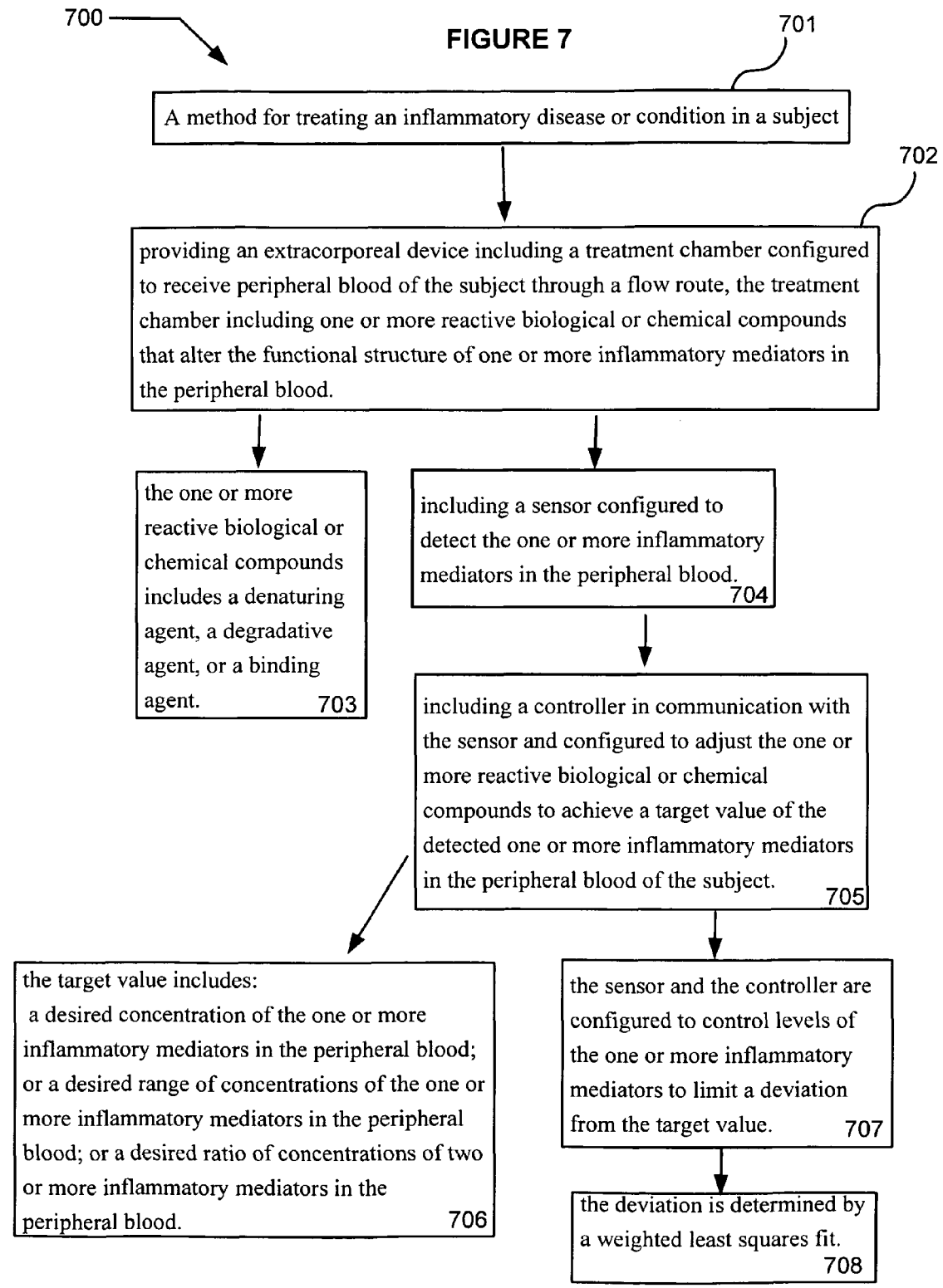

DEVICE, SYSTEM, AND METHOD FOR CONTROLLABLY REDUCING INFLAMMATORY MEDIATORS IN A SUBJECT

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)). All subject matter of the Related Applications and of any and all parent, grandparent, great-grandparent, etc. applications of the Related Applications is incorporated herein by reference to the extent such subject matter is not inconsistent herewith.

RELATED APPLICATIONS

For purposes of the USPTO extra-statutory requirements, the present application constitutes a continuation-in-part of U.S. patent application Ser. No. 12/380,400, entitled DEVICE, SYSTEM, AND METHOD FOR CONTROLLABLY REDUCING INFLAMMATORY MEDIATORS IN A SUBJECT, naming RODERICK A. HYDE, MURIEL Y. ISHIKAWA, EDWARD K.Y. JUNG, ROBERT LANGER, ERIC C. LEUTHARDT, NATHAN P. MYHRVOLD, ELIZABETH A. SWEENEY, AND LOWELL L. WOOD, JR. as inventors, filed 25 Feb. 2009, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

SUMMARY

Devices, systems, and methods are disclosed herein for controlling or modulating an inflammatory response in a subject. Devices, systems, and methods are disclosed that alter the functional structure or biological activity of one or more inflammatory mediators in the peripheral blood of the subject. The device or system is useful in a method for treating an inflammatory disease or condition in the subject. Diseases or conditions related to either acute or chronic inflammatory response include, but are not limited to, systemic inflammatory response syndrome, sepsis, septic shock, multiple organ dysfunction syndrome, ischemia reperfusion, hyperreactive airway disease, (e.g., asthma, chronic obstructive pulmonary disease, rhinitis, sinusitis), allergic reaction, anaphylaxis, pulmonary failure, adult respiratory distress syndrome (ARDS), allograft rejection, graft versus host disease (GVHD), chronic inflammatory disease, psoriatic arthritis, rheumatoid arthritis, chemical or biological agent exposure (due to warfare, accident, or occupation), infectious disease, malaria, anthrax, viral hepatitis, viral infection, influenza, smallpox, HIV, myocardial ischemia, or autoimmune disease.

An extracorporeal device is disclosed that includes a treatment chamber configured to receive peripheral blood of a subject through a flow route, the treatment chamber including one or more reactive biological or chemical compounds that alter the functional structure of one or more inflammatory mediators in the peripheral blood of the subject. The one or more reactive components can include, but are not limited to, one or more of a denaturing agent, a degradative agent, binding agent, or an energy source.

In an aspect, the one or more reactive components can be configured to decrease an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can modulate an activity of an intermediate which modulates the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can increase an activity of an intermediate which decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can decrease an activity of an intermediate which decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. In an aspect, the one or more reactive components can be configured to modulate an activity of one or more of anaphylatoxins, cytokines, chemokines, leukotrienes, prostaglandins, complement, coagulation factors, or proinflammatory cytokines. The one or more denaturing agents can include, but is not limited to, at least of an acid, base, solvent, cross-linking agent, chaotropic agent, disulfide bond reducer, enzyme, drug, cell, or radical ion. The one or more degradative agents can include, but is not limited to, at least one of an enzyme, coenzyme, enzyme complex, catalytic antibody, proteasome, strong acid, strong base, radical, photoactivatable agent, drug, cell, or radical ion. The catalytic antibody can generate a radical ion. The one or more binding agents on a matrix adapted to the treatment chamber can be configured to sequester at least one of the one or more inflammatory mediators from the blood. The one or more binding agents can include, but are not limited to, one or more of antibodies, receptors, or cognates and binds to at least one of the one or more inflammatory mediators. The one or more binding agents include, but are not limited to, one or more of lectin, binding protein, catalytic antibody, catalytic aptamer, protease conjugate, or photoactivatable agent conjugate.

In an aspect, the device can further include a sensor configured to detect the one or more inflammatory mediators in the peripheral blood. In a further aspect, the device can further include a controller in communication with the sensor and configured to adjust the one or more reactive biological or chemical compounds to achieve a target value of the detected one or more inflammatory mediators in the peripheral blood of the subject. The controller can be configured to control the interaction by modulating blood flow into the treatment chamber. The controller can be configured to control the interaction by modulating release of the one or more biological or chemical compounds into the treatment chamber. The target value can include a desired concentration of the one or more inflammatory mediators in the peripheral blood. The target value can include a desired range of concentrations of the one or more inflammatory mediators in the peripheral blood. The target value can include a desired ratio of concentrations of two or more inflammatory mediators in the peripheral blood. The target value can include a desired ratio of levels of two or more inflammatory mediators in the peripheral blood. The sensor and the controller can be configured to control levels of the one or more inflammatory mediators to substantially attain the target value. The sensor and the controller can be configured to control levels of the one or more inflammatory mediators to limit a deviation from the target value. The deviation can be determined by a weighted least squares fit. The sensor can be configured to target the device to a site of inflammation in the subject. The sensor can target the device to the site of inflammation and to an elevated level of the inflammatory mediators. The controller can be configured to control interaction between the one or more reactive components and the one or more inflammatory mediators in the treatment chamber. The controller can be configured to control access to the treatment chamber by the peripheral blood. The sensor includes, but is not limited to, a biosensor, chemical sensor, physical sensor, or optical sensor. The sensor includes, but is not limited to, one or more of an aptamer, antibody, or receptor. The sensor includes, but is not limited to, one or more of a recognition-based substrate, an aptamer-based substrate, an antibody-based substrate, surface plasmon resonance, genetically-modified cells, or genetically-modified cells with receptor-linked signaling. The genetically-modified cells can include receptor-linked signaling by fluorogen-activating proteins. The sensor can be configured to target the device to a site having an elevated level of the inflammatory mediators. The sensor can be configured to detect one or more of cytokines, T-lymphocytes, B-lymphocytes, or antibodies. The sensor can be configured to detect one or more of body temperature, vital signs, edema, oxygen level, or pathogen/toxin level of the subject. The sensor can be configured to detect one or more of anaphylatoxins, chemokines, leukotrienes, prostaglandins, complement, coagulation factors, or proinflammatory cytokines. The sensor can be configured to detect one or more of TNF-$\alpha$, IL-1, IL-1$\beta$, IL-6, IL-8, IL-10, IL-12, LPB, IFN-$\gamma$, LIF, MIF, MIP-1, MCP-1, C3-a, C5-a, exotoxins or endotoxins. The device includes, but is not limited to, a dialysis device, hemoperfusion device, apheresis device, intravenous device, or patch device.

A method for treating an inflammatory disease or condition in a subject is disclosed that includes providing an extracorporeal device including a treatment chamber configured to receive peripheral blood of the subject through a flow route, the treatment chamber including one or more reactive biological or chemical compounds that alter the functional structure of one or more inflammatory mediators in the peripheral blood. The one or more reactive components can include, but are not limited to, one or more of a denaturing agent, a degradative agent, binding agent, or an energy source.

In an aspect, the one or more reactive components can be configured to decrease an activity of one or more of TNF-$\alpha$, IL-1, IL-1$\beta$, IL-6, IL-8, IL-10, IL-12, LPB, IFN-$\gamma$, LIF, MIF, MIP-1, MCP-1, C3-a, C5-a, exotoxin, or endotoxin. The one or more reactive components can modulate an activity of an intermediate which modulates the activity of one or more of TNF-$\alpha$, IL-1, IL-1$\beta$, IL-6, IL-8, IL-10, IL-12, LPB, IFN-$\gamma$, LIF, MIF, MIP-1, MCP-1, C3-a, C5-a, exotoxin, or endotoxin. The one or more reactive components can increase an activity of an intermediate which decreases the activity of one or more of TNF-$\alpha$, IL-1, IL-1$\beta$, IL-6, IL-8, IL-10, IL-12, LPB, IFN-$\gamma$, LIF, MIF, MIP-1, MCP-1, C3-a, C5-a, exotoxin, or endotoxin. The one or more reactive components can decrease an activity of an intermediate which decreases the activity of one or more of TNF-$\alpha$, IL-1, IL-1$\beta$, IL-6, IL-8, IL-10, IL-12, LPB, IFN-$\gamma$, LIF, MIF, MIP-1, MCP-1, C3-a, C5-a, exotoxin, or endotoxin. In an aspect, the one or more reactive components can be configured to modulate an activity of one or more of anaphylatoxins, cytokines, chemokines, leukotrienes, prostaglandins, complement, coagulation factors, or proinflammatory cytokines. The one or more denaturing agents can include, but is not limited to, at least of an acid, base, solvent, cross-linking agent, chaotropic agent, disulfide bond reducer, enzyme, drug, cell, or radical ion. The one or more degradative agents can include, but is not limited to, at least one of an enzyme, coenzyme, enzyme complex, catalytic antibody, proteasome, strong acid, strong base, radical, photoactivatable agent, drug, cell, or radical ion. The catalytic antibody can generate a radical ion. The one or more binding agents on a matrix adapted to the treatment chamber can be configured to sequester at least one of the one or more inflammatory mediators from the blood. The one or more binding agents can include, but are not limited to, one or more of antibodies, receptors, or cognates and binds to at least one of the one or more inflammatory mediators. The one or more binding agents include, but are not limited to, one or more of lectin, binding protein, catalytic antibody, catalytic aptamer, protease conjugate, or photoactivatable agent conjugate.

In an aspect, the method can further include a sensor configured to detect the one or more inflammatory mediators in the peripheral blood. In a further aspect, the method can further include a controller in communication with the sensor and configured to adjust the one or more reactive biological or chemical compounds to achieve a target value of the detected one or more inflammatory mediators in the peripheral blood of the subject. The controller can be configured to control the interaction by modulating blood flow into the treatment chamber. The controller can be configured to control the interaction by modulating release of the one or more biological or chemical compounds into the treatment chamber. The target value can include a desired concentration of the one or more inflammatory mediators in the peripheral blood. The target value can include a desired range of concentrations of the one or more inflammatory mediators in the peripheral blood. The target value can include a desired ratio of concentrations of two or more inflammatory mediators in the peripheral blood. The target value can include a desired ratio of levels of two or more inflammatory mediators in the peripheral blood. The sensor and the controller can be configured to control levels of the one or more inflammatory mediators to substantially attain the target value. The sensor and the controller can be configured to control levels of the one or more inflammatory mediators to limit a deviation from the target value. The deviation can be determined by a weighted least squares fit. The sensor can be configured to target the device to a site of inflammation in the subject. The sensor can target the device to the site of inflammation and to an elevated level of the inflammatory mediators. The controller can be configured to control interaction between the one or more reactive components and the one or more inflammatory mediators in the treatment chamber. The controller can be configured to control access to the treatment chamber by the peripheral blood. The sensor includes, but is not limited to, a biosensor, chemical sensor, physical sensor, or optical sensor. The sensor includes, but is not limited to, one or more of an aptamer, antibody, or receptor. The sensor includes, but is not limited to, one or more of a recognition-based substrate, an aptamer-based substrate, an antibody-based substrate, surface plasmon resonance, genetically-modified cells, or genetically-modified cells with receptor-linked signaling. The genetically-modified cells can include receptor-linked signaling by fluorogen-activating proteins. The sensor can be configured to target the device to a site having an elevated level of the inflammatory mediators. The sensor can be configured to detect one or more of cytokines, T-lymphocytes, B-lymphocytes, or antibodies. The sensor can be configured to detect one or more of body temperature, vital signs, edema, oxygen level, or pathogen/toxin level of the subject. The sensor can be configured to detect one or more of anaphylatoxins, chemokines, leukotrienes, prostaglandins, complement, coagulation factors, or proinflammatory cytokines. The sensor can be configured to detect one or more of TNF-α, IL-1, IL-1β, IL-6, IL-8, IL-10, IL-12, LPB, IFN-γ, LIF, MIF, MIP-1, MCP-1, C3-a, C5-a, exotoxins or endotoxins A system is disclosed that includes an extracorporeal device including a treatment chamber configured to receive peripheral blood of a subject through a flow route the treatment chamber including one or more reactive biological or chemical compounds that alter a functional structure of one or more inflammatory mediators in the peripheral blood of the subject, a sensor for detecting the one or more inflammatory mediators in the peripheral blood and for providing an output related thereto, and a controller for receiving the output of the sensor and configured to control interaction between the one or more biological or chemical compounds and the one or more inflammatory mediators in the treatment chamber, wherein the sensor and the controller function relative to a target value of at least one of the one or more inflammatory mediators in the peripheral blood. The controller can be configured to control the interaction by modulating blood flow into the treatment chamber. The controller can be configured to control the interaction by modulating release of the one or more biological or chemical compounds into the treatment chamber. The one or more reactive components can include, but are not limited to, one or more of a denaturing agent, a degradative agent, binding agent, or an energy source.

In an aspect, the one or more reactive components can be configured to decrease an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can modulate an activity of an intermediate which modulates the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can increase an activity of an intermediate which decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can decrease an activity of an intermediate which decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. In an aspect, the one or more reactive components can be configured to modulate an activity of one or more of anaphylatoxins, cytokines, chemokines, leukotrienes, prostaglandins, complement, coagulation factors, or proinflammatory cytokines.

A device is disclosed that includes a system including a signal-bearing medium including one or more instructions for treatment of a subject through an extracorporeal device including a treatment chamber configured to receive a peripheral blood through a flow route, the treatment chamber including one or more reactive biological or chemical compounds that alter a functional structure of one or more inflammatory mediators in the peripheral blood of the subject, one or more instructions for receiving data including data from a sensor configured to detect the one or more inflammatory mediators in the peripheral blood, and one or more instructions for receiving data including data from a controller for receiving the output of the sensor and configured to control interaction between the one or more biological or chemical compounds and the one or more inflammatory mediators in the treatment chamber, wherein the sensor and the controller function relative to a target value of at least one of the one or more inflammatory mediators in the peripheral blood. The device can further include one or more instructions for sending or receiving data including data to or data from the controller informed by the sensor and configured to control interaction between the one or more reactive components and the one or more inflammatory mediators in the treatment chamber. The controller can be configured to control the interaction by modulating blood flow into the treatment chamber. The controller can be configured to control the interaction by modulating release of the one or more biological or chemical compounds into the treatment chamber. The one or more reactive components can include, but are not limited to, one or more of a denaturing agent, a degradative agent, binding agent, or an energy source.

In an aspect, the one or more reactive components can be configured to decrease an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can modulate an activity of an intermediate which modulates the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can increase an activity of an intermediate which decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. The one or more reactive components can decrease an activity of an intermediate which decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin. In an aspect, the one or more reactive components can be configured to modulate an activity of one or more of anaphylatoxins, cytokines, chemokines, leukotrienes, prostaglandins, complement, coagulation factors, or proinflammatory cytokines.

A system is disclosed which includes at least one computer program included on a computer-readable medium for use with at least one computer system wherein the computer program includes a plurality of instructions including one or more instructions for determining at least one treatment of peripheral blood of a subject through an extracorporeal device including a treatment chamber configured to receive a peripheral blood through a flow route, the treatment chamber including one or more reactive biological or chemical compounds that alter a functional structure of one or more inflammatory mediators in the peripheral blood of the subject, one or more instructions for receiving data including data from a sensor configured to detect the one or more inflammatory mediators in the peripheral blood, and one or more instructions for receiving data including data from a controller for receiving the output of the sensor and configured to control interaction between the one or more biological or chemical compounds and the one or more inflammatory mediators in the treatment chamber, wherein the sensor and the controller function relative to a target value of at least one of the one or more inflammatory mediators in the peripheral blood. The system can further include one or more instructions for sending or receiving data including data to or data from the controller informed by the sensor and configured to control interaction between the one or more reactive components and the one or more inflammatory mediators in the treatment chamber. The controller can be configured to control the interaction by modulating blood flow into the treatment chamber. The controller can be configured to control the interaction by modulating release of the one or more biological or chemical compounds into the treatment chamber. The one or more reactive biological or chemical compounds can include, but is not limited to, a denaturing agent, a degradative agent or a binding agent.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 7 depicts a logic flowchart of a method for treating an inflammatory disease or condition in a subject

DETAILED DESCRIPTION

Figure 1A:
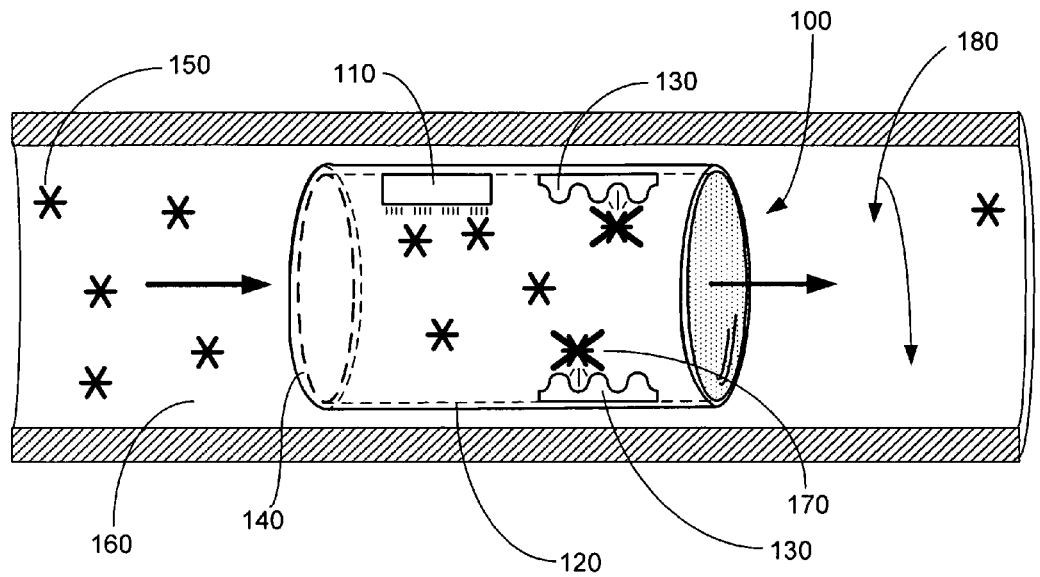
FIGS. 1A and 1B depict a diagrammatic view of an aspect of an exemplary embodiment of an intracorporeal device.

In the following detailed description, reference is made to the accompanying drawings, which form a part hereof. In the drawings, similar symbols typically identify similar components, unless context dictates otherwise. The illustrative embodiments described in the detailed description and drawings are not meant to be limiting. Other embodiments may be utilized, and other changes may be made, without departing from the spirit or scope of the subject matter presented here.

The present application uses formal outline headings for clarity of presentation. However, it is to be understood that the outline headings are for presentation purposes, and that different types of subject matter may be discussed throughout the application (e.g., method(s) may be described under composition heading(s) and/or kit headings, and/or descriptions of single topics may span two or more topic headings). Hence, the use of the formal outline headings is not intended to be in any way limiting.

Devices, systems, and methods are disclosed herein for controlling or modulating an inflammatory response in a subject. Devices, systems, and methods are disclosed that alter the functional structure or biological activity of one or more inflammatory mediators in the peripheral blood of the subject. The device or system is useful in a method for treating an inflammatory disease or condition in the subject. Diseases or conditions related to either acute or chronic inflammatory response include, but are not limited to, systemic inflammatory response syndrome, sepsis, septic shock, multiple organ dysfunction syndrome, ischemia reperfusion, hyperreactive airway disease, (e.g., asthma, chronic obstructive pulmonary disease, rhinitis, sinusitis), allergic reaction, anaphylaxis, pulmonary failure, adult respiratory distress syndrome (ARDS), allograft rejection, graft versus host disease (GVHD), chronic inflammatory disease, psoriatic arthritis, rheumatoid arthritis, chemical or biological agent exposure (due to warfare, accident, or occupation), infectious disease, malaria, anthrax, viral hepatitis, viral infection, influenza, smallpox, HIV, myocardial ischemia, or autoimmune disease.

An extracorporeal device is disclosed that includes a treatment chamber configured to receive peripheral blood of a subject through a flow route, the treatment chamber including one or more reactive biological or chemical compounds that alter the functional structure of one or more inflammatory mediators in the peripheral blood of the subject. The one or more reactive components can include, but are not limited to, one or more of a denaturing agent, a degradative agent, binding agent, or an energy source.

In an aspect, the device can further include a sensor configured to detect the one or more inflammatory mediators in the peripheral blood. In a further aspect, the device can further include a controller in communication with the sensor and configured to adjust the one or more reactive biological or chemical compounds to achieve a target value of the detected one or more inflammatory mediators in the peripheral blood of the subject. The controller can be configured to control the interaction by modulating blood flow into the treatment chamber. The controller can be configured to control the interaction by modulating release of the one or more biological or chemical compounds into the treatment chamber. The target value can include a desired concentration of the one or more inflammatory mediators in the peripheral blood. The target value can include a desired range of concentrations of the one or more inflammatory mediators in the peripheral blood. The target value can include a desired ratio of concentrations of two or more inflammatory mediators in the peripheral blood. The target value can include a desired ratio of levels of two or more inflammatory mediators in the peripheral blood. The sensor and the controller can be configured to control levels of the one or more inflammatory mediators to substantially attain the target value. The sensor and the controller can be configured to control levels of the one or more inflammatory mediators to limit a deviation from the target value. The deviation can be determined by a weighted least squares fit.

A method for treating an inflammatory disease or condition in a subject is disclosed that includes providing an extracorporeal device including a treatment chamber configured to receive peripheral blood of the subject through a flow route, the treatment chamber including one or more reactive biological or chemical compounds that alter the functional structure of one or more inflammatory mediators in the peripheral blood.

A system is disclosed that includes an extracorporeal device including a treatment chamber configured to receive peripheral blood of a subject through a flow route the treatment chamber including one or more reactive biological or chemical compounds that alter a functional structure of one or more inflammatory mediators in the peripheral blood of the subject, a sensor for detecting the one or more inflammatory mediators in the peripheral blood and for providing an output related thereto, and a controller for receiving the output of the sensor and configured to control interaction between the one or more biological or chemical compounds and the one or more inflammatory mediators in the treatment chamber, wherein the sensor and the controller function relative to a target value of at least one of the one or more inflammatory mediators in the peripheral blood.

A device is disclosed that includes a system including a signal-bearing medium including one or more instructions for treatment of a subject through an extracorporeal device including a treatment chamber configured to receive a peripheral blood through a flow route, the treatment chamber including one or more reactive biological or chemical compounds that alter a functional structure of one or more inflammatory mediators in the peripheral blood of the subject, one or more instructions for receiving data including data from a sensor configured to detect the one or more inflammatory mediators in the peripheral blood, and one or more instructions for receiving data including data from a controller for receiving the output of the sensor and configured to control interaction between the one or more biological or chemical compounds and the one or more inflammatory mediators in the treatment chamber, wherein the sensor and the controller function relative to a target value of at least one of the one or more inflammatory mediators in the peripheral blood.

A system is disclosed which includes at least one computer program included on a computer-readable medium for use with at least one computer system wherein the computer program includes a plurality of instructions including one or more instructions for determining at least one treatment of peripheral blood of a subject through an extracorporeal device including a treatment chamber configured to receive a peripheral blood through a flow route, the treatment chamber including one or more reactive biological or chemical compounds that alter a functional structure of one or more inflammatory mediators in the peripheral blood of the subject, one or more instructions for receiving data including data from a sensor configured to detect the one or more inflammatory mediators in the peripheral blood, and one or more instructions for receiving data including data from a controller for receiving the output of the sensor and configured to control interaction between the one or more biological or chemical compounds and the one or more inflammatory mediators in the treatment chamber, wherein the sensor and the controller function relative to a target value of at least one of the one or more inflammatory mediators in the peripheral blood.

Inflammation, Inflammatory Mediators and Inflammatory Disease or Condition

Inflammation is a complex biological response to insults that arise from, for example, chemical, traumatic, or infectious stimuli. It is a protective attempt by an organism to isolate and eradicate the injurious stimuli as well as to initiate the process of tissue repair. The events in the inflammatory response are initiated by a complex series of interactions involving inflammatory mediators, including those released by immune cells and other cells of the body. Histamines and eicosanoids such as prostaglandins and leukotrienes act on blood vessels at the site of infection to localize blood flow, concentrate plasma proteins, and increase capillary permeability. Chemotactic factors, including certain eicosanoids, complement, and especially cytokines known as chemokines, attract particular leukocytes to the site of infection. Other inflammatory mediators, including some released by the summoned leukocytes, function locally and systemically to promote the inflammatory response. Platelet activating factors and related mediators function in clotting, which aids in localization and can trap pathogens, Certain cytokines, e.g., tumor necrosis factor (TNF), and interleukins induce further trafficking and extravasation of immune cells, hematopoiesis, fever, and production of acute phase proteins. Once signaled, some cells and/or their products directly affect the offending pathogens, for example by inducing phagocytosis of bacteria or, as with interferon, providing antiviral effects by shutting down protein synthesis in the host cells. Oxygen radicals, cytotoxic factors and growth factors may also be released to fight pathogen infection and/or to facilitate tissue healing. This cascade of biochemical events propagates and matures the inflammatory response, involving the local vascular system, the immune system, and various cells within the injured tissue. Under normal circumstances, through a complex process of mediator-regulated pro-inflammatory and anti-inflammatory signals, the inflammatory response eventually resolves itself and subsides. For example, the transient and localized swelling associated with a cut is an example of an acute inflammatory response. However, in certain cases resolution may not occur as expected. Prolonged inflammation, known as chronic inflammation, may lead to a progressive shift in the type of cells present at the site of inflammation and is characterized by simultaneous destruction and healing of the tissue from the inflammatory process, as directed by certain mediators. Rheumatoid arthritis is an example of a disease associated with persistent and chronic inflammation.

In some aspects, the inflammatory response becomes uncontrolled as is the case with systemic immune response syndrome (SIRS). SIRS is an inflammatory state of the entire body and may be initiated by ischemia, inflammation, trauma, infection, or a combination thereof. A triggering event, such as trauma, may induce localized release of inflammatory mediators with the goal of initiating an inflammatory response to promote wound repair. Small amounts of local inflammatory mediators are released into the circulation to improve the local response. This may lead to growth factor stimulation and recruitment of macrophages and platelets. Such an acute phase response may be typically well-controlled by a natural decrease in endogenous pro-inflammatory mediators and by the release of endogenous antagonists with the goal of restoring homeostasis. However, if homeostasis is not restored, a significant systemic reaction may occur leading to what is known as "cytokine storm" or hypercytokinemia. A consequence of this is the activation of numerous humoral cascades, the activation of the reticular endothelial system and the subsequent loss of circulatory integrity, potentially leading to end-organ dysfunction and death. In this aspect, the excessive release of inflammatory mediators may lead to destruction of cells and tissue rather than protection. Hypercytokinemia has the potential to do significant damage to body tissues and organs.

Both pro-inflammatory and anti-inflammatory mediators are released into the peripheral system during the hypercytokinemia associated with SIRS. In the case of sepsis or infection-induced SIRS, bacterial ligands such as lipopolysaccharide (LPS) activate toll-like receptors (TLRs) and NF-κB, leading to increased expression and release of the pro-inflammatory mediators, e.g., tumor necrosis factor α (TNF-α) and interleukins IL-1, IL-6, IL-8, and IL-12. See, e.g., Sriskandan & Altmann, *J. Pathol.* 214:211-233, 2008, which is incorporated herein by reference. In contrast, anti-inflammatory mediators such as interleukins IL-4, IL-10 and IL-13 as well as transforming growth factor β (TGF-B-β) suppress gene expression and the synthesis of IL-1, TNF and other pro-inflammatory cytokines. See, e.g., Dinarello *Chest*

112:321-329, 1997, which is incorporated herein by reference. The inability of the immune system to return to homeostasis by balancing the pro-inflammatory and anti-inflammatory mediators may contribute to progression of SIRS to multiple organ failure and potentially death.

Inhibition of TNF-α or IL-1 activity with selective antagonists has not been a successful approach for treating patients with sepsis/SIRS. See, e.g., Remick Curr. Pharm. Des. 9:75-82, 2003). Non-selective removal of inflammatory mediators using hemodialysis, hemofiltration, hemoadsorption, or plasma filtration has had limited success. See, e.g., Venkataraman, et al., Critical Care 7:139-145, 2003; Kushi, et al., Critical Care 9:R659-661, 2005; Nakakda, et al., Transfus. Apher. Sci. 35:253-264, 2006; Nakada, et al., Mol. Med. 14:257-263, 2008, each of which is incorporated herein by reference. In the non-selective approach, both pro-inflammatory and anti-inflammatory mediators are removed from the blood.

Another approach to treating the severe inflammatory response associated with an inflammatory condition can involve controllably removing, modulating or inactivating specific inflammatory mediators at different times over the course of the inflammatory response. The controllable removal, modulation, or inactivation of specific inflammatory mediators may be based on real-time monitoring of a subject's blood. The removal, modulation, or inactivation of at least one inflammatory mediator includes, for example, altering the functional structure of the at least one inflammatory mediator accomplished by blocking a binding site or active site of the at least one inflammatory mediator, by modulating the expression of the at least one inflammatory mediator, by modulating the physiological effect, or by agonizing the activity or expression of an anti-inflammatory mediator.

A device is described herein for altering the functional structure of one or more inflammatory mediators in the peripheral blood of a subject. The modulating means can be configured to altering a functional structure of the one or more inflammatory mediators which refers to decreasing an activity of the one or more of inflammatory mediators, for example, by denaturation, degradation, or inactivation by one or more of an energy source, a biological agent, or a chemical agent. The device can be used in a method for treating an inflammatory disease or condition in the subject. The device can be extracorporeal or intracorporeal, or a combination thereof. The device can include one or more sensors configured to detect one or more inflammatory mediators in the peripheral blood of a subject and configured to control levels of the one or more inflammatory mediators to a target value. The one or more sensors can include, for example, a biosensor, a chemical sensor, a physical sensor, an optical sensor, or a combination thereof. The device can further include one or more treatment chambers configured to receive the peripheral blood of a subject through a flow route. The one or more treatment chambers can include one or more specific binding agents for binding one or more specific inflammatory mediators. The one or more specific binding agents can be attached to one or more substrates in the one or more treatment chambers. The one or more substrates can be one or more surfaces of the one or more treatment chambers. The one or more substrates can include one or more matrix components retained in the one or more treatment chambers. The one or more treatment chambers can include one or more reactive components configured to alter the functional structure of one or more inflammatory mediators found in the peripheral blood of a subject that flow through the flow route. The one or more reactive components include, but are not limited to, a denaturing agent, a degradative agent, an energy source, or a combination thereof. The device further includes a controller that receives data from the one or more sensors and in response to the input data controls flow into and out of the one or more treatment chambers and/or controls release and/or activation of one or more reactive components.

In a further aspect, a method is provided for treating an inflammatory disease or condition in a subject by providing a device configured to communicate with the peripheral blood of the subject. One or more sensors are configured to detect one or more inflammatory mediators in the peripheral blood of the subject. In response to sensing one or more inflammatory mediators, a flow route is provided from the peripheral blood to one or more treatment chambers. The one or more treatment chambers are configured to alter the functional structure of the one or more inflammatory mediators in the peripheral blood and to modulate, reduce, alleviate, or eliminate the inflammatory disease or condition in the subject.

Inflammatory diseases or conditions wherein the inflammation associated with the disease or condition may be modulated, alleviated, treated, prevented, reduced or eliminated by altering the functional structure of one or more inflammatory mediators in the peripheral blood include, but are not limited to, systemic inflammatory response syndrome, sepsis, septic shock, multiple organ dysfunction syndrome, ischemia reperfusion, hyperreactive airway disease, (e.g., asthma, chronic obstructive pulmonary disease, rhinitis, sinusitis), allergic reaction, anaphylaxis, pulmonary failure, adult respiratory distress syndrome (ARDS), allograft rejection, graft versus host disease (GVHD), chronic inflammatory disease, psoriatic arthritis, rheumatoid arthritis, chemical or biological agent exposure (due to warfare, accident, or occupation), infectious disease, malaria, anthrax, viral infection, viral hepatitis, influenza, smallpox, acquired immunodeficiency syndrome (AIDS) associated with HIV infection, myocardial ischemia, or autoimmune disease.

Inflammatory mediators as used herein include pro-inflammatory mediators or anti-inflammatory mediators, or both. The types of inflammatory mediators that may be modulated, agonized, antagonized, reduced, or eliminated by altering, for example, their biological activity or expression or the functional structure include, but are not limited to, cytokines such as interferons (IFN) IFN-α, IFN-β, and IFN-γ; interleukins (IL) IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); erythropoietin (EPO); and thrombopoietin (TPO). The one or more inflammatory mediators may be any of a number of chemotactic cytokines (chemokines) including but not limited to CC chemokines CCL1 through CCL28 exemplified by RANTES (CCL5), MCP-1 (CCL2), LARC (CCL20), MIP-1α (CCL3), and MDC(CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF. Other inflammatory mediators include but are not limited to anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-β and VEGF; soluble tumor necrosis factor receptor (sTNFR I and II); soluble interleukin receptors sIL-1r and sIL-2r; C-reactive protein; CD11b; histamine; serotonin; apolipoprotein A1;

β2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins; and pathogen-derived products including endotoxins such as lipopolysaccharide (LPS); and various exotoxins such as superantigens, e.g., from *Staphylococcus aureus* and *Streptococcus pyogenes*.

Anti-inflammatory mediators include, but are not limited to, IL-4, IL-10, IL-13, transforming growth factor-β (TGF-β), endogenous IL-1 receptor antagonists, as well as endogenous soluble TNF receptors, cyclopentenone prostaglandin $D_2$ ($PGD_2$), $PGE_2$, annexin-1, galectin-1, interferon-α, interferon-β, and lipoxins. IL-4 and IL-13 may be considered anti-inflammatory mediators because they block production of IL-6, IL-1 and TNF-α but they also upregulate the cell surface receptor for IgE complexes, CD23, and stimulate B cells to stimulate IgE production. IL-10 also blocks IL-1 and TNF.

Pro-inflammatory mediators may include, but are not limited to, TNF-α, IL-1β, IL-6, and IL-8, prostaglandins (e.g., PGE2), leukotrienes (e.g., LTB4), CXC chemokines (e.g., macrophage inflammatory protein-2), and platelet activating factor Interleukin-6 (IL-6) is an interleukin that may act as both a pro-inflammatory and anti-inflammatory cytokine. IL-6 is secreted by T cells and macrophages to stimulate immune response to trauma, especially burns or other tissue damage leading to inflammation. The role of IL-6 as an anti-inflammatory cytokine is mediated through its inhibitory effects on TNF-α and IL-1, and activation of IL-1ra and IL-10.

With reference to the figures, and with reference now to FIGS. 1, 2, 3 and 4, depicted is an aspect of a device, system, or method that may serve as an illustrative environment of and/or for subject matter technologies, for example, a device including a sensor configured to detect one or more inflammatory mediators in peripheral blood of a subject and configured to control levels of the one or more inflammatory mediators to a target value, and a treatment chamber responsive to output from the sensor and configured to receive the peripheral blood through a flow route, the treatment chamber including one or more reactive components configured to alter a functional structure of the one or more inflammatory mediators in the peripheral blood of the subject. The device may be intracorporeal or extracorporeal of the subject. The specific methods described herein are intended as merely illustrative of their more general counterparts.

Figure 1B:
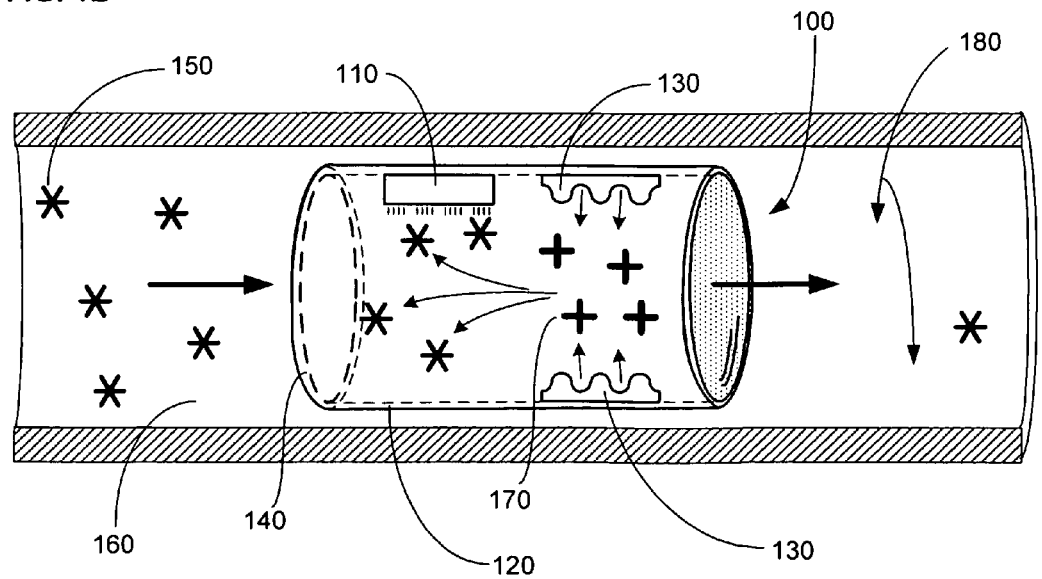

Continuing to refer to FIGS. 1A and 1B, depicted is a partial diagrammatic view of an illustrative embodiment of a device 100 including a sensor 110 configured to detect one or more inflammatory mediators 150 in peripheral blood 160 of a subject and configured to control levels of the one or more inflammatory mediators to a target value, and a treatment chamber 120 including one or more reactive components 130 configured to alter a functional structure of the one or more inflammatory mediators 150 in the peripheral blood of the subject. In FIG. 1A, the device can further include a controller 140 in communication with and responsive to the sensor 110 and configured to control access to the treatment chamber 120 by the peripheral blood 160. The reactive component can further include an affinity binding component 170 to bind the one or more inflammatory mediators 150 and configured to alter a functional structure of the one or more inflammatory mediators. The one or more reactive components 130 include, but are not limited to, a denaturing agent, a degradative agent, or an energy source, which can destroy, degrade, denature the one or more inflammatory mediators 150 or destroy an activity of the one or more inflammatory mediators. The device can be configured to reduce the concentration of inflammatory mediators at one or more sites of inflammation 180 in the subject, or throughout the peripheral blood.

In FIG. 1B, the device can further include a controller 140 configured to be in communication with and responsive to the sensor 110 and configured to control access to the treatment chamber 120 by the peripheral blood 160. The reactive component can further include a diffusible component 170 to bind the one or more inflammatory mediators 150 and configured to alter a functional structure of the one or more inflammatory mediators. The diffusible component 170 can bind to the one or more inflammatory mediators 150 within the treatment chamber or outside in the peripheral blood of the subject. The one or more reactive components 130 or the diffusible component 170 include, but are not limited to, a denaturing agent, a degradative agent, or an energy source, which can destroy, degrade, denature the one or more inflammatory mediators 150 or destroy an activity of the one or more inflammatory mediators.

Figure 2A:
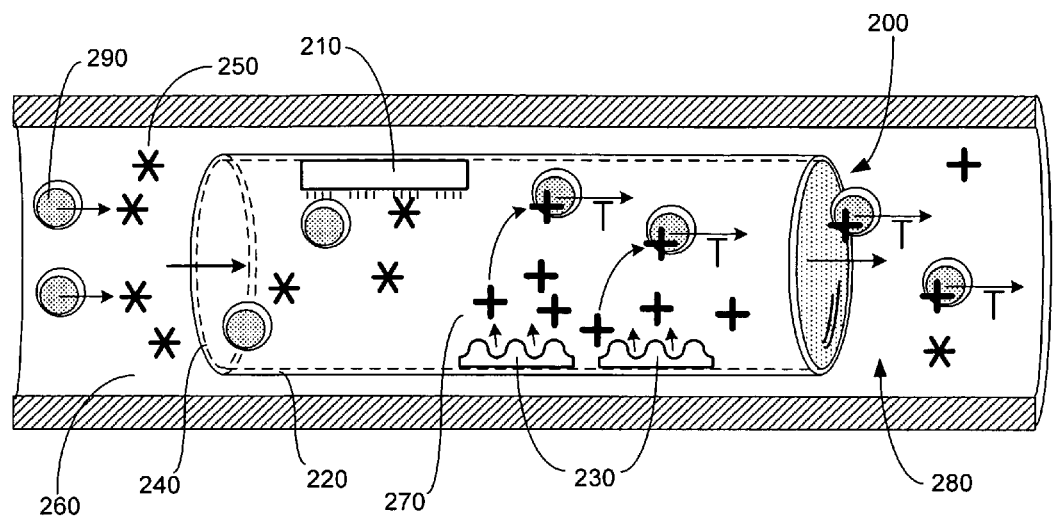
FIGS. 2A and 2B depict a diagrammatic view of an aspect of an exemplary embodiment of an intracorporeal device.
Figure 2B:
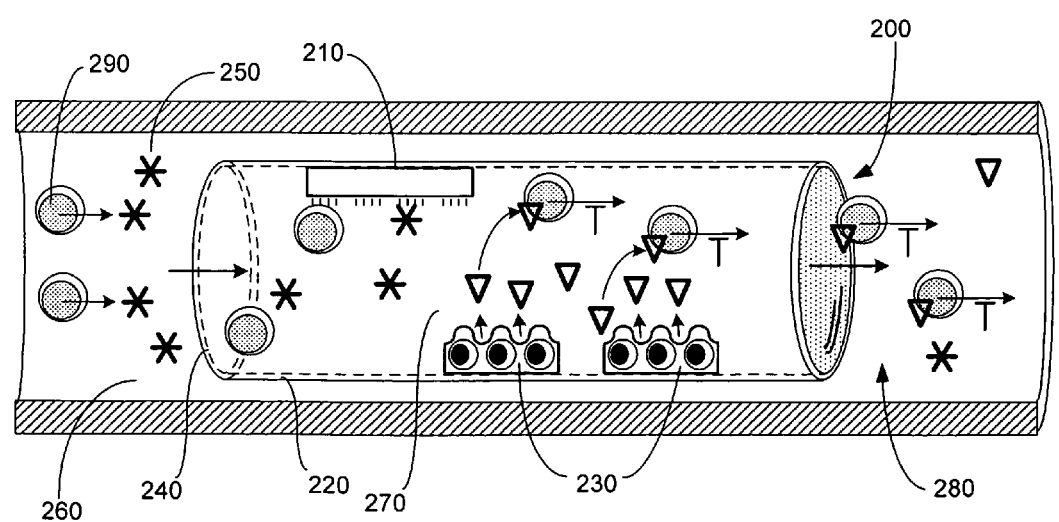

Continuing to refer to FIGS. 2A and 2B, depicted is a partial diagrammatic view of an illustrative embodiment of a device 200 including a sensor 210 configured to detect one or more inflammatory mediators 250 in peripheral blood 260 of a subject and configured to control levels of the one or more inflammatory mediators to a target value, and a treatment chamber 220 including one or more reactive components 230 configured to alter a functional structure of the one or more inflammatory mediators 250 in the peripheral blood of the subject. In FIG. 2A, the device can further include a controller 240 in communication with and responsive to the sensor 210 and configured to control access to the treatment chamber 220 by the peripheral blood 260. The one or more reactive component can further include a diffusible agent 270 to bind a precursor or inflammatory modulator 290 and/or inhibit synthesis of the one or more inflammatory mediators 250. The one or more reactive components 230 include, but are not limited to, a denaturing agent, a degradative agent, or an energy source, which can destroy, degrade, denature the one or more inflammatory mediators 250 or destroy an activity of the one or more inflammatory mediators. The device includes the sensor configured to detect a site having an elevated level of, the inflammatory mediators. The device can be targeted to a site having elevated levels in order to reduce the concentration of inflammatory mediators at one or more sites of inflammation 280 in the subject.

In FIG. 2B, the device can further include a controller 240 in communication with and responsive to the sensor 210 and configured to control access to the treatment chamber 220 by the peripheral blood 260. The one or more reactive component can further include an encapsulated cell that produces a diffusible agent 270 configured to bind a precursor 290 and/or inhibit synthesis of the one or more inflammatory mediators 250 and configured to alter a functional structure of the one or more inflammatory mediators. In an aspect, the reactive component can include an encapsulated cell that produces a diffusible agent 270 configured to bind to the one or more inflammatory mediators 250 and configured to alter a functional structure of the one or more inflammatory mediators. The one or more reactive components 230 include, but are not limited to, a denaturing agent, a degradative agent, or an energy source, which can destroy, degrade, denature the one or more inflammatory mediators 250 or destroy an activity of the one or more inflammatory mediators. The device is configured to reduce the concentration of inflammatory mediators at one or more sites of inflammation 280 in the subject.

Figure 3A:
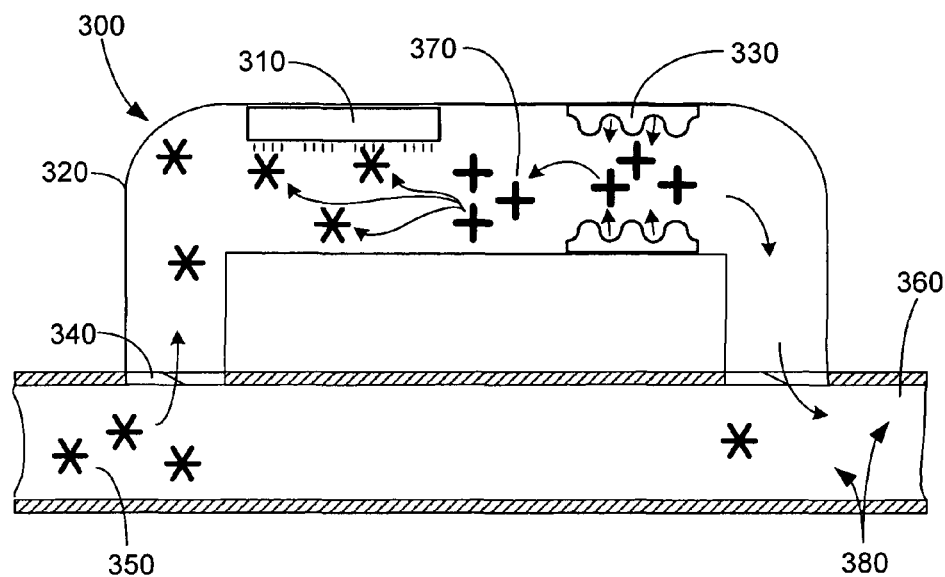
FIGS. 3A and 3B depict a diagrammatic view of an aspect of an exemplary embodiment of an extracorporeal device.
Figure 3B:
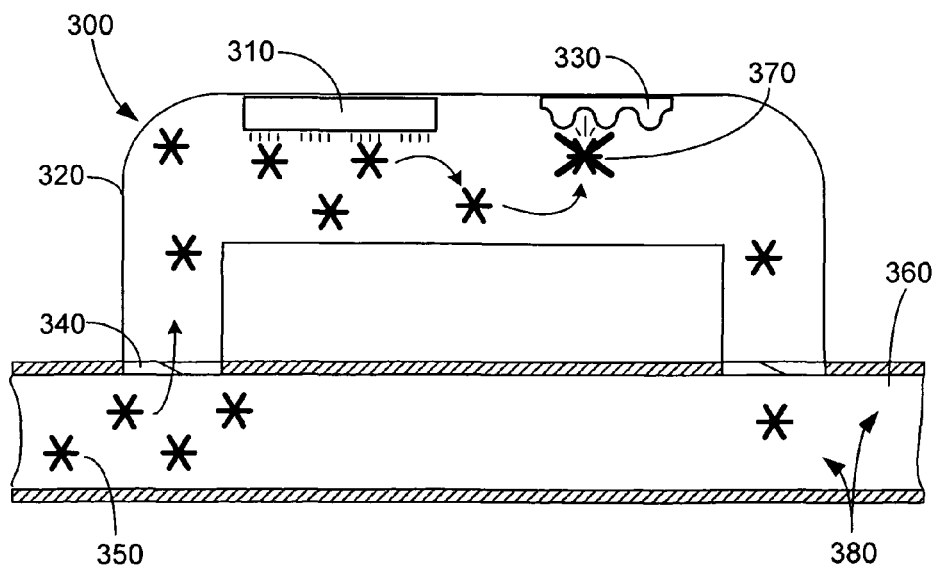

Continuing to refer to FIGS. 3A and 3B, depicted is a partial diagrammatic view of an illustrative embodiment of a device 300 including a sensor 310 configured to detect one or more inflammatory mediators 350 in peripheral blood 360 of a subject and configured to control levels of the one or more inflammatory mediators to a target value, and a treatment chamber 320 including one or more reactive components 330 configured to alter a functional structure of the one or more inflammatory mediators 350 in the peripheral blood of the subject. The device is outside the peripheral blood vessel of the subject and can be configured as an extracorporeal device.

In FIG. 3A, the device 300 can further include a controller 340 in communication with and responsive to the sensor 310 and configured to control access to the treatment chamber 320 by the peripheral blood 360. The reactive component 330 can further include a diffusible component 370 to bind the one or more inflammatory mediators 350 and configured to alter a functional structure of the one or more inflammatory mediators. The one or more reactive components 330 or the diffusible component 370 include, but are not limited to, a denaturing agent, a degradative agent, or an energy source, which can destroy, degrade, denature the one or more inflammatory mediators 350 or destroy an activity of the one or more inflammatory mediators. The device is configured to reduce the concentration of inflammatory mediators at one or more sites of inflammation 380 in the subject.

In FIG. 3B, the device 300 can further include a controller 340 in communication with and responsive to the sensor 310 and configured to control access to the treatment chamber 320 by the peripheral blood 360. The reactive component 330 can further include an affinity binding component 370 to bind the one or more inflammatory mediators 350 and configured to alter a functional structure of the one or more inflammatory mediators. The one or more reactive components 330 include, but are not limited to, a denaturing agent, a degradative agent, or an energy source, which can destroy, degrade, denature the one or more inflammatory mediators 350 or destroy an activity of the one or more inflammatory mediators. The device is configured to reduce the concentration of inflammatory mediators at one or more sites of inflammation 380 in the subject.

Figure 4:
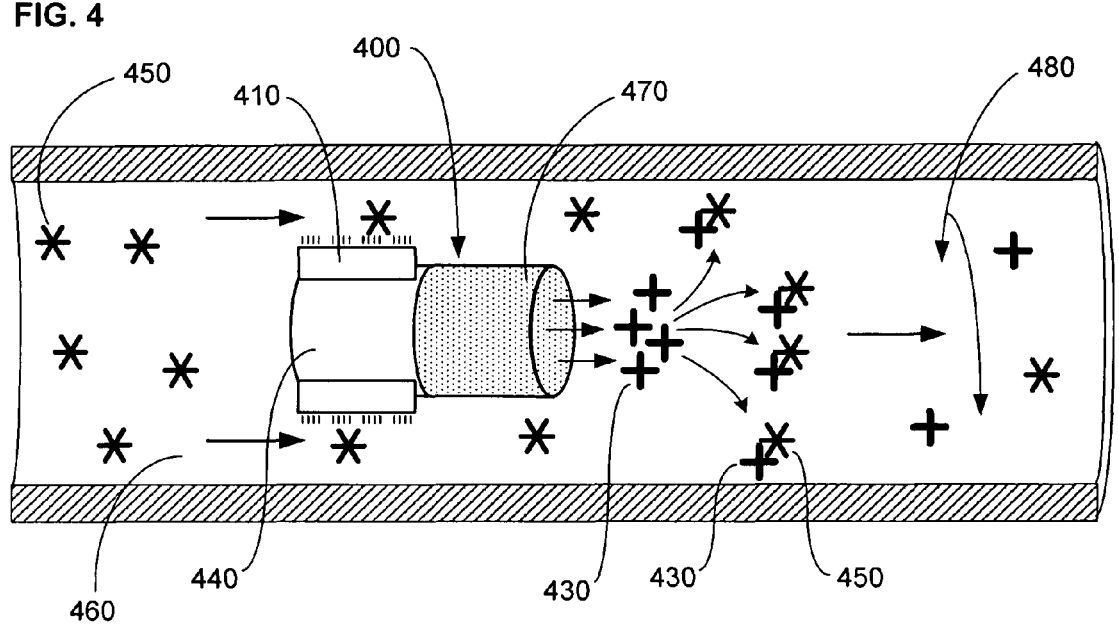
FIG. 4 depict a diagrammatic view of an aspect of an exemplary embodiment of an intracorporeal device.

Continuing to refer to FIG. 4, depicted is a partial diagrammatic view of an illustrative embodiment of a device 400 including a sensor 410 configured to detect one or more inflammatory mediators 450 in peripheral blood 460 of a subject and configured to control levels of the one or more inflammatory mediators to a target value, and a reservoir 470 including one or more reactive components 430 configured to alter a functional structure of the one or more inflammatory mediators 450 in the peripheral blood of the subject. The device can further include a controller 440 in communication with and responsive to the sensor 410. The reactive component 430 can further include a diffusible component to bind the one or more inflammatory mediators 450 and configured to alter a functional structure of the one or more inflammatory mediators. The one or more reactive components 430 include, but are not limited to, a denaturing agent, a degradative agent, or an energy source, which can destroy, degrade, denature the one or more inflammatory mediators 450 or destroy an activity of the one or more inflammatory mediators. The device can be configured to reduce the concentration of inflammatory mediators at one or more sites of inflammation 480 in the subject, or throughout the peripheral blood.

Figure 5:
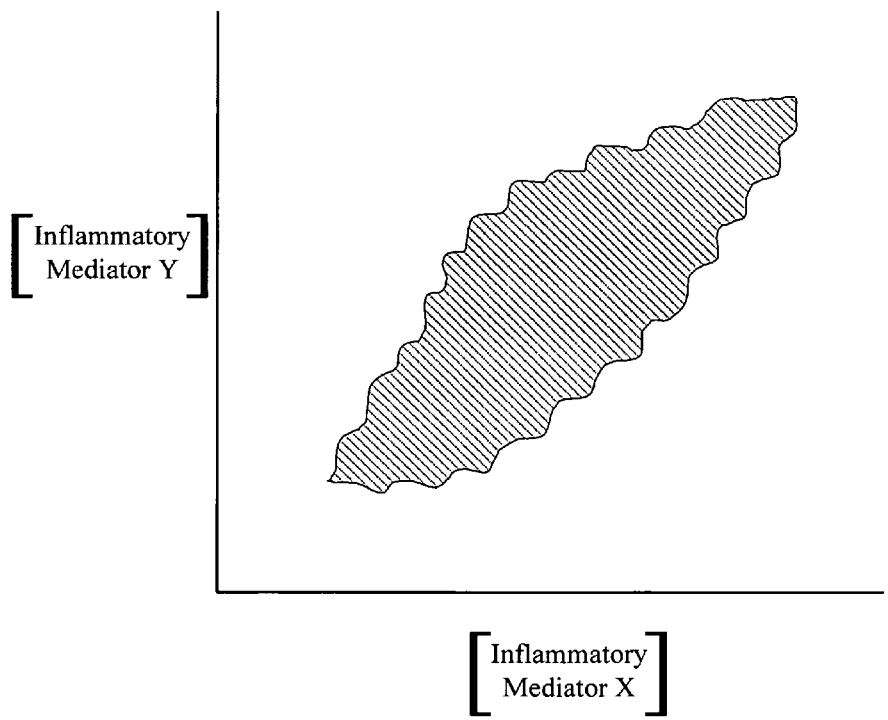
FIG. 5 depict a diagrammatic view of an aspect of an exemplary embodiment of a device.

Referring to FIG. 5, depicted is a partial diagrammatic view of an illustrative embodiment of a device including a sensor configured to detect one or more inflammatory mediators in peripheral blood of a subject and configured to control levels of the one or more inflammatory mediators to a target value, and a treatment chamber responsive to output from the sensor and configured to receive the peripheral blood through a flow route, the treatment chamber including one or more reactive components configured to alter a functional structure of the one or more inflammatory mediators in the peripheral blood of the subject. In an aspect, the target value includes a desired concentration of the one or more inflammatory mediators in the peripheral blood, or the target value includes a desired range of concentrations of the one or more inflammatory mediators in the peripheral blood. In a further aspect, the target value includes a desired ratio of concentrations of two or more inflammatory mediators in the peripheral blood. Or it can determine relative levels of the inflammatory mediators. The desired ratio of concentrations can be determined by any method or means, including for example, by a least squares fit of the concentrations of the two or more inflammatory mediators. For example, the desired ratio of concentrations can be determined by a least squares fit of the concentrations of the two or more inflammatory mediators at concentrations $x_1$, $x_2$, $x_3$, and $x_4$ for a first inflammatory mediator, X, and at concentrations $y_1$, $y_2$, $y_3$, and $y_4$ for a second inflammatory mediator, Y. The least squares can fit to a line or to a two or three dimensional space indicating the preferred ratio of the two or more inflammatory mediators.

Figure 6B:
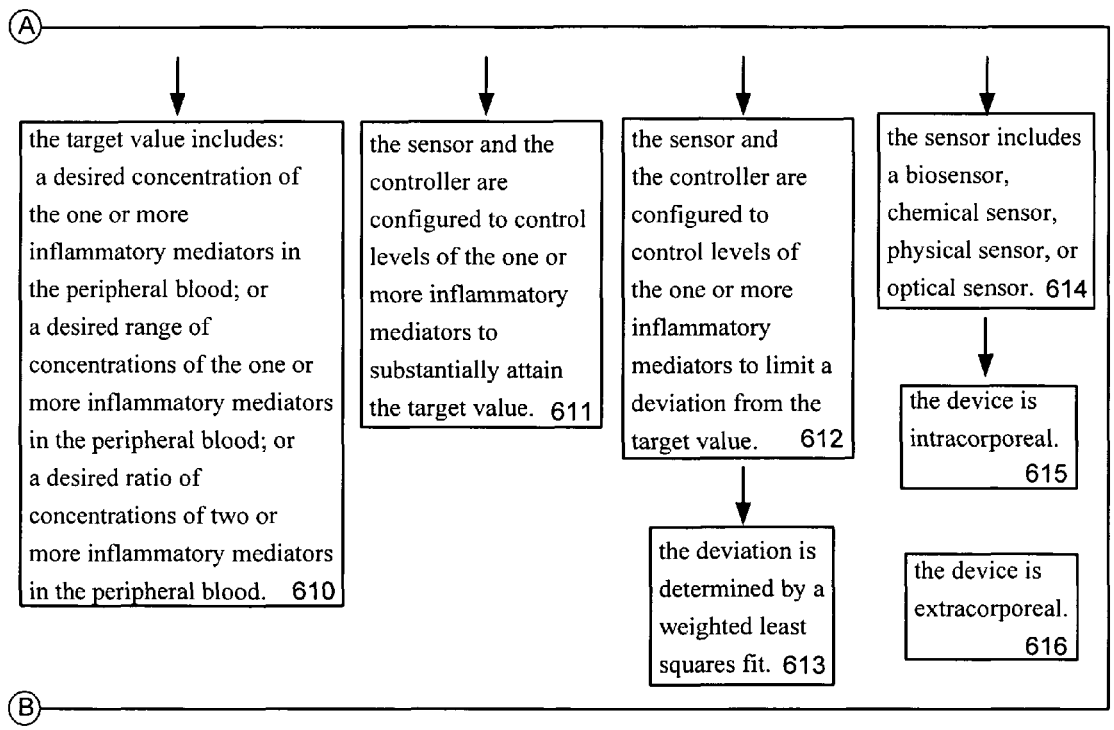
FIG. 6 depicts a logic flowchart of a method for a method for treating an inflammatory disease or condition in a subject.

Referring to FIG. 6, depicted is a logic flowchart of a method for treating an inflammatory disease or condition in a subject. The method 601 includes 602 providing a device configured to communicate with at least a portion of a peripheral blood of the subject, the device including a sensor configured to detect one or more inflammatory mediators in peripheral blood of a subject; a controller in communication with the sensor, a means for modulating a physiological effect of the one or more inflammatory mediators responsive to the controller, the controller configured to adjust the modulating means to achieve a target value of the detected one or more inflammatory mediators in the peripheral blood of the subject. The means for modulating a physiological effect of the one or more inflammatory mediators includes 604 a treatment chamber configured to receive at least a portion of the peripheral blood through a flow route, the controller configured to control flow of peripheral blood through the flow route into the treatment chamber, and the treatment chamber including one or more reactive components configured to alter a functional structure of the one or more inflammatory mediators in the peripheral blood. The means for modulating a physiological effect of the one or more inflammatory mediators includes 605 the controller configured to control interaction between one or more reactive components and the one or more inflammatory mediators, the one or more reactive components configured to alter a functional structure of the one or more inflammatory mediators in the peripheral blood.

Referring to FIG. 7, depicted is a logic flowchart of a method for treating an inflammatory disease or condition in a subject. The method 701 includes providing an extracorporeal device 702 including a treatment chamber configured to receive peripheral blood of the subject through a flow route, the treatment chamber including one or more reactive biological or chemical compounds that alter the functional structure of one or more inflammatory mediators in the peripheral blood. The method further includes 704 providing a sensor configured to detect the one or more inflammatory mediators in the peripheral blood. The method further includes 705 providing a controller in communication with the sensor and configured to adjust the one or more reactive biological or chemical compounds to achieve a target value of the detected one or more inflammatory mediators in the peripheral blood of the subject.

Controlling Levels of One or More Inflammatory Mediators to a Target Value

A device is described herein that includes a sensor configured to detect one or more inflammatory mediators in peripheral blood of a subject and configured to control levels of the one or more inflammatory mediators to a target value. As described above, the target value can be a desired concentration of one or more inflammatory mediators in the peripheral blood, or the target value can be a desired range of concentrations of one or more inflammatory mediators in the peripheral blood. Alternatively, the target value can be a desired ratio of concentrations of two or more inflammatory mediators in the peripheral blood. The desired ratio can be determined by a least squares fit of the concentrations of the two or more inflammatory mediators. The target value of an inflammatory mediator can be a desired concentration and/or concentration range and/or ratio of concentrations that is a specific value or range of values such as, for example, a value or range of values observed in a normal subject. Alternatively, the target value of an inflammatory mediator can be a desired concentration and/or concentration range and/or ratio of concentrations that is at least 20%, at least 40%, at least 60%, at least 80%, or at least 100% below or above the current level of the inflammatory mediator in the peripheral blood of a subject.

The target value of one or more inflammatory mediators can be a desired concentration and/or concentration range that is below that observed in the peripheral blood of a subject experiencing an inflammatory response, condition, disorder, or disease. A number of inflammatory mediators are elevated in the peripheral blood of subjects diagnosed with systemic immune response syndrome (SIRS) and sepsis. See, e.g., Ueda, et al., *Am. J. Respir. Crit. Care Med.* 160:132-136, 1999; Kurt, et al., *Mediators Inflamm.* 2007:31397, 2007; Kellum, et al., *Arch. Intern. Med.* 167:1655-1663, 2007; Wang, et al., *Crit. Care* 12:R106, 2008; which are incorporated herein by reference. One study compared the levels of TNF-α, IL-6, and IL-8 in normal subjects and subjects diagnosed with septic shock. In this study, the normal ranges of TNF-α, IL-6, and IL-8 were reported as less than 5 pg/ml, less than 10 pg/ml, and less than 10 pg/ml, respectively. In individuals with septic shock, the serum levels of TNF-α, IL-6, and IL-8 were significantly elevated to mean values of 138+/−22 pg/ml, 27,255+/−7,895 pg/ml, and 2,491+/−673 pg/ml, respectively. Ueda, et al., *Am. J. Respir. Crit. Care Med.* 160:132-136, 1999; which is incorporated herein by reference. As another example, a study described elevated serum levels of IL-1β in neonates diagnosed with sepsis versus IL-1β serum levels in normal neonates (41.2+/−13.6 pg/ml versus 10.4+/−2.7 pg/ml). In this same study the levels of TNF-α (21.0+/−9.4 pg/ml versus 4.6+/−1.5 pg/ml), IL-6 (196.9+/−74.1 pg/ml versus 8.2+/−5.8 pg/ml), and IL-8 (481.3+/−186.6 pg/ml versus 55.5+/−26.5 pg/ml) were also elevated in septic versus non-septic neonates. IL-10 is also present in elevated levels in the peripheral blood of subjects diagnosed with sepsis versus normal controls (39-100 pg/ml versus less than 10 pg/ml. Kurt, et al., *Mediators Inflamm.* 2007:31397, 2007; Kellum, et al., *Arch. Intern. Med.* 167: 1655-1663, 2007; which are incorporated herein by reference.

The relative levels of one or more inflammatory mediators in the peripheral blood of a subject may be correlated with prognosis and survival. For example, sepsis non-survivors have proportionally higher levels of inflammatory mediators relative to sepsis survivors and normal controls. In one study, high levels of both IL-10 and IL-6 are associated with increased mortality with a hazard ratio of 20.52. In this study, high initial serum levels of IL-10 (mean of 45 pg/ml) and IL-6 (mean of 735 pg/ml) upon admission to the emergency department were associated with development of severe sepsis and increased risk of death as compared with low initial levels of IL-10 (mean of 7.4 pg/ml) and IL-6 (mean of 15 pg/ml). Similarly, a second study demonstrated a direct correlation between sepsis symptom scores and the serum level of IL-6 and suggested that persistent elevation in IL-6 levels is predictive of poor outcome. These data suggest that modulating the levels of one or more inflammatory mediators to a desired target value in the peripheral blood may alter the course of the disease. See, e.g., Kellum, et al., *Arch. Intern. Med.* 167:1655-1663, 2007; Presterl, et al., *Am. J. Respir. Crit. Care Med.* 156:825-832, 1997; which are incorporated herein by reference.

In some instances, the target value of one or more inflammatory mediators may be a desired concentration and/or concentration range that is above that observed in the peripheral blood of a subject experiencing an inflammatory response, condition, disorder, or disease. For example, subjects with severe sepsis have decreased serum levels of gelsolin, a protein involved in severing and scavenging circulating filamentous actin. Studies have shown that actin may enhance major components of proinflammatory cytokine production, impair microcirculation and compromise multiple organs. Wang, et al., *Crit. Care* 12:R106, 2008, which is incorporated herein by reference. The normal level of gelsolin (126.8+/−32 mg/l) is depressed in non-septic critically ill subjects (52.3+/−20.3 mg/l) and further depressed in subjects diagnosed with severe sepsis (20.6+/−11.7 mg/l). In a further example, elevated levels of IL-10 in patients with acute coronary syndromes and elevated C-reactive protein are at reduced risk of death relative to similar patients with lower levels of IL-10. See, e.g., Heeschen, et al., *Circ.* 107: 2109-2114, 2003, which is incorporated herein by reference. In these instances, the desired target value may be higher than the level sensed in the peripheral blood of a subject experiencing an inflammatory response, condition, disorder, or disease.

Arthritis is a chronic inflammatory disease in which changes in the serum levels of various inflammatory mediators have been observed. For example, one study compared the mean levels of various inflammatory mediators in normal subjects versus subjects with rheumatoid arthritis including IL-6 (4.0 pg/ml versus 15.8 pg/ml), TNFα (3.2 pg/ml versus 10 pg/ml), IL-1β (57.3 pg/ml versus 129.8 pg/ml), IL-8 (2.6 μg/ml versus 9.3 μg/ml), IL-10 (4.6 μg/ml versus 15.5 μg/ml), and IL-12 (6.2 pg/ml versus 20.2 pg/ml). Psoriatic arthritis is also characterized by increased levels of circulating inflammatory mediators. Another study compared the levels of a number of cytokines, chemokines and growth factors in the serum of subjects diagnosed with psoriatic arthritis. Most notable were statistically significant increases in the serum levels of various inflammatory mediators in subjects diagnosed with psoriatic arthritis versus normal controls including IFN-α (38 pg/ml versus 8 pg/ml), IL-10 (14 pg/ml versus 11 pg/ml), IL-13 (11 pg/ml versus 8.5 pg/ml), EGF (80 pg/ml versus 32 pg/ml), VEGF (49 pg/ml versus 13 pg/ml), FGF (43 pg/ml versus 16 pg/ml) CCL3 (200 pg/ml versus 45 pg/ml) and CCL4 (140 pg/ml versus 50 pg/ml). The range of normal levels of each inflammatory mediator may vary. For example, in the first study, the levels of TNFα in normal subjects ranged from undetectable (0 pg/ml) to 7.3 pg/ml whereas the levels of IL-1β in normal subjects ranged from undetectable (0 pg/ml) to 265.5 pg/ml. See, e.g., Nowlan, et al., *Rheumatology*

45:31-37, 2006; Mittal & Joshi, *J. Indian Rheumatol. Assoc.* 10:59-60, 2002; Szodoray, et al., *Rheumatology* 46:417-425, 2007, which are incorporated herein by reference.

The target value can be a desired ratio of concentrations of two or more inflammatory mediators in the peripheral blood as determined by a least squares fit of the concentration values of the two or more inflammatory mediator. For example, a study assessed the levels of various inflammatory mediators in subjects with acute graft-versus-host disease (aGVHD) and observed significantly elevated levels of IL-5, IL-6 and IL-10. See, e.g., Fujii, et al., *Int. J. Mol. Med.* 17:881-885, 2006, which is incorporated herein by reference. The serum level ratios of IL-5/IL-2, IL-5/IL-4, IL-6/IL-4 were increased in subjects with aGVHD as compared to transplant subjects with no evidence of aGVHD. In this instance, the levels of one or more inflammatory mediators can be altered to modulate the overall ratio of two or more inflammatory mediators.

Ratios of other inflammatory mediators can be of value in understanding the types of immune cells activated in association with a disease condition. For example, the ratio of Th1/Th2 cytokines may be indicative of disease severity. Th1 type T-lymphocytes produce IL-2, IL-12, IFN$\gamma$, TNF$\alpha$ and TNF$\beta$ favoring cell mediated immune responses whereas Th2 type T-lymphocytes produce IL-4, IL-5, IL-6, IL-10, and IL-13 favoring humoral responses. The Th2 antibody mediated immune response predominates in subjects with sepsis as indicated by a significantly lower Th1/Th2 ratio in subjects with sepsis (median 0.46) as compared with non-septic control subjects (median 2.5) and is associated with decreased resistance to infection (see Andrews & Griffins *Brit. J. Nutr.* 87, Suppl 1:S3-S8, 2002, which is incorporated herein by reference). The ratio of two or more inflammatory mediators can be altered by altering the levels of one or more inflammatory mediators.

Intracorporeal Blood Processing

The device for altering the functional structure of one or more inflammatory mediators in the peripheral blood of a subject having an inflammatory disease or condition can include a device for intracorporeal treatment of the blood. Intracorporeal processing of the peripheral blood of a subject may be accomplished by inserting one or more devices into one or more intracorporeal locations of a subject. The intracorporeal device includes one or more sensors for sensing one or more inflammatory mediators. The intracorporeal device further includes means for controllably diverting all or part of the blood flowing in that part of the subject into one or more treatment chambers. The one or more treatment chambers can include specific binding agents for binding one or more specific inflammatory mediators. The one or more treatment chambers further include one or more reactive components to alter the functional structure of one or more inflammatory mediators. The intracorporeal device further includes a controller that receives sensed data, controls diversion of blood flow, and controls release of the one or more reactive components for altering the functional structure of one or more inflammatory mediators.

The intracorporeal device can be inserted into a blood vessel. The intracorporeal device may be a specialized stent fixed within a specific artery or vein. See, e.g., U.S. Patent Application 2007/0294150 A1, which is incorporated herein by reference. Alternatively, the intracorporeal device may be any of a number of biocompatible structures that may be placed in a blood vessel without impeding blood flow. See, e.g., U.S. Patent Application 2008/0058785 A1, which is incorporated herein by reference. Alternatively, the intracorporeal device may travel freely in the circulation as exemplified by a lumen traveling device. See, e.g., U.S. Patent Application 2007/0156211 A1, which is incorporated herein by reference. The device can target to a site of inflammation in the subject. The device can sense elevated levels of inflammatory mediators in the peripheral blood or lymphatic system of the subject and can target and form a stationary location at, or near, a site of inflammation in the peripheral circulation of the subject. In some aspects, the intracorporeal device may be incorporated into a shunt, for example, an arteriovenous shunt inserted between an artery and a vein. Alternatively, the intracorporeal device may be proximal to a blood vessel with controllable access to the blood flow through a conduit. As blood flows through or past the intracorporeal device, one or more inflammatory mediators may be sensed and the functional structure of the inflammatory mediator altered, e.g., antagonizing, inhibiting, binding, blocking, or downregulating the expression of a pro-inflammatory mediator, or agonizing, activating, or upregulating the expression of an anti-inflammatory mediator.

Extracorporeal Blood Processing

The device for altering the functional structure of one or more inflammatory mediators in the peripheral blood of a subject having an inflammatory disease or condition can include a device providing extracorporeal treatment of the blood. Extracorporeal processing of the peripheral blood of the subject may be accomplished by removing blood from the peripheral circulatory system to an extracorporeal device, altering the functional structure of one or more inflammatory mediators, and returning all or part of the processed blood back to the subject. The extracorporeal device includes one or more sensors for sensing one or more inflammatory mediators. The extracorporeal device further includes a mechanism for controllably diverting all or part of the blood flow into one or more treatment chambers. The one or more treatment chambers can include one or more reactive components, e.g., specific binding agents, for binding one or more specific inflammatory mediators. The one or more treatment chambers can further include one or more reactive components, e.g. degradative agents, binding agents, or energy sources, to alter the functional structure of the one or more inflammatory mediators. The extracorporeal device can further include a controller that receives sensed data, controls diversion of blood flow, and controls release of the one or more reactive components to alter the functional structure of one or more inflammatory mediators.

Blood may be removed from a subject. In typical high volume dialysis treatment, for example, blood is drawn from the arm through a fistula or graft between the radial artery and vein. Alternatively, blood may be removed from a vessel proximal to a critical organ such as for example the lungs, heart, kidney, and/or liver. For example, a large-bore central venous catheter may be used to access fluids in a vein near the heart or just inside the atrium. A Swan-Ganz catheter is a special type of catheter placed into the pulmonary artery.

Extracorporeal processing of a subject's blood to alter the functional structure of one or more inflammatory mediators may be accomplished using whole blood. Blood plasma is the liquid component of blood, in which the blood cells are suspended. It makes up about 55% of total blood volume. It is composed of mostly water (90% by volume), and contains dissolved proteins, glucose, clotting factors, mineral ions, hormones and carbon dioxide (plasma being the main medium for excretory product transportation). Blood plasma is prepared simply by spinning a tube of fresh blood in a centrifuge until the blood cells fall to the bottom of the tube. The blood plasma is then poured or drawn off. Blood serum is blood plasma without fibrinogen or the other clotting factors. Alternatively, extracorporeal processing of a subject's blood to alter the functional structure of one or more inflammatory mediators may be accomplished using one or more isolated fractions of whole blood. Whole blood may be fractionated into blood plasma and cellular blood components by centrifugation and/or membrane filtration using any of a number of in-line apheresis processes including, but not limited to, plasmapheresis, plasma exchange, plateletpheresis, and leukophoresis. Plasma substantially free of blood cells may be isolated by plasmapheresis in which the plasma is separated from the blood cells by centrifugation or filtration. The resulting plasma includes a number of protein components, including pro-inflammatory and anti-inflammatory mediators. The isolated plasma may be further processed by the extracorporeal device to alter the functional structure of one or more inflammatory mediators.

The plasma may be further fractionated using a form of hemodialysis and/or hemofiltration through a semi-permeable membrane or filter to include and/or exclude components of the plasma based on the relative size of the components. During hemodialysis, the blood from a subject flows in a path along one side of a membrane. A dialysate is circulated on the other side of the membrane and forms a concentration differential across the membrane. Liquid and other components carried in the blood are drawn by the concentration differential across the membrane and out of the blood. During hemofiltration, the blood from a subject flows in a path along a semipermeable membrane, across which a pressure difference exists. The pores of the membrane have a molecular weight cut-off that can pass liquid and components carried in the blood. The device can include one or more filters for selective removal of blood components in the molecular weight range into which most inflammatory mediators fall. See, e.g., U.S. Patent Application 2008/0110830 A1, Tetta, et al., *Kidney Int. Suppl.* 63: S69-S71, 2003 which are incorporated herein by reference. Many cytokines, for example, are relatively low molecular weight, electrically neutral proteins, ranging in size from about 8000 to about 30,000 daltons. Other inflammatory mediators may range in size from 5,000 to 150,000 daltons. One or more filters with varying molecular weight cut-offs may be used to filter the plasma. Whole blood may also be used for this purpose. The one or more filtrates containing one or more inflammatory mediators are passed into one or more treatment chambers of the device to alter the functional structure of the one or more inflammatory mediators.

Combined Intracorporeal and Extracorporeal Blood Processing

In some aspects, a combination of devices for intracorporeal and extracorporeal processing can be used to sense and/or alter the functional structure of one or more inflammatory mediators. For example, one or more intracorporeal devices can be used to sense in real-time the levels of one or more inflammatory mediators in the peripheral blood of a subject. Data regarding the levels of one or more inflammatory mediators in the blood of a subject can be transmitted wirelessly to an extracorporeal device that controllably initiates withdrawal of blood from the subject for processing. The extracorporeal device can further controllably initiate release and/or activation of one or more reactive components for altering the functional structure of one or more inflammatory mediators.

Sensors for Measuring Inflammatory Mediators in the Peripheral Blood

The device includes one or more sensors for qualitatively and/or quantitatively measuring one or more inflammatory mediators, e.g., pro-inflammatory or anti-inflammatory mediators, in the peripheral blood of a subject. The one or more sensors can include but are not limited to a biosensor, a chemical sensor, a physical sensor, an optical sensor, or a combination thereof. The one or more sensors can include one or more recognition elements that recognize one or more inflammatory mediators. The interaction of one or more inflammatory mediators with one or more sensors results in one or more detectable signals. Preferably the one or more sensors measure in real-time the levels of one or more inflammatory mediators in the peripheral blood of a subject.

The one or more sensors can sense one or more inflammatory mediators that are cytokines including, but not limited to, interferons (IFN) IFN-α, IFN-1β, and IFN-γ; interleukins (IL) IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); gelsolin, erythropoietin (EPO); and thrombopoietin (TPO). The one or more inflammatory mediators can be any of a number of chemotactic cytokines (chemokines) including but not limited to CC chemokines CCL1 through CCL28 exemplified by RANTES (CCL5), MCP-1 (CCL2), LARC (CCL20), MIP-1α (CCL3), and MDC (CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF. Other inflammatory mediators include but are not limited to anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF), TGF-β and VEGF; soluble receptors to tumor necrosis factor receptor (sTNFr); soluble interleukin receptors sIL-1r and sIL-2r; C-reactive protein; CD11b; histamine; serotonin; apolipoprotein A1; β2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins; and endotoxins such as lipopolysaccharide (LPS); and various exotoxins such as superantigens, e.g., from, *Staphylococcus aureus* and *Streptococcus pyogenes*.

The one or more recognition elements that can identify one or more inflammatory mediators in the blood can include, but are not limited to, antibodies, antibody fragments, peptides, oligonucleotides, DNA, RNA, aptamers, protein nucleic acids proteins, viruses, enzymes, receptors, bacteria, cells, cell fragments, inorganic molecules, organic molecules, or combinations thereof. The one or more recognition elements can be associated with one or more substrate integrated into the one or more sensors.

The one or more sensors for sensing one or more inflammatory mediators can incorporate one or more recognition elements and one or more measurable fluorescent signal. In an embodiment, one or more inflammatory mediators in the peripheral blood of a subject are captured by one or more recognition elements and further react with one or more fluorescent second elements. The fluorescence associated with the captured one or more inflammatory mediators can be measured using fluorescence spectroscopy. Alternatively, the fluorescence signal can be detected using at least one charged-coupled device (CCD) and/or at least one complimentary metal-oxide semiconductor (CMOS).

In an aspect, the one or more sensors can use Förster or fluorescence resonance energy transfer (FRET) to sense one or more inflammatory mediators in the peripheral blood of a subject. FRET is a distance-dependent interaction between the electronic excited states of two dye molecules in which excitation is transferred from a donor molecule to an acceptor molecule without emission of a photon. In some aspects, interaction of a donor molecule with an acceptor molecule may lead to a shift in the emission wavelength associated with excitation of the acceptor molecule. In other aspects, interaction of a donor molecule with an acceptor molecule may lead to quenching of the donor emission. The one or more recognition elements associated with the one or more sensors may include at least one donor molecule and at least one acceptor molecule. Binding of one or more inflammatory mediators to the recognition element may result in a conformation change in the recognition element, leading to changes in the distance between the donor and acceptor molecules and changes in measurable fluorescence. The recognition element may be a cell, an antibody, an aptamer, a receptor or any other molecule that changes conformation or signaling in response to binding one or more inflammatory mediators.

A variety of donor and acceptor fluorophore pairs may be considered for FRET associated with the recognition element including, but not limited to, fluorescein and tetramethylrhodamine; IAEDANS and fluorescein; fluorescein and fluorescein; and BODIPY FL and BODIPY FL. A number of Alexa Fluor (AF) fluorophores (Molecular Probes-Invitrogen, Carlsbad, Calif., USA) may be paired with other AF fluorophores for use in FRET. Some examples include, but are not limited, to AF 350 with AF 488; AF 488 with AF 546, AF 555, AF 568, or AF 647; AF 546 with AF 568, AF 594, or AF 647; AF 555 with AF594 or AF647; AF 568 with AF6456; and AF594 with AF 647.

The cyanine dyes Cy3, Cy5, Cy5.5 and Cy7, which emit in the red and far red wavelength range (>550 nm), offer a number of advantages for FRET-based detection systems. Their emission range is such that background fluorescence is often reduced and relatively large distances (>100 Å) can be measured as a result of the high extinction coefficients and good quantum yields. For example, Cy3, which emits maximally at 570 nm and Cy5, which emits at 670 nm, may be used as a donor-acceptor pair. When the Cy3 and Cy5 are not proximal to one another, excitation at 540 nm results only in the emission of light by Cy3 at 590 nm. In contrast, when Cy3 and Cy5 are brought into proximity by a conformation change in an aptamer, antibody, or receptor, for example, excitation at 540 nm results in an emission at 680 nm. Semiconductor quantum dots (QDs) with various excitation/emission wavelength properties may also be used to generate a fluorescence based sensor.

Quenching dyes may be used as part of the binder element to quench the fluorescence of visible light-excited fluorophores. Examples include, but are not limited, to DABCYL, the non-fluorescing diarylrhodamine derivative dyes QSY 7, QSY 9 and QSY 21 (Molecular Probes, Carlsbad, Calif., USA), the non-fluorescing Black Hole Quenchers BHQ0, BHQ1, BHQ2, and BHQ3 (Biosearch Technologies, Inc., Novato, Calif., USA) and Eclipse (Applera Corp., Norwalk, Conn., USA). A variety of donor fluorophore and quencher pairs may be considered for FRET associated with the recognition element including, but not limited to, fluorescein with DABCYL; EDANS with DABCYL; or fluorescein with QSY 7 and QSY 9. In general, QSY 7 and QSY 9 dyes efficiently quench the fluorescence emission of donor dyes including blue-fluorescent coumarins, green- or orange-fluorescent dyes, and conjugates of the Texas Red and Alexa Fluor 594 dyes. QSY 21 dye efficiently quenches all red-fluorescent dyes. A number of the Alexa Fluor (AF) fluorophores (Molecular Probes-Invitrogen, Carlsbad, Calif., USA) may be paired with quenching molecules as follows: AF 350 with QSY 35 or DABCYL; AF 488 with QSY 35, DABCYL, QSY7 or QSY9; AF 546 with QSY 35, DABCYL, QSY7 or QSY9; AF 555 with QSY7 or QSY9; AF 568 with QSY7, QSY9 or QSY21; AF 594 with QSY21; and AF 647 with QSY 21.

The one or more sensor for sensing one or more inflammatory mediators can use the technique of surface plasmon resonance (for planar surfaces) or localized surface plasmon resonance (for nanoparticles). Surface plasmon resonance involves detecting changes in the refractive index on a sensor surface in response to changes in molecules bound on the sensor surface. The surface of the sensor may be a glass support or other solid support coated with a thin film of metal, for example, gold. The sensor surface may further carry a matrix to which is immobilized one or more recognition elements that recognize one or more inflammatory mediators. The one or more recognition elements that recognize one or more inflammatory mediators may be antibodies or fragments thereof, oligonucleotide or peptide based aptamers, receptors of inflammatory mediators or fragments thereof, artificial binding substrates formed by molecular imprinting, or any other examples of molecules and or substrates that bind inflammatory mediators. As blood or blood components from the subject passes by the sensor surface, one or more inflammatory mediators may interact with one or more recognition elements on the sensor surface. The sensor is illuminated by monochromatic light. Resonance occurs at a specific angle of incident light. The resonance angle depends on the refractive index in the vicinity of the surface, which is dependent upon the concentration of molecules on the surface. An example of instrumentation that uses surface plasmon resonance is the BIACORE system (Biacore, Inc.—GE Healthcare, Piscataway, N.J.) which includes a sensor microchip, a laser light source emitting polarized light, an automated fluid handling system, and a diode array position sensitive detector. See, e.g., Raghavan & Bjorkman *Structure* 3:331-333, 1995, which is incorporated herein by reference.

The one or more sensors can be one or more label-free optical biosensors that incorporate other optical methodologies, e.g., interferometers, waveguides, fiber gratings, ring resonators, and photonic crystals. See, e.g., Fan, et al., *Anal. Chim. Acta* 620:8-26, 2008, which is incorporated herein by reference. For example, reflectometric interference spectroscopy can be used to monitor in real-time the interaction of the inflammatory mediator interferon 2 with an anti-interferon 2 antibody. See, e.g., Piehler & Schreiber, *Anal. Biochem.* 289: 173-186, 2001, which is incorporated herein by reference.

The one or more sensors for sensing one or more inflammatory mediators can be one or more microcantilevers. A microcantilever can act as a biological sensor by detecting changes in cantilever bending or vibrational frequency in response to binding of one or more inflammatory mediators to the surface of the sensor. In an aspect the sensor can be bound to a microcantilever or a microbead as in an immunoaffinity binding array. In another aspect, a biochip can be formed that uses microcantilever bi-material formed from gold and silicon, as sensing elements. See, e.g. Vashist *J. Nanotech Online* 3:DO: 10.2240/azojono0115, 2007, which is incorporated herein by reference. The gold component of the microcantilever can be coated with one or more recognition elements which upon binding one or more inflammatory mediators causes the microcantilever to deflect. Aptamers or antibodies specific for one or more inflammatory mediators can be used to coat microcantilevers. See, e.g., U.S. Pat. No. 7,097,662, which is incorporated herein by reference. The one or more sensor can incorporate one or more methods for microcantilever deflection detection including, but not limited to, piezoresistive deflection detection, optical deflection detection, capacitive deflection detection, interferometry deflection detection, optical diffraction grating deflection detection, and charge coupled device detection. In some aspects, the one or more microcantilever can be a nanocantilever with nanoscale components. The one or more microcantilevers and/or nanocantilevers can be arranged into arrays for detection of one or more inflammatory mediators. Both microcantilevers and nanocantilevers can find utility in microelectomechnical systems (MEMS) and/or nanoelectomechanical systems (NEMS) associated with an extracorporeal or intracorporeal device.

The one or more sensor for sensing one or more inflammatory mediator can be a field effect transistor (FET) based biosensor. In this aspect, a change in electrical signal is used to detect interaction of one or more analytes with one or more components of the sensor. See, e.g., U.S. Pat. No. 7,303,875, which is incorporated herein by reference.

The one or more sensors for sensing one or more inflammatory mediators can incorporate electrochemical impedance spectroscopy. Electrochemical impedance spectroscopy can be used to measure impedance across a natural and/or artificial lipid bilayer. The sensor can incorporate an artificial bilayer that is tethered to the surface of a solid electrode. One or more receptor can be embedded into the lipid bilayer. The one or more receptors can be ion channels that open and close in response to binding of a specific analyte. The open and closed states can be quantitatively measured as changes in impedance across the lipid bilayer. See, e.g., Yang, et al., IEEE SENSORS 2006, EXCO, Daegu, Korea/Oct. 22-25, 2006, which is incorporated herein by reference.

The one or more sensors for sensing one or more inflammatory mediator can be cells that include one or more binding elements which when bound to one or more inflammatory mediator induces a measurable or detectable change in the cells. The cells may emit a fluorescent signal in response to interacting with one or more inflammatory mediators. For example, a bioluminescent bioreporter integrated circuit may be used in which binding of a ligand to a cell induces expression of reporter polypeptide linked to a luminescent response (U.S. Pat. No. 6,673,596, [Durick & Negulescu *Biosens. Bioelectron.* 16:587-592, 2001] which are incorporated herein by reference. Alternatively, the one or more cell may emit an electrical signal in response to interacting with one or more inflammatory mediator. In a further aspect, an implantable biosensor may be used which is composed of genetically-modified cells that responded to ligand binding by emitting a measurable electrical signal. See U.S. Patent Application 2006/0234369 A1; which are incorporated herein by reference.

The device can further include one or more sensors for sensing one or more physiological parameters in the subject. Examples of physiological parameters include but are not limited to body temperature, respiration rate, pulse, blood pressure, edema, oxygen saturation, pathogen levels, or toxin levels.

Controller in Communication with and Responsive to a Sensor

The device can further include a controller that is in communication with and configured to be informed by the one or more sensors. The one or more sensors can transmit data to the controller regarding the detection or levels (relative or absolute) of one or more inflammatory mediators in the peripheral blood of a subject. The controller can be integrated to the extracorporeal or intracorporeal device. Alternatively, the controller can be a separate component of the device that receives and transmits data and/or commands either with or without wires. For example, an intracorporeal device can send data regarding the sensed levels of one or more inflammatory mediators to an external controller through a wireless signal.

The controller can compare the input data regarding the one or more inflammatory mediators in the blood of a subject with stored data. The controller itself can include the stored data. Alternatively, the controller can have access to one or more remote databases that include the stored data. The stored data may be data regarding the normal level of one or more inflammatory mediators in normal or healthy subjects without inflammatory conditions. The stored data may further include data regarding the baseline level of one or more inflammatory mediators in a subject prior to an inflammatory condition. The stored data may further include data regarding the level of one or more inflammatory mediators in a subject at one or more previous time points. The controller assesses the most recently obtained input data with the stored data and is configured to controllably initiate steps to alter the functional structure of one or more inflammatory mediators in the peripheral blood of a subject.

In response to input data, the controller can cause the device to controllably divert all or part of the blood of a subject into one or more treatment chambers. Access to one or more treatment chambers can be controlled by a flow-modulating element. A flow-modulating element may be a gate, a valve, a louver, a splitter or flow divider, a filter, a baffle, a channel restriction, a retractable iris, or other structure that controllably limits access of the blood flow to a treatment chamber. The controller can send a signal to the flow-modulating element indicating whether or not all or part of the flow of blood should be diverted into a treatment chamber.

The controller can further controllably initiate release or activation of one or more reactive components designed to alter the functional structure of one or more inflammatory mediators. The one or more reactive components can be controllably released or activated by the controller in the one or more treatment chambers of the device. In an aspect, the controller can release of one or more modulator into the peripheral blood of a subject to modulate the activity and/or expression of one or more inflammatory mediators. Alternatively, the controller can send data regarding the levels of one or more inflammatory mediators in the peripheral blood of a subject to the subject, to one or more third party individuals such as a physician or other caregiver, to a computing device, or to a combination thereof. The subject and/or caregiver or computing device can choose to initiate steps to alter the functional structure of one or more inflammatory mediators, to release modulators into the circulation, or a combination thereof.

The controller can also include one or more algorithms that provide computational models of inflammation. A computational model of inflammation may include information regarding, for example, a variety of interrelated signaling pathways involved in pro-inflammatory and anti-inflammatory processes. The computational model may further inform decisions made by the controller. See, e.g., U.S. Pat. No. 7,415,359 B2; U.S. Patent Applications 2007/0083333 A1, 2008/0201122 A1; Vodovotz, et al., *Curr. Opin. Crit. Care.* 10:383-390, 2004; Zenker, et al., *PLoS Comput. Biol.* 3(11): e204, 2007; Li, et al., *PLoS ONE* 3(7):e2789, 2008; Vodovotz, et al., *PLoS Comput. Biol.* 4:e1000014, 2008; An, *Theoretical Biology Medical Modeling* 5:11, 2008, each of which is incorporated herein by reference.

Device Including One or More Reactive Components

A device is disclosed that includes a means for modulating a physiological effect of one or more inflammatory mediators in the peripheral blood of a subject. The means for modulating the physiological effect can include, for example, one or more reactive components that are used to alter the functional structure of one or more inflammatory mediators in the peripheral blood of the subject. In a further aspect, the one or more reactive components can be used to alter the functional structure of one or more elements of one or more inflammatory signaling pathway. A reactive component includes, but is not limited to, a denaturing agent, a degradative agent, a binding agent, an energy source, or a combination thereof. A reactive component can further include a modulator that modulates the activity of one or more inflammatory mediators. The one or more reactive components are incorporated into or released within one or more treatment chambers associated with the device. Alternatively, the one or more reactive components are diffusible components released from a reservoir of the device into the peripheral blood of the subject.

The device includes one or more reactive component that can modulate the physiological effect of one or more inflammatory mediators, e.g., alter the functional structure of the one or more inflammatory mediators. The one or more inflammatory mediators can be cytokines, including but not limited to, interferons (IFN) IFN-α, IFN-β, and IFN-γ; interleukins (IL) IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-27, IL-28, IL-29, IL-30, IL-31, and IL-32; tumor necrosis factor (TNF) TNF-α and TNF-β; granulocyte colony stimulating factor (G-CSF); granulocyte-macrophage colony stimulating factor (GM-CSF); macrophage colony-stimulating factor (M-CSF); erythropoietin (EPO); and thrombopoietin (TPO). The one or more inflammatory mediators can be any of a number of chemotactic cytokines (chemokines) including, but not limited to, CC chemokines CCL1 through CCL28 exemplified by RANTES (CCL5), MCP-1 (CCL2), LARC(CCL20), MIP-1α (CCL3), and MDC(CCL22); CXC chemokines CXCL1 through CXCL17 exemplified by LIX (CXCL5), GCP-2 (CXCL6) and BCA-1 (CXCL13); C chemokines XCL1 and XCL2; CX3C chemokine C3CL1 (fractalkine); and chemokine like molecules exemplified by MIF. Other inflammatory mediators include but are not limited to anaphylatoxin fragments C3a, C4a, and C5a from the complement pathway; leukotrienes LTA4, LTB4, LTC4, LTD4, LTE4, and LTF4; prostaglandins; growth factors EGF, FGF-9, FGF-basic, growth hormone, stem cell factor (SCF); TGF-β and VEGF; soluble receptors to tumor necrosis factor receptor (sTNFr); soluble interleukin receptors sIL-1 r and sIL-2r; C-reactive protein; CD11b; histamine; serotonin; apolipoprotein A1; β2-microglobulin; bradykinin; D-dimer; endothelin-1; eotaxin; factor VII; fibrinogen; GST; haptoglobin; IgA; insulin; IP-10; leptin; LIF; lymphotactin; myoglobin; OSM; SGOT; TIMP-1; tissue factor; VCAM-1; VWF; thromboxane; platelet activating factor (PAF); immunoglobulins; and endotoxins such as lipopolysaccharide (LPS); and various exotoxins such as superantigens, e.g., from *Staphylococcus aureus* and *Streptococcus pyogenes*.

In some aspects, the device including the one or more reactive components can modulate the physiological effect, e.g., alter the functional structure, of one or more elements of one or more inflammatory signaling pathways. For example, activation of Toll-like receptors (TLRs) or IL-1 receptor can induce inflammation in immune cells via shared signaling cascades. TLRs are expressed in or on monocytes, macrophages, dendritic cells and microglia. TLRs recognize and respond to pathogen-associated molecular patterns (PAMPs) such as lipopolysaccharide, lipoteichoic acid, DNA with non-methylated cytosine-guanine motifs, zymosan, and/or viral double-stranded RNA. The TLR family members and the IL-1 receptor have a unique intracellular Toll/IL-1 receptor signaling domain which in response to activation, transduces the signal to a family of IL-1 receptor-associated kinases (IRAK). Phosphorylation of IRAK induces cascades of signaling through tumor necrosis factor receptor-associated factor 6 which, in turn, transduces the signal to IκB kinase-β and to mitogen-activated protein kinase. This signaling results in transcriptional responses, mediated primarily by nuclear factor-κB, extracellular-signal regulated kinase and stress-activated protein kinases, such as c-Jun N-terminal kinase (JNK) and p38, leading to expression of proinflammatory cytokines. One or more reactive components of the device can modulate the activity of one or more elements of this or other inflammatory signaling pathways. Extensive examples of signaling pathways associated with inflammation and other cellular processes may be accessed in the scientific literature and/or through a database, for example, Database of Cell Signaling (see, e.g., Goeddel & Chen, Tumor Necrosis Factor Pathway. Sci. Signal. Connections Map in the Database of Cell Signaling, as seen 6 Nov. 2008; CMP_7107; "TNF-R1 Signaling: A Beautiful Pathway" Chen & Goeddel *Science* 296: 1634-1635, 2002) and/or the UCSD-Nature Signaling Gateway (see, e.g., *Nat. Cell Biol.* 6: 1, 2004; each of which is incorporated herein by reference.

Binding Agents Remove One or More Inflammatory Mediators from the Peripheral Blood.

The device can include one or more reactive components that are binding agents designed to remove one or more inflammatory mediators from the peripheral blood of a subject. The one or more binding agents can be used alone to selectively or non-selectively sequester one or more inflammatory mediators. Alternatively, the one or more binding agents can be used to capture one or more inflammatory mediators in combination with treatment including one or more additional reactive components, e.g., a denaturing agent, a degradative agent, a modulator, an energy source, or a combination thereof. Following binding of the one or more inflammatory mediators to the one or more binding agents in a treatment chamber, one or more additional reactive components can be provided to alter the functional structure of the one or more inflammatory mediators.

The one or more binding agents can include absorbent material that non-selectively binds one or more inflammatory mediators. The absorbent material may include, but is not limited to, silica, activated charcoal, nonionic or uncharged resins or polymers, ionic or charged resins or polymers, anion exchange resins or polymers, cation exchange resins or polymers, neutral exchange resins or polymers, immobilized polymyxin B, immobilized monoclonal antibodies, immobilized inflammatory mediator receptors, immobilized specific antagonists, cellulose, cellulose derivatives, synthetic materials, polysulfone, polyacrylonitrile, polymethylmethacrylate, polyvinyl-alcohol, polyamide, polycarbonate, polystyrene-derivative fibers, and any combination thereof. Specific examples of absorbent materials that have been used in animal and clinical studies for non-specific binding of inflammatory mediators include, but are not limited to, polystyrene-divinylbenzene copolymer beads with biocompatible polyvinylpyrrolidone coating (CYTOSORB, MedaSorb Corporation, N.J., USA) and 2-methacryloyloxyethyl phosphorylcholine (MPCF-X; see, e.g., Nakada, et al., *Transfus. Apher. Sci.* 35:253-264, 2006, which is incorporated herein by reference.

The one or more binding agents can selectively bind one or more inflammatory mediators. A selective binding agent of one or more inflammatory mediators can include, but is not limited to, an antibody or fragments thereof, an oligonucleotide or peptide based aptamer, an inflammatory mediator receptor or parts thereof, an artificial binding substrate formed by molecular imprinting, or other examples of biomolecules and or substrates that bind inflammatory mediators.

The one or more binding agents can include one or more antibodies that bind one or more inflammatory mediators. Antibodies or fragments thereof for use as one or more binding agents of inflammatory mediators may include, but are not limited to, monoclonal antibodies, polyclonal antibodies, Fab fragments of monoclonal antibodies, Fab fragments of polyclonal antibodies, $Fab_2$ fragments of monoclonal antibodies, and $Fab_2$ fragments of polyclonal antibodies, chimeric antibodies, non-human antibodies, fully human antibodies, among others. Single chain or multiple chain antigen-recognition sites can be used. Multiple chain antigen-recognition sites can be fused or unfused. Antibodies or fragments thereof may be generated using standard methods. See, e.g., Harlow & Lane (*Antibodies: A Laboratory Manual*, Cold Spring Harbor Laboratory Press; $1^{st}$ edition 1988), which is incorporated herein by reference. Alternatively, an antibody or fragment thereof directed against one or more inflammatory mediators may be generated, for example, using phage display technology. See, e.g., Kupper, et al. *BMC Biotechnology* 5:4, 2005, which is incorporated herein by reference. An antibody, a fragment thereof, or an artificial antibody, e.g., Affibody® artificial antibodies (Affibody AB, Bromma, Sweden) can be prepared using in silico design (Knappik et al., *J. Mol. Biol.* 296: 57-86, 2000, which is incorporated herein by reference. In some aspects, antibodies directed against one or more inflammatory mediators may be available from a commercial source (from, e.g., Novus Biological, Littleton, Colo.; Sigma-Aldrich, St. Louis, Mo.; United States Biological, Swampscott, Mass.).

The one or more binding agents can include one or more aptamers that bind one or more inflammatory mediators. The aptamer can be an oligonucleotide RNA- or DNA-based aptamer. Aptamers are artificial oligonucleotides (DNA or RNA) that can bind to a wide variety of entities (e.g., metal ions, small organic molecules, proteins, and cells) with high selectivity, specificity, and affinity. Aptamers may be isolated from a large library of $10^{14}$ to $10^{15}$ random oligonucleotide sequences using an iterative in vitro selection procedure often termed "systematic evolution of ligands by exponential enrichment" (SELEX). See, e.g., Cao, et al., *Current Proteomics* 2:31-40, 2005; Proske, et al., *Appl. Microbiol. Biotechnol.* 69:367-374, 2005; Jayasena *Clin. Chem.* 45:1628-1650, 1999, which are incorporated herein by reference. In general, SELEX may be used to generate aptamers against inflammatory mediators, for example, cytokines and growth factors. See, e.g., Guthrie, et al., Methods 38:324-330, 2006, which is incorporated herein by reference. In an aspect, SELEX may be used to generate an RNA aptamer against the inflammatory mediator TNF-α. See, e.g., U.S. Pat. No. 7,309,789, which is incorporated herein by reference.

In an aspect, the one or more binding agents can include one or more aptamers that are peptide based aptamers. Peptide aptamers are artificial proteins in which inserted peptides are expressed as part of the primary sequence of a structurally stable protein. See, e.g., Crawford, et al., *Brief. Funct. Genomic Proteomic* 2:72-79, 2003, which is incorporated herein by reference. Peptide aptamers may be generated by screening an inflammatory mediator against yeast two-hybrid libraries, yeast expression libraries, bacterial expression libraries and/or retroviral libraries. Peptide aptamers may have binding affinities comparable to antibodies.

In a further aspect, the one or more binding agents can include one or more novel peptides. Novel peptides that bind selective targets may be generated, for example, using phage display methodologies. See, e.g., Spear, et al., *Cancer Gene Ther.* 8:506-511, 2001, which is incorporated herein by reference. In this aspect, the phage express novel peptides on the surface as fusion proteins in association with a phage major or minor coat protein and may be screened for binding interaction with one or more inflammatory mediators.

The one or more binding agents can include one or more inflammatory mediator receptors that bind one or more inflammatory mediators. All or part of an inflammatory mediator receptor may be used as a specific binding agent. Examples of inflammatory mediator receptors include, but are not limited to, type I cytokine receptors such as type 1 interleukin receptors, erythropoietin receptor, GM-CSF receptor, G-CSF receptor, growth hormone receptor, oncostatin M receptor, leukemia inhibitory factor receptor; type II cytokine receptors such as type II interleukin receptors, interferon-α/β receptors, interferon-γ receptor; many members of the immunoglobulin superfamily such as interleukin-1 receptor, CSF1, c-kit receptor, interleukin-18 receptor; tumor necrosis factor (TNF) receptor family such as TNF receptor 1 (TNF-R1), TNF receptor 2 (TNF-R2), CD27, CD40, and lymphotoxin β receptor; chemokine receptors including serpentine CCR and CXCR receptors, such as CCR1 and CXCR4, and interleukin-8 receptor; TGF β receptors such as TGF β receptor 1 and TGF β receptor 2. See Ozaki and Leonard, *J. Biol. Chem.* 277:29355-29358, 2002, which is incorporated herein by reference The one or more binding agents can include one or more artificial binding substrates for one or more inflammatory mediators formed by the process of molecular imprinting. In the process of molecular imprinting, a template is combined with functional monomers which upon cross-linking form a polymer matrix that surrounds the template. See Alexander, et al., *J. Mol. Recognit.* 19:106-180, 2006, which is incorporated herein by reference. Removal of the template leaves a stable cavity in the polymer matrix that is complementary in size and shape to the template. In an aspect, functional monomers of acrylamide and ethylene glycol dimethacrylate may be mixed with one or more inflammatory mediators in the presence of a photoinitiator and ultraviolet irradiation used to cross-link the monomers. The resulting polymer may be crushed or ground into smaller pieces and washed to remove the one or more inflammatory mediators, leaving a particulate matrix material capable of binding one or more inflammatory mediators. Examples of other functional monomers, cross-linkers and initiators may be used to generate an artificial binding substrate are provided. See, e.g., U.S. Pat. No. 7,319,038; Alexander, et al., *J. Mol. Recognit.* 19:106-180, 2006, which are incorporated herein by reference. In a further aspect, hydrogels may be used for molecular imprinting. See, e.g., Byrne et al., "Molecular imprinting within hydrogels", *Advanced Drug Delivery Reviews,* 54: 149-161, 2002, which is incorporated herein by reference. Other examples of synthetic binders are provided. See, e.g., U.S. Pat. Nos. 6,255,461; 5,804,563; 6,797,522; 6,670,427; and 5,831,012; and U.S. Patent Application 20040018508; and Ye and Haupt,

*Anal Bioanal Chem.* 378: 1887-1897, 2004; Peppas and Huang, *Pharm Res.* 19: 578-587 2002, which are incorporated herein by reference.

Reactive Components can Include Denaturing Agents that Alter the Functional Structure of One or More Inflammatory Mediators.

The device including one or more reactive components can include one or more denaturing agents. The functional structure of one or more inflammatory mediators can be altered by the process of denaturation in which the secondary, tertiary or quaternary structure of one or more inflammatory mediators are altered by denaturing agents. Examples of denaturing agents include, but are not limited to, acids such as acetic acid, trichloroacetic acid (TCA), sulfosalicyclic acid, picric acid; solvents such as methanol, ethanol, and acetone; cross-linking agents such as formaldehyde and gluteraldehyde; chaotropic agents such as urea, guanidinium chloride, and lithium perchlorate; and disulfide bond reducers such as 2-mercaptoethanol, dithiothreitol, and TCEP. In an aspect, acids may be used to denature a protein molecule by exposing the protein molecule to a pH below its isoelectric point. Under these conditions, the protein molecule will lose its negative charge and retain only positive charges. The like positive charges may repel one another and in areas of large charge density, the intramolecular repulsion may be sufficient enough to cause unfolding of the protein. The one or more denaturing agents may be incorporated into or released within one or more treatment chambers of the device. Alternatively, the one or more denaturing agents may be released by the device as diffusible agents into the peripheral blood.

Reactive Components can Include Degradative Agents that Alter the Functional Structure of One or More Inflammatory Mediators.

The functional structure of one or more inflammatory mediators can be altered by the one or more degradative agents that act by breaking peptide bonds within the primary amino acid sequence of the one or more inflammatory mediators. The one or more degradative agents can include any of a number of agents designed to cleave one or more peptide bonds of the primary amino acid sequence of one or more inflammatory mediators. Examples of degradative agents, include but are not limited to proteases, strong acids, strong bases, free radicals, natural or synthetic proteasomes, or photoactivatable agents. The one or more degradative agents may be incorporated into or released within one or more treatment chambers of the device. Alternatively, the one or more degradative agents may be released by the device as diffusible agents into the peripheral blood.

The device including one or more degradative agents can include one or more proteases. Examples of proteases include, but are not limited to, serine proteases, e.g., as trypsin, chymotrypsin, elastase, dipeptidyl peptidase IV, and subtilisin; cysteine proteases, e.g., papain, cathepsins, caspases, calpains; aspartic acid proteases, e.g., pepsin, renin, and HIV-proteases; metalloproteases, e.g. carboxypeptidases, aminopeptidases, and matrix metalloproteases, e.g. MMP1 through MMP28. The one or more proteases may be free in solution. Alternatively, the one or more proteases may be bound to a substrate. In an aspect, trypsin may be bound to glass beads. See, e.g., Lee, et al., *J. Dairy Sci.,* 58:473-476, 1974, which is incorporated herein by reference. Alternatively, trypsin and other proteases may be bound to an agarose matrix. Sources of immobilized proteases including trypsin and pepsin are available from commercial sources (Pierce Chemicals, Rockford, Ill.; Applied Biosystems, Foster City, Calif.).

The device including one or more degradative agents can include a natural or synthetic complex of proteases. In an aspect, the one or more inflammatory mediators may be subject to degradation using proteasomes. A proteasome is a naturally occurring large protein complex that contains multiple subunits. The complex includes several protease activities, for example, chymotrypsin-like activity, trypsin-like activity, glutamic acid protease activity, and threonine protease activity. Proteasome complexes may be purified from fractionated cells using ultracentrifugation through a 10-40% glycerol gradient. See, e.g., Pervan, et al., *Mol. Cancer Res.* 3:381-390, 2005, which is incorporated herein by reference. Proteasomes may be isolated using a commercially available isolation kit. (Proteasome Isolation Kit, Human 539176-1KIT, Calbiochem (EMD Chemicals, Inc.; Gibbstown, N.J.).

The device including one or more degradative agents can include an agent that selectively targets one or more inflammatory mediators for degradation. In an aspect, the one or more inflammatory mediators may be covalently tagged with ubiquitin for selective destruction by proteasomes. Ubiquitin is a small and highly conserved protein. An isopeptide bond links the terminal carboxyl of ubiquitin to the $\in$-amino group of a lysine residue of a protein targeted for degradation. The joining of ubiquitin to the targeted protein is ATP-dependent. Three enzymes are involved, designated E1, E2 and E3. Initially, the terminal carboxyl group of ubiquitin is joined in an ATP-dependent thioester bond to a cysteine residue on ubiquitin-activating enzyme (E1). The ubiquitin is then transferred to a sulfhydryl group on a ubiquitin-conjugating enzyme (E2). A ubiquitin-protein ligase (E3) then promotes transfer of ubiquitin from E2 to the $\in$-amino group of a lysine residue of a protein recognized by that E3, forming an isopeptide bond. There are distinct ubiquitin ligases with differing substrate specificity. In addition, some proteins have specific sequences termed a "destruction box" that is a domain recognized by a corresponding ubiquitin ligase. In general, E1, E2, and E3 may be isolated from natural sources or generated using standard molecular biology techniques and used to ubiquinate proteins in vitro. See, e.g., Chen, et al., *EMBO Rep.* 2:933-938, 2001, which is incorporated herein by reference. In some aspects, the E2 ligase may be genetically engineered in such a manner as to recognize a specific substrate. See, e.g., Colas, et al., *PNAS* 97:13720-13725, 2000, which is incorporated herein by reference. The device including the treatment chamber may further include one or more genetically engineered E2 ligase enzymes capable of adding ubiquitin to and facilitating degradation of the one or more inflammatory mediators in the peripheral blood of the subject.

In a further aspect, the ubiquitin may be indirectly associated with the one or more targeted inflammatory mediators. In an aspect, the ubiquitin may be linked to an antibody or an aptamer that specifically binds one or more inflammatory mediators. Binding of the ubiquitin-labeled antibody or aptamer to one or more inflammatory mediators may mark the protein conjugate for degradation by proteasomes.

The device including one or more degradative agents can include a strong acid. Acid hydrolysis may result in degradation of the one or more inflammatory mediators. In this aspect, strong acids such as hydrochloric acid or sulfuric acid may be used to break the carbon-nitrogen peptide bond. Degradation of one or more inflammatory mediators by acid hydrolysis may be optionally performed in combination with elevated temperature, a nitrogen atmosphere and or microwave energy.

The device including one or more degradative agents can include one or more free radical reactive oxygen species. Examples of reactive oxygen species include, but are not limited to, singlet molecular oxygen, superoxide ion, hydrogen peroxide, hypochlorite ion, hydroxyl radical. Reactive oxygen species can react directly with proteins, targeting peptide bonds or amino acid side chains. See, e.g., Davies, *Biochem. Biophys. Res. Commun.* 305:761-770, 2003, which is incorporated herein by reference. A number of the reactions mediated by reactive oxygen species lead to introduction of carbonyl groups into the protein which in turn may result in inactivation of the protein by cleavage of the peptide bound to yield lower-molecular weight products, cross-linking of proteins to yield higher-molecular weight products, or loss of catalytic function or structural function by distorting secondary and tertiary structure, or combination thereof. Reactive oxygen species may induce a amidation, diamide, glutamate oxidation and or proline oxidation which can lead to cleavage of peptide bonds. Reactive oxygen species may be formed by the interaction of biological molecules with components including, but not limited to, ionizing radiation, as a byproduct of cellular respiration, and dedicated enzymes such as NADPH oxidase and myeloperoxidase.

In an aspect, the device including one or more degradative agents can include reactive oxygen species that are singlet oxygen species. Singlet oxygen can cause damage to both the side-chains and backbone of amino acids, peptides, and proteins. See, e.g., Davies, *Biochem. Biophys. Res. Commun.* 305:761-770, 2003, which is incorporated herein by reference. Singlet oxygen species may react with tryptophan, tyrosine, histidine, methionine and or cysteine and cystine residues within a polypeptide and may cause increased susceptibility to proteolytic enzymes, an increased extent/susceptibility to unfolding, changes in conformation, an increase in hydrophobicity, and changes in binding of co-factor and metal ions. In particular, the interaction of tyrosine with singlet oxygen species may lead to fragmentation or cleavage of the polypeptide. See, e.g., Davies, *Biochem. Biophys. Res. Commun.* 305:761-770, 2003, which is incorporated herein by reference.

The device including one or more degradative agents can include one or more singlet oxygen species generated by a photosensitizer, a chemical which upon exposure to a given wavelength of light emits singlet oxygen species. Examples of photosensitizers include, but are not limited to, porphyrin derivatives such as Photofin, which is excited by red light at 630 nm; chlorins and bacteriochlorins such as bonellin (maximum absorbance 625 nm), mono-L-aspartyl chlorine e6 (max abs 654), m-tetrahydroxyphenyl chlorine (mTHPC, max abs 652 nm), and tin etiopurpurin (SnET2, maximum absorbance 660 nm); benzoporphyrin derivatives such as veteroporfin (also labeled BPD-MA, maximum absorbance 690 nm), 5-aminolaevulinic acid (ALA, porphoryin precursor to PpIX (maximum absorbance 635 nm)); texaphyrins such as lutetium texaphyrin (Lu-Tex, maximum absorbance 732), Phthalocyanines and naphthalocyanines (maximum absorbance 670-780 nm); and cationic photosensitizers such as rhodamine 123 and methylene blue. See, e.g., Prasad (2003) *Introduction to Biophotonics*, John Wiley & Sons, Inc. Hoboken, N.J. Tunable quantum dots (QDs), especially those absorbing in the wavelength range of 600 to 800 nm, also emit singlet oxygen species in response to light and may be useful as photosensitizers. See, e.g., Samia, et al. (2006) *Photochem. Photobiol.* 82:617-625, which is incorporated herein by reference.

Modulators can Alter the Functional Structure of One or More Inflammatory Mediators.

The device can include one or more reactive components that are one or more modulators that either directly or indirectly modulate the activity of one or more inflammatory mediators in the peripheral blood of a subject. The one or more modulators can be incorporated into or released within one or more treatment chambers of the device. Alternatively, the one or more modulators can be released by the device as diffusible agents into the peripheral blood. A modulator may alter, modify, reduce or eliminate the activity of one or more inflammatory mediators by preventing the binding of one or more inflammatory mediators to their respective cognates. Alternatively, a modulator may alter, modify, reduce or eliminate the activity of one or more inflammatory mediators by inhibiting the enzymatic activity, e.g., phosphorylation activity, of the one or more inflammatory mediators. Alternatively, the one or more modulators may indirectly alter, modify or eliminate the activity of one or more inflammatory mediators by attenuating the gene expression of one or more inflammatory mediators. In an aspect, the one or more modulators may indirectly alter or eliminate the activity of one or more inflammatory mediators by increasing the expression of endogenous antagonists of the one or more inflammatory mediators.

In an aspect, the one or more modulator can be a recombinant protein or peptide or polynucleotide configured to modulate, alter, modify, or reduce the activity of the one or more inflammatory mediators. The one or more modulator can be a polypeptide or nucleic acid molecule that either induces expression of one or more anti-inflammatory mediators or attenuates expression of one or more pro-inflammatory mediators. The one or more modulators can be a polypeptide or nucleic acid molecule that agonizes or antagonizes binding of one or more inflammatory mediators to its cognate. In an aspect, the one or more modulators may be an antibody or fragments thereof that block or modify the binding of an inflammatory mediator to its cognate. An example may be the chimeric monoclonal antibody infliximab (REMICADE® infliximab, Centocor Inc., Malvern, Pa.) that binds TNF-α and prevents it from binding to the TNF-α receptor. Alternatively, the one or more modulators may be all or part of one or more soluble receptors that bind one or more inflammatory mediators and compete for binding to the native receptors. An example may be etanercept, a soluble TNF-receptor (ENBREL® etanercept, Amgen, Thousand Oaks, Calif.). The one or more modulator may be an anti-inflammatory mediator. For example, one or more anti-inflammatory mediators may be released into the peripheral blood of a subject to counterbalance the effects of one or more pro-inflammatory inflammatory mediators. An example may be anakinra, a recombinant form of endogenous human IL-1 receptor antagonist (IL-1Ra; KINERET® anakinra, Amgen, Thousand Oaks, Calif.).

Other examples of modulators of inflammatory mediators that are proteins or peptides include, but are not limited to, adalimumab (anti-TNF antibody), abatacept (extracellular domain of cytotoxic T-lymphocyte-associated antigen 4, CTLA-4), alefacept (CD2 binding portion of leukocyte-function-associated antigen-3 (LFA3) fused to human IgG1), basiliximab and daclizumab (anti-IL-2 receptor alpha chain antibodies), efalizumab (anti-CD11a antibody), and recombinant forms of interferon-α, interferon-β, interferon-γ, and IL-2. In general, a modulator that is protein or peptide may be generated using standard recombinant molecular biology techniques, for example, using the corresponding cDNA sequences reported in GenBank as part of the National Center for Biotechnology Information (NCBI). See, e.g., Benson, et al., *Nucleic Acids Res.* 36:D25-D30, 2008, which is incorporated herein by reference. Antibodies to either an inflammatory mediator or its respective receptor may be generated using methods provided herein.

In an aspect, the reactive component can be a modulator that is a small molecule, an aptamer, or an inhibitory RNA, DNA, or nucleic acid. Modulators are contemplated that either directly or indirectly induce or attenuate expression of one or more inflammatory mediators and/or agonize or antagonize the activity of one or more inflammatory mediators. A small molecular inhibitor may inhibit a receptor or enzyme that is not itself an inflammatory mediator but is a component of the signaling pathway that modulates expression of one or more inflammatory mediators. For example, the small molecule thalidomide (THALOMID® thalidomide, Celgene Corporation, Summit N.J.) inhibits TNF-α synthesis while modulating the levels of IL-10 and IL-12.

Other examples of small molecule modulators include, but are not limited to, corticosteroids, e.g., hydrocortisone, cortisone, prednisone, prednisolone, methylprednisolone, meprednisone, triamcinolone, paramethasone, fluprednisolone, betamethasone, and dexamethasone; nonsteroidal anti-inflammatory drugs (NSAIDS), e.g., selective cycloxygenase (COX) inhibitors exemplified by celecoxib, etoricoxib, meloxicam, and valdecoxib and non-selective COX inhibitors exemplified by diclofenac, diflunisal, etodolac, fenoprofen, fluripofen, ibuprofen, indomethacin, ketoprofen, ketorolac, nabumetone, naproxen, oxaprozin, piroxicam, sulindac, tenoxica, tiaprofen, tolmetin, azapropazone, and carprofen; and disease modifying antirheumatic drugs (DMARDS), e.g., methotrexate, azathioprine, pennicillamine, hydroxychloroquine, chloroquine, cyclophosphamide, cyclosporine, mycophenolate mofetil, gold, and sulfasalazine.

In an aspect, the one or more modulators of inflammatory mediators can be a recombinant protein or peptide generated by one or more cells incorporated into the device. The one or more cells can be genetically modified to synthesize and secrete the one or more modulators. An extracorporeal device may deliver a therapeutic agent produced from cells. See, e.g., U.S. Patent Publication 2007/0269489 A1, which is incorporated herein by reference. Cells that may be used for this purpose include, but are not limited to, mammalian cells, enucleated cells (e.g., erythrocytes), plants cells, bacteria, or yeast. DNA sequences corresponding to one or more modulators are cloned into an appropriate cell type using standard procedures with appropriate expression vectors and transfection protocols. The genetically modified cells are encapsulated in one or more compartments of the blood processing device and secrete the one or more modulators into the peripheral blood of a subject. The genetically modified cells are kept separate from the circulation of a subject using a size-limiting biocompatible mesh or membrane filter, for example, that allows passage of the one or more modulator, but not the larger cells.

In an aspect, endogenous cells associated with an inflammatory response, condition, disorder, or disease can be used to synthesize and secrete one or more modulators. Examples of endogenous cells associated with an inflammatory response, condition, disorder, or disease include, but are not limited to, macrophages, dendrocytes, monocytes, T-lymphocytes, B-lymphocytes, neutrophils, eosinophils, basophils, and mast cells. In an aspect, the one or more modulators are released into the peripheral blood of the subject to interact with endogenous immune cells currently in circulation and to trigger synthesis and/or secretion of one or more other modulators from the circulating endogenous immune cells currently. In some aspects, the subject may be deficient in one or more types of endogenous immune cells during the course of an inflammatory reaction. At least one endogenous cell type associated with the immune response may be encapsulated in one or more compartments of the device where the cells may secrete one or more modulators into the peripheral blood of a subject in response to appropriate activators.

In some aspects, the one or more modulators are released from synthetic vesicles or particles. Examples include any of a number of drug delivery vehicles including, but not limited to, phospholipid vesicles (liposomes), nanoparticles, or hydrogels. The release of the one or more modulators can be triggered by binding of a specific target to the synthetic vesicle or particle. For example, one or more DNA aptamers may be incorporated into hydrogel and designed to bind one or more specific targets and release the contents of the hydrogel as described herein.

The device can include one or more reservoirs that store modulators of one or more inflammatory mediators and release the modulators into the treatment chamber and/or into the peripheral blood of the subject. Each reservoir can contain one or more modulators. Release of the one or more modulators from the one or more reservoirs into one or more treatment chambers and/or into the peripheral blood is controlled by the controller component of the device. In some aspects, the one or more modulators can be housed in multiple reservoirs associated with the device. For example, the device can include one or more microchips each with multiple reservoirs sealed with removable caps to enable controlled release of one or more inflammatory mediators. See, e.g., U.S. Pat. No. 7,413,846; Maloney & Santini, Proceedings 26th Annual International Conference IEEE EMBS, San Francisco, Calif., USA, Sep. 1-5, 2004, which is incorporated herein by reference.

Energy Sources can Alter the Functional Structure of One or More Inflammatory Mediators.

The device can include one or more reactive components that are one or more energy sources configured to alter the functional structure of one or more inflammatory mediators. The one or more energy sources can be directed to peripheral blood within the treatment chamber or can be directed outside the device to the peripheral blood. The one or more energy sources provide energy types including, but not limited to, electromagnetic radiation, e.g., ultraviolet, infrared, optical, microwave, or millimeter wave; acoustic energy, e.g., ultrasonic acoustic energy; heat; atmospheric pressure glow discharge; electron beam radiation; or gamma radiation. In some aspects, the energy source itself can alter the functional structure of one or more inflammatory mediators. Alternatively, heat generated by the energy source can alter the functional structure of one or more inflammatory mediators.

The application of one or more energy sources to the peripheral blood in the form of electromagnetic, acoustic, and or electronic energy can induce denaturation and or degradation of one or more inflammatory mediators. An energy source can denature an inflammatory mediator by unfolding the structure and/or inducing changes in amino acid chains and/or other side chains. The energy source can degrade an inflammatory mediator by cleaving one or more chemical bonds such as peptide bonds. The energy source can otherwise alter the functional structure of one or more inflammatory mediators by inducing aggregation of the one or more inflammatory mediators.

The device including the one or more energy sources can provide a set of differing energy inputs specifically directed to altering the functional structure of one or more inflammatory mediators. The set of differing energy inputs selectively resonates a plurality of resonant structures in the one or more inflammatory mediators and can alter the functional structure of one or more inflammatory mediators. See, e.g., U.S. Patent Application 2007/0021927 A1, which is incorporated herein by reference. The differing energy inputs are selected to resonate one or more resonant structures among the group of proximate atoms comprising the one or more inflammatory mediators. Application of a series of differing energy inputs can have a physical effect, such as transferring substantially more energy to a group of proximate atoms relative to other atoms in the surrounding medium, breaking a predetermined bond between two members of the group of proximate atoms, or changing a kinetic parameter of a reaction involving a member of the group of proximate atoms. The one or more resonant structures may be resonated simultaneously, sequentially, and/or in a temporally overlapping fashion. The series of differing energy inputs may be applied simultaneously, sequentially, and/or in a temporally overlapping fashion.

The set of differing energy inputs can be electromagnetic beams, each of which can have one or more characteristics including, but not limited to, a selected set of frequencies, a selected set of phases, a selected set of amplitudes, a selected temporal profile, a selected set of polarizations, or a selected direction. The temporal profile of the set of differing energy inputs may be characterized by a selected beam duration, and/or by a selected change in frequency, modulation frequency, phase, amplitude, polarization, or direction during a selected time interval. At least one electromagnetic beam may be polarized, amplitude modulated, or frequency modulated, and it may be, for example, an infrared beam. A plurality of electromagnetic beams may differ in frequency, modulation frequency, phase, amplitude, polarization, or direction, and/or may intersect at a target location. The method may include scanning at least one electromagnetic beam.

In an aspect, the device can include reactive components that include an energy field including, but not limited to, an electric field, a magnetic field, an electromagnetic field, a mechanical stress, a mechanical strain, a lowered or elevated temperature, a lowered or elevated pressure, a phase change, an adsorbing surface, a catalyst, an energy input, or a combination of any of these. The energy field can result in degradation of the one or more inflammatory mediators.

The device including the one or more energy sources can generate heat that induces denaturation of one or more inflammatory mediators. Exposure of most proteins or peptides to high temperature results in irreversible denaturation due to the weakening of long range bonds associated with tertiary structure and cooperative hydrogen bonds associated with helical structure. As these noncovalent bonds are broken, the protein molecule becomes more flexible and exposed to the solvent. Water molecules associated with the solvent form new hydrogen bonds that cannot be energetically overcome even as the protein molecule is cooled, leaving the protein molecule in an altered or denatured state. The one or more inflammatory mediators may be inactivated by treatment with a heat source. The heat source may be electrical, heating the entirety of the treatment chamber of the device. Alternatively, the heat source may heat a substrate of the device to which one or more inflammatory mediators are attached. Alternatively, the heat source may be more focused such as that experienced from exposure to focused electromagnetic energy, e.g. from a laser. In some aspects, focused electromagnetic energy may cause the substrate to bound to the one or more inflammatory mediator to heat. In an aspect, the one or more inflammatory mediators may bind to specific binding agents associated with one or more carbon nanotubes, the latter of which may emit heat in response to near infrared (NIR) radiation (Kam, et al., *PNAS* 102:11600-11605, 2005, which is incorporated herein by reference.

The device including the one or more energy sources can generate microwave energy for use in altering the functional structure of one or more inflammatory mediators. An energy source that incorporates microwave energy can result in degradation of the one or more inflammatory mediators. Microwaves are electromagnetic radiation with wavelengths between 0.01 and 1 meter and a frequency range between 0.3 and 30 GHz. The efficiency of microwave denaturation and/or degradation can be enhanced by including an acid, a protease, a chemical or combination thereof. The effects of microwave energy on peptide bond integrity can provide more that just rapid heating and suggests that some non-heat component of microwaves facilitates breakdown of the peptide bond. See, e.g., Lill, et al., *Mass. Spectrometry Rev.* 26:657-671, 2007, which is incorporated herein by reference.

The device including the one or more energy sources can generate focused ultrasound energy for use in altering the functional structure of one or more inflammatory mediators. Sonication in the form of focused ultrasound energy may result in degradation of the one or more inflammatory mediators. In an aspect, high intensity focused ultrasound produces cavitation bubbles that when collapsed yield very high localized pressures and high temperatures along with shear forces, jets and shock waves. The local increase in temperature and pressure can effectively denature proteins. See, e.g., Lopez-Ferrer, et al., *J. Proteome Res.* 7:3860-3867, 2008, which is incorporated herein by reference.

The device including the one or more energy sources can generate plasma by atmospheric dielectric-barrier discharge for use in altering the functional structure of one or more inflammatory mediators. Plasma generated by atmospheric dielectric-barrier discharge may result in degradation of the one or more inflammatory mediators. See, e.g., Hou, et al., *IEEE Transactions on Plasma Science* 36:1633-1637, 2008, which is incorporated herein by reference. Plasma is an ionized gas in which a certain proportion of the electrons are free rather than bound to an atom or molecule. The plasma may generated by a non-thermal discharge at atmospheric pressure by application of high voltages across small gaps. The atmospheric dielectric-barrier discharge may be scalable from one millimeter to one meter (Walsh, et al., *IEEE Transactions on Plasma Science* 36:1314-1315, 2008, which is incorporated herein by reference. A plasma jet and or a plasma brush may be used to degrade one or more inflammatory mediators.

The device including the one or more energy sources can generate high energy radiation for use in altering the functional structure of one or more inflammatory mediators. High energy radiation may result in degradation of the one or more inflammatory mediators. Gamma radiation in the range of about 2.0 kGy to about 23.0 kGy is able to denature protein in a dose dependent manner as determined by size chromatography. See, e.g., Vuckovic, et al., *J. Serb. Chem. Soc.* 70:1255-1262, 2005, which is incorporated herein by reference. Sources of gamma radiation that may be included in the device include but are not limited to cobalt-60, cesium-137, and technetium-99.

The device including the one or more energy sources can generate electron beam radiation for use in altering the functional structure of one or more inflammatory mediators. Electron beam radiation can result in degradation of the one or more inflammatory mediators. Electron beam energy of 92.9 kGy induces physical changes and loss of protein antigenicity (Katial, et al., *J. Allergy Clin. Immunol.* 110:215-219, 2002, which is incorporated herein by reference. A nanoscale electron beam generator may be devised from a network array structure of carbon nanotubes. See, e.g., U.S. Pat. No. 7,355,334, which is incorporated herein by reference.

Two or More Reactive Components can be Combined to Alter the Functional Structure of One or More Inflammatory Mediators.

The device can include two or more reactive components that have been combined to alter the functional structure of one or more inflammatory mediators. The two or more combined reactive components can be one or more binding agent combined with one or more denaturing agent, degradative agent, modulator, energy source, or combination thereof. For example, a binding agent, e.g., oligonucleotide aptamer, may be used to capture one or more inflammatory mediators in the treatment chamber of the device prior to treatment with a denaturing agent, degradative agent, modulator, energy source, or a combination thereof.

In an aspect, the two or more reactive components of the device can be incorporated into a single biomolecule. For example, the first reactive component can be a binding agent, e.g., an antibody, that includes a second reactive component that is a degradative activity. Certain antibodies are capable of cleaving the amide bond of peptide bonds. See, e.g., Janda, et al., *Science* 241:1188-1191, 1988; Lacroix-Desmazes, et al., *J. Immunol.* 177:1355-1365, 2006; Ponomarenko, et al., *PNAS,* 103:281-286, 2006; and U.S. Pat. No. 6,387,674, which are incorporated herein by reference. Alternatively, the first reactive component can be a binding agent, e.g., an antibody, and includes a second reactive component that is a reactive oxygen species. The one or more inflammatory mediators can bind to one or more binding agents that are catalytic antibodies capable of generating the reactive oxygen species $H_2O_2$ in response to UV radiation. See, e.g., Wentworth, et al., *Science* 293:1806-181811, 2001; Wentworth, *Science* 296:2247-2248, 2002; Wentworth, et al., *PNAS,* 97:10930-10935, 2000, which are incorporated herein by reference. One or more antibodies or other binding agents can be generated for both binding and degradation of one or more inflammatory mediators.

In another aspect, the two or more reactive components of the device can be incorporated into a single biomolecule and can include a first component that is a binding agent, e.g., an aptamer, and a second component that is a degradative agent, e.g., a protease. For example, one or more proteases may be conjugated or chemically linked to one or more oligonucleotide-based aptamers. The oligonucleotide-based aptamers are designed to bind one or more inflammatory mediators. Upon binding to the oligonucleotide-based aptamers, the one or more inflammatory mediators are brought into proximity to the one or more proteases resulting in proteolytic degradation of the one or more inflammatory mediators. Examples of proteases have been provided herein and may be linked to oligonucleotide-based aptamers using any of a number of methods for conjugating a polypeptide to an oligonucleotide. In a further aspect, a polypeptide protease may be conjugated to an oligonucleotide-based aptamer using a streptavidin-biotin bridge by introducing a biotinylated oligonucleotide into the aptamer sequence and linking it to a biotinylated protease through a streptavidin bridge. Alternatively, the polypeptide protease may be conjugated to the oligonucleotide-based aptamer using a thiol-maleimide linkage in which a carbon with an attached thiol group is placed on the aptamer and reacts with a maleimide group added to the C terminus of the protease. See, e.g., Nitin, et al., *Nucleic Acids Res.* 32:e58, 2004, which is incorporated herein by reference. A number of modified nucleotides are commercially available for use in synthesizing oligonucleotide aptamers with amines or other side chains for cross-linking (TriLink Biotechnologies, San Diego, Calif.; Sigma Aldrich, St. Louis, Mo.).

In a further aspect, the first reactive component can be a binding agent linked to a second reactive component encapsulated in a tunable vesicle. For example, the second reactive component, e.g., a denaturing and/or degradative agent, can be encapsulated in a tunable hydrogel. The binding of one or more inflammatory mediators to the first reactive component, e.g., binding agent, releases the denaturing and/or degradative agent from the hydrogel. In an aspect, target-responsive hydrogels may be generated in which the contents of the hydrogel are selectively released in response to binding a specific target. The hydrogel may incorporate one or more binding agents that are antibodies. The hydrogel may release its contents in response to an antibody-antigen interaction. See, e.g., Miyata, et al., *PNAS* 103:1190-1193, 2006, which is incorporated herein by reference. In an aspect, the target-responsive hydrogel may incorporate one or more binding agents that are oligonucleotide-based aptamers and release its contents in response to an aptamer-ligand interaction. See Yang, et al., *J. Am. Chem. Soc.* 130:6320-6321, 2008, which is incorporated herein by reference. In the latter case, two or more distinct aptamers configured to partially overlap during hybridization may be copolymerized into a polyacrylamide hydrogel. At least one of the two or more aptamers further binds to a specific target, e.g., an inflammatory mediator. When the inflammatory mediator binds to the aptamer, the number of nucleotide bases available for hybridization between the overlapping aptamers is reduced, causing them to separate. This separation allows the hydrogel to dissolute and release its contents. A target responsive hydrogel may be generated which incorporates aptamers that specifically recognize one or more inflammatory mediators. The hydrogel itself may be loaded with one or more proteases or other reactive components that are configured to alter the functional structure of inflammatory mediators. The contents of the hydrogel are released upon binding of the one or more inflammatory mediators to the aptamers associated with the hydrogel. In a further aspect, hydrogels may be used for molecular imprinting. See, e.g., Byrne et al., "Molecular imprinting within hydrogels," *Advanced Drug Delivery Reviews,* 54: 149-161, 2002, which is incorporated herein by reference.

Substrates for Reactive Components

The one or more reactive components including binding agents, denaturing agents, degradative agents, modulators, or combinations there of can be free in solution within one or more treatment chambers of the device. Alternatively, the one or more reactive components can be immobilized on a solid substrate within the one or more treatment chambers of the device. The solid substrate may be a matrix, e.g., a bead or filter, that is added to one or more treatment chambers of the device. Examples of applicable solid substrates include, but are not limited to, beads, particles, membranes, semi-permeable membranes, capillary, or microarrays. The solid substrate may be comprised of an inorganic material, e.g., glass, alumina, silica, silicon, zirconia, graphite, magnetite, semiconductors, or combinations thereof. Alternatively, the solid substrate may be comprised of an organic material, e.g., polysaccharides including agarose, dextran, cellulose, chitosan, and polyacrylamide, polyacrylate, polystyrene, polyvinyl alcohol, or combinations thereof. Alternatively, the one or more specific binding agents or one or more reactive components may be associated with a solid substrate that are cells, e.g., mammalian cells, enucleated erythrocytes, bacteria, or viral particles or vesicles such as liposomes or other micellular vesicles.

In some aspects, the one or more reactive components, either free in solution or bound to a solid substrate, can be prevented from leaving the one or more treatment chambers of the device either due to size exclusion using a filter or mesh or due to physical attachment to the device. In a detailed aspect, one or more inflammatory mediators present in the blood can bind to the one or more reactive components as the blood passes through the device and sequestered for inactivation. Alternatively, the one or more reactive components, either free in solution or bound to a solid substrate, can be released into the blood stream and allowed to bind one or more inflammatory mediators while in circulation. In this aspect, the one or more reactive components can be recaptured by the device and the functional structure of the one or more bound inflammatory mediators can be altered.

The one or more reactive components can be bound to the solid substrate either directly or indirectly. For example, the one or more reactive components may be coupled to the solid substrate by covalent chemical bonds between particular functional groups on the specific binding agent (e.g., primary amines, sulfhydryls, carboxylic acids, hydroxyls, and aldehydes) and reactive groups on the solid substrate. A variety of activating compounds and schemes for directly bonding ligands to solid substrates are known. Some examples include, but are not limited to, cyanogen bromide, cyanuric chloride, epichlorohydrin, divinyl sulphone, p-toluenesulphonyl chloride, 1,1'-carbonyldiimidazole, sodium metaperiodate, 2-fluoro-1-methylpyridiniumtoluene-4-sulphonate, glycidoxypropyl-trimethoxysilane and 2,2,2-trifluoroethanesulphonyl chloride. For example, cyanogen bromide in base reacts with hydroxyl (OH) groups on agarose solid substrate to form cyanate esters or imidocarbonates. These groups readily react with primary amines under mild conditions resulting in a covalent coupling of the ligand to the agarose solid substrate. Reactive imidocarbonates may also be formed on carbon nanotubes, for example, through reactive carboxyl groups generated by treatment of the nanotubes with oxidizing agents. See, e.g., Bianco, et al., in *Nanomaterials for Medical Diagnosis and Therapy*. pp. 85-142. Nanotechnologies for the Live Sciences Vol. 10 Edited by Challa S. S. R. Kumar, WILEY-VCH Verlag GmbH & Co. KGaA, Weinheim, 2007, which is incorporated herein by reference. Functionalization of silicon chips with carboxyl groups can be subsequently used to immobilize proteins in the presence of N-ethyl-N'-(3-dimethylaminopropyl)carbodiimide hydrochloride (EDC) and N-hydroxysuccinimide ester (NHS). See, e.g., Hu, et al., *Rapid Commun. Mass Spectrom.* 21:1277-1281, 2007, which is incorporated herein by reference.

The one or more reactive components may or may not have linking or spacer groups bound to the C-terminus which when present may be used to bind the specific binding agent to the solid substrate indirectly. When present the linking group may be a polymer or a monomer. A linking group may be a chain of from 1-10 amino acids. Other examples of linking groups include, but are not limited to, polyethylene glycol, polypropylene glycol, polyesters, polypeptides, polyethers, polysaccharides, glycidoxyalkyl, alkoxyalkyl, alkyl, glycidoxypropyl, ethyl, propyl, phenyl and methacryl; and silicon containing linking groups such as diethyl(triethoxysilylpropyl)malonate; 3-mercaptopropyltrimethoxysilane; 3-aminopropyltrimethoxysilane; N-[(3-trimethoxysilyl)propyl]ethylenediaminetriacetic acid; p-(chloromethyl) phenyltrimethoxysilane; vinyltriethoxysilane; 3-bromopropyltriethoxysilane; and 3-glycidoxypropyltrimethoxysilane.

In general, any of a number of homobifunctional, heterofunctional, and/or photoreactive cross linking agents may be used to conjugate one or more reactive components to an appropriately derivatized substrate. Examples of homobifunctional cross linkers include, but are not limited to, primary amine/primary amine linkers such as BSOCES ((bis(2-[succinimidooxy-carbonyloxy]ethyl)sulfone), DMS (dimethyl suberimidate), DMP (dimethyl pimelimidate), DMA (dimethyl adipimidate), DSS (disuccinimidyl suberate), DST (disuccinimidyl tartate), Sulfo DST (sulfodisuccinimidyl tartate), DSP (dithiobis(succinimidyl propionate), DTSSP (3,3'-dithiobis(succinimidyl propionate), EGS (ethylene glycol bis(succinimidyl succinate)) and sulfhydryl/sulfhydryl linkers such as DPDPB (1,4-di-(3'-[2'pyridyldithio]-propionamido) butane). Examples of heterofunctional cross linkers include, but are not limited to, primary amine/sulfhydryl linkers such as MBS (m-maleimidobenzoyl-N-hydroxysuccinimide ester), Sulfo MBS (m-maleimidobenzoyl-N-hydroxysulfosuccinimide), GMBS (N-gamma-maleimidobutyryl-oxysuccinimide ester), Sulfo GMBS (N-γ-maleimidobutyryloxysulfosuccinimide ester), EMCS (N-(epsilon-maleimidocaproyloxy)succinimide ester), Sulfo EMCS(N-(epsilon-maleimidocaproyloxy)sulfosuccinimide), SIAB (N-succinimidyl(4-iodoacetyl)aminobenzoate), SMCC (succinimidyl 4-(N-maleimidomethyl) cyclohexane-1-carboxylate), SMPB (succinimidyl 4-(rhomaleimidophenyl)butyrate), Sulfo SIAB (N-sulfosuccinimidyl(4-iodoacetyl)aminobenzoate), Sulfo SMCC (sulfosuccinimidyl 4-(N-maleimidomethyl)cyclohexane-1-carboxylate), Sulfo SMPB (sulfosuccinimidyl 4-(rhomaleimidophenyl) butyrate), and MAL-PEG-NHS (maleimide PEG N-hydroxysuccinimide ester); sulfhydryl/hydroxyl linkers such as PMPI (N-rho-maleimidophenyl) isocyanate; sulfhydryl/carbohydrate linkers such as EMCH (N-(epsilon-maleimidocaproic acid) hydrazide); and amine/carboxyl linkers such as EDC (1-ethyl-3-(3-dimethylaminopropyl) carbodiimide hydrochloride).

In some aspects, the one or more reactive components can be linked to a solid substrate through non-covalent interactions. Examples of non-covalent interactions include, but are not limited to, protein-protein interactions such as those between avidin/streptavidin and biotin, protein A and immunoglobulins, protein G and immunoglobulins, or secondary antibodies with primary antibodies. For example, the one or more reactive components may be modified with biotin using standard methods and bound to a solid substrate derivatized with streptavidin. Alternatively, one or more reactive components may be modified with streptavidin and bound to a solid substrate derivatized with biotin. A single chain antibody may incorporate streptavidin as part of a fusion protein. See, e.g., Koo, et al. *Appl. Environ. Microbiol.* 64:2497-2502, 1998) to facilitate attachment of the antibody to the solid substrate via a biotin-streptavidin linkage. Solid substrates such as beads or other particulate substrates derivatized with protein A, protein G, streptavidin, avidin, biotin, secondary antibodies are available from commercial sources (from, e.g., Pierce-Thermo Scientific, Rockford, Ill., Sigma-Aldrich, St. Louis, Mo.). In some aspects, the one or more reactive components may bind to the solid substrate through a non-covalent interaction and be further cross-linked to the solid substrate using a cross-linking agent.

In an aspect, the one or more reactive components can be associated with a solid substrate that are cells, e.g., mammalian cells, enucleated erythrocytes, bacteria, or viral particles, or vesicles such as liposomes or other micellular vesicles. Cells and vesicles may be modified with one or more reactive components using many of the same methods as provided herein. One or more reactive components may be bound to cells or vesicles using one or more homobifunctional or heterofunctional cross-linkers through primary amines and carboxyl groups. Alternatively, cells may be modified with one or more reactive components using a biotin-streptavidin bridge. For example, one or more reactive components may be biotinylated and linked to a non-specifically biotinylated cell surface through a streptavidin bridge. An antibody, aptamer, or receptor may be biotinylated using standard procedures. The surface membrane proteins of a cell may be biotinylated using an amine reactive biotinylation reagent such as, for example, EZ-Link Sulfo-NHS-SS-Biotin (sulfo-succinimidyl 2-(biotinamido)-ethyl-1,3-dithiopropionate; Pierce-Thermo Scientific, Rockford, Ill., USA; see, e.g., Jaiswal, et al. Nature Biotech. 21:47-51, 2003; U.S. Pat. No. 6,946,127).

In an aspect, the one or more reactive components can be associated with lipid or micellular vesicles. In some aspects, the one or more reactive components can be antibodies attached to a liposome. Antibodies may be added to liposomes using cross-linking agents and protein A. See, e.g., Renneisen, et al., J. Bio. Chem., 265:16337-16342, 1990, which is incorporated herein by reference. The liposomes are formed from dry lipid in the presence of an aqueous solution, e.g., a buffer of appropriate pH followed by extrusion through a high pressure device fitted with a polycarbonate filter with the desired pore size to form liposomes of a specific size range. The liposomes are modified with N-succinimidyl 3-(2-pyridyldithio) propionate-modified protein A. The one or more antibodies are linked to the liposomes through selective binding to the protein A. Alternatively, thiolated antibodies may be covalently linked to liposomes prepared with 4-(p-maleimidophenyl) butyrylphosphatidyl-ethanolamine. See, e.g., Heath, et al., PNAS 80:1377-1381, 1983, which is incorporated herein by reference.

In an aspect, the one or more reactive components can be one or more multispecific antibody complex with one or more components that recognize an antigen on the surface of a cell or vesicle and a second one or more components that recognize one or more inflammatory mediators. For example, a multispecific antibody complex may have one component that binds to erythrocytes and a second component that binds one or more inflammatory mediators. A number of examples of multispecific antibodies that recognize erythrocytes and various endogenous targets or pathogens are provided. See, e.g., U.S. Pat. Nos. 5,470,570 and 5,843,440; U.S. Pat. App. Nos. 2003/0215454 A1 and 2006/0018912 A1.

In some aspects, the one or more reactive components can be expressed on the surface of a cell. The one or more reactive components may be naturally expressed on the surface of a cell, such as a receptor of a specific inflammatory mediator on a specific cell type. Alternatively, the one or more reactive components may be expressed on the surface of a cell using genetic manipulation. For example, cells may be genetically manipulated to express a receptor that binds one or more inflammatory mediators. In one example, the genetic expression of a receptor on the surface of Chinese hamster ovary (CHO) cells is capable of binding the cytokine interleukin 1 (IL-1). See, e.g., Curtis, et al., PNAS USA 86:3045-3049, 1989, which is incorporated herein by reference. Alternatively, cells may be genetically manipulated to express one or more specific antibodies on the cell surface. Methods have been provided for cell surface expression of single chain Fv antibody fragments (scFv) fused to membrane-associated proteins. See, e.g., Ho, et al., Proc. Natl. Acad. Sci. USA 103:9637-9642, 2006; Francisco, et al., Proc. Natl. Acad. Sci. USA 90:10444-10448, 1993; U.S. Pat. Appl. No. 2006/0083716, which are incorporated herein by reference. In this aspect, the cDNA sequence encoding all or part of an inflammatory mediator-specific antibody is fused in an expression construct in frame with a membrane-associated protein and expressed in an appropriate cell type.

EXEMPLARY ASPECTS

Example 1

Intracorporeal Device for Sensing, Binding and Altering Inflammatory Mediators

A method for treating an inflammatory condition or disease is provided and includes an intracorporeal device designed to sense one or more inflammatory mediators in peripheral blood of a subject and a modulating means configured to bind the one or more inflammatory mediators and alter the functional structure or activity of the one or more inflammatory mediators to achieve a desired target value. The intracorporeal device includes a controller in communication with the sensor and configured to adjust the modulating means to achieve the target value of the detected one or more inflammatory mediators in the peripheral blood of the subject. The device optionally includes a receiver for receiving and processing data regarding the sensed levels of one or more inflammatory mediators and a transmitter for transmitting data regarding the sensed levels of one or more inflammatory mediators to an external controller.

The intracorporeal device is placed in or proximal to one or more blood vessels of a subject. In this example, the intracorporeal device is a hollow stent-like structure that is placed into a vessel at or near the site of inflammation using a catheter guide wire. The components of the intracorporeal device including sensors, controller, binding elements, and reactive components are affixed to and/or incorporated into one or both surfaces of the stent-like structure. The intracorporeal device is configured such that blood in the vessel is allowed to flow through it essentially unobstructed.

The intracorporeal device includes one or more sensors that sense the levels of one or more inflammatory mediators in the peripheral blood of a subject. In this example, the one or more sensors are piezoelectric sensors in which aptamers directed against the proinflammatory mediators TNF-α and IL-1 are used as recognition elements. The interaction of TNF-α and IL-1 with their respective recognition elements triggers the piezoelectric sensor to send a signal to the controller. In this example, the controller is an integral component of the intracorporeal device. The controller calculates the levels of TNF-α and/or IL-1 in the peripheral blood based on the input from the sensors and compares these data with target values, e.g., desired concentrations of TNF-α and/or IL-1. In some instances, the target value for TNF-α and/or IL-1 is that observed in a normal subject not experiencing an inflammatory disease or a disease resulting in an inflammatory response. In other instances, the target value for TNF-α and/or IL-1 may represent a reduction of at least 20%, at least 40%, at least 60%, at least 80%, or at least 100% relative to the current level of TNF-α and/or IL-1 in the peripheral blood of the subject. The controller may optionally send a wireless signal to an external controller to alert the subject and/or one or more caregivers as to the levels of TNF-α and/or IL-1 in the peripheral blood of the subject.

The intracorporeal device further includes one or more binding agents for capturing one or more inflammatory mediators within the treatment chamber of the intracorporeal device. In this example, the binding agents are antibodies directed against the proinflammatory mediators TNF-α and IL-1. Antibodies to TNF-α, IL-1, and many other inflammatory mediators are available from commercial sources (from, e.g., Novus Biological, Littleton, Colo.; Sigma-Aldrich, St. Louis, Mo.; United States Biological, Swampscott, Mass.) or are readily generated using standard methods. The antibodies directed against TNF-α and IL-1 are preferably incorporated within the stent-like structure of the intracorporeal device at one or more sites to maximize exposure to TNF-α and IL-1 in the blood of a subject. Protocols are provided for chemically linking an antibody to a collagen-coated stent using N-succinimidyl-3-(2-pyridyldithiol)-propionate as a cross-linker. See, e.g., Jin, et al., *J. Gene Med.* 8:786-793, 2008, which is incorporated herein by reference.

The intracorporeal device further includes one or more reactive components designed to alter the functional structure of one or more inflammatory mediators and as such modulate their physiological effects to achieve the desired target values. In some aspects, the reactive component can be the one or more specific binding agents capable of directly altering the functional structure of the one or more inflammatory mediators. In this example, the binding agent antibodies directed against TNF-α and IL-1 have intrinsic catalytic activity triggered by a controllable energy source. In response to ultraviolet energy released by the intracorporeal device within the treatment chamber, the TNF-α and IL-1 binding agent antibodies produce reactive oxygen species that alter the functional structure of TNF-α and IL-1. The release of ultraviolet energy in the treatment chamber is triggered by the controller based on the sensed levels of TNF-α and IL-1 in the peripheral blood. In the absence of a triggering event, the TNF-α and IL-1 bound to the binding agent antibodies will eventually dissociate in an intact and active form and return to the peripheral blood of the subject.

Example 2

Intracorporeal Device for Sensing and Altering Inflammatory Mediators

A method for treating an inflammatory condition or disease is provided and includes an intracorporeal device designed to sense one or more inflammatory mediators in the peripheral blood of a subject and a modulating means to alter the activity of the one or more inflammatory mediators to achieve a desired target value. The intracorporeal device is placed in or proximal to one or more blood vessels and includes a treatment chamber configured to receive at least a portion of the peripheral blood through a flow route, the controller configured to control flow of peripheral blood through the flow route into the treatment chamber. The treatment chamber includes one or more reactive components utilizing a set of differing energy inputs specifically directed to the one or more inflammatory mediators within a treatment chamber of the device and configured to alter a functional structure of the one or more inflammatory mediators in the peripheral blood. The device optionally includes a transmitter configured to transmit the sensed levels of one or more inflammatory mediators to an external controller.

The intracorporeal device includes one or more sensors that sense the levels of one or more inflammatory mediators in the peripheral blood of a subject. In this example, the one or more sensors are aptamer-based molecular beacons designed to fluoresce in response to selectively binding one or more inflammatory mediators. The aptamer-based molecular beacons include a recognition element and at least one fluorescing moiety and at least one quenching moiety. The recognition element selectively interacts with one or more proinflammatory mediators, e.g., TNF-α and IL-1 and one or more anti-inflammatory mediators, e.g., IL-10. Fluorescence induced by electromagnetic energy emitted by the intracorporeal device is quenched in the absence of TNF-α, IL-1, or IL-10. The binding of TNF-α, IL-1, and/or IL-10 to the respective selective aptamer induces a conformational change in the aptamer and increases the distance between the fluorescing moiety and the quenching moiety resulting in a fluorescent signal in response to electromagnetic energy. The level of fluorescent signal is proportional to the level of TNF-α, IL-1, and/or IL-10 in the blood sample. The emitted fluorescence is captured by a CCD or CMOS detector and a corresponding signal is sent to the controller.

The controller calculates the levels of TNF-α, IL-1, and/or IL-10 in the peripheral blood based on the input from the sensors and compares these data with target values, e.g., desired concentrations of TNF-α, IL-1, and/or IL-10. In some instances, the target value can represent a ratio of concentrations for the proinflammatory mediators TNF-α and IL-1 relative to the anti-inflammatory mediator IL-10. The controller may optionally send a wireless signal to an external controller to alert the subject and/or one or more caregivers as to the levels of TNF-α, IL-1, and/or IL-10 in the peripheral blood of the subject.

The controller optionally controls flow of the peripheral blood into the treatment chamber. The controller initiates release of one or more sets of differing energy inputs into the treatment chamber of the intracorporeal device to specifically alter a functional structure of one or more inflammatory mediators, e.g., TNF-α, IL-1, and/or IL-10. In this example, the set of differing energy inputs selectively resonates a plurality of resonant structures in TNF-α, IL-1, and/or IL-10. The resonance can alter the functional structure of TNF-α, IL-1, and/or IL-10 by transferring substantially more energy to at least a portion of the group of proximate atoms than to other atoms in the medium, breaking a predetermined bond between two members of the group of proximate atoms, and/or changing a kinetic parameter of a reaction involving a member of the group of proximate atoms. The sets of differing energy inputs are transmitted in a simultaneous, sequential, and/or in a temporally overlapping pattern that specifically disrupts one inflammatory mediator relative to another in the treatment chamber. The energy inputs are electromagnetic energy emitted at one or more wavelengths from miniaturized diode lasers associated with the intracorporeal device. Treatment continues until the target values for the one or more inflammatory mediators have been achieved.

Example 3

Intracorporeal Device for Sensing Inflammatory Mediators and Controllably Releasing Inflammatory Modulators A method for treating an inflammatory condition or disease is provided including an intracorporeal device designed to sense one or more inflammatory mediators in the peripheral blood of a subject and a reservoir to controllably release one or more reactive components, e.g., one or more inflammatory modulators, in the peripheral blood. The one or more inflammatory modulators are configured to alter a functional structure of the one or more inflammatory mediators to achieve a desired target value of the one or more inflammatory mediators in the peripheral blood. The intracorporeal device is placed in or proximal to one or more blood vessels of a subject and includes one or more sensors for sensing one or more inflammatory mediators, a controller to receive data regarding the sensed levels of one or more inflammatory mediators, one or more reservoirs containing one or more inflammatory modulators controllably opened or closed by the controller.

The device may optionally a transmitter configured to transmit the sensed levels of the one or more inflammatory mediators to an external controller.

The intracorporeal device can be a stent-like structure that resides in a fixed position in a blood vessel. Alternatively, the intracorporeal device can be free to travel in the lumen of one or more blood vessels. See, e.g., U.S. Patent Application 2007/0156211 A1, which is incorporated herein by reference.

The intracorporeal device includes one or more sensors for sensing the levels of one or more inflammatory mediators in the peripheral blood of a subject. The sensors include one or more recognition elements designed to sense levels of one or more inflammatory mediators. In this example, the recognition elements associated with the sensors are antibodies directed towards the proinflammatory mediators TNF-α and IL-1 and the anti-inflammatory mediator IL-10. As blood passes by the intracorporeal device, the sensors associated with the device respond to the presence of TNF-α, IL-1 and/or IL-10 by sending an electrical signal to a controller. In this example, the controller is an integral component of the intracorporeal device. The controller compares the data regarding the sensed level of TNF-α, IL-1 and/or IL-10 in the peripheral blood of a subject with target values, e.g., a desired range of concentrations of the proinflammatory or anti-inflammatory mediators. In some instances, the target value can represent a ratio of concentrations, for example, the concentration of proinflammatory mediators TNF-α and IL-1 relative to the concentration of the anti-inflammatory mediator IL-10. As appropriate, the controller signals release of one or more inflammatory modulators from reservoirs associated with the intracorporeal device to achieve the target values.

The intracorporeal device includes one or more micro-reservoirs containing the one or more inflammatory modulators. The micro-reservoirs may be covered by a seal that is disrupted in response to an electrical signal from the controller. See, e.g., U.S. Pat. No. 7,413,846; Maloney & Santini, Proceedings 26$^{th}$ Annual International Conference IEEE EMBS, San Francisco, Calif., USA, Sep. 1-5, 2004, which are incorporated herein by reference. The inflammatory modulators in the micro-reservoirs may directly or indirectly modulate the level of one or more inflammatory mediators. In this example, the inflammatory modulators directly alter the functional levels of TNF-α, IL-1 and/or IL-10 and are contained in separate reservoirs within the intracorporeal device. One set of reservoirs contains a soluble TNF-α receptor, e.g., etanercept. A second set of reservoirs contains an IL-1 receptor antagonist, e.g., anakinra. The third set of reservoirs contains recombinant IL-10. Release of the inflammatory modulators from the one or more reservoirs is controlled by signals sent from the controller and is based on the sensed level of TNF-α, IL-1 and/or IL-10 in the peripheral blood. In this configuration, the levels of the proinflammatory mediators TNF-α and IL-1 may be controllably decreased and the levels of the anti-inflammatory mediator IL-10 may be controllably increased to achieve appropriate target values of each inflammatory mediator.

Example 4

Intracorporeal Device for Sensing Inflammatory Mediators and Automatically Releasing Inflammatory Modulators A method for treating an inflammatory condition or disease is provided and includes an intracorporeal device designed to sense one or more inflammatory mediators in the peripheral blood of a subject and to automatically release one or more reactive components, e.g., one or more inflammatory modulators, in response to the sensed condition to achieve a desired target value of the one or more inflammatory mediators. The intracorporeal device is placed in or proximal to one or more blood vessels of a subject and includes one or more sensors for sensing one or more inflammatory mediators, one or more reservoirs directly linked to the sensors for immediate and automatic release of one or more inflammatory modulators, and optionally a transmitter for transmitting the sensed levels of one or more inflammatory mediators to an external controller. Data regarding the level of one or more inflammatory mediators in the peripheral blood of a subject is optionally transmitted to an external controller for monitoring by the subject and/or one or more caregivers.

The intracorporeal device includes one or more sensors directly linked to release of one or more inflammatory modulators in response to sensing one or more inflammatory mediators. For example, the one or more sensors may be associated with target responsive vesicles that release the vesicle contents in response to binding one or more inflammatory mediators. In this example, the one or more sensors include recognition elements that interact with proinflammatory mediators, e.g., TNF-α, IL-1, IL-6, and IL-8. The recognition elements are aptamers that bind TNF-α, IL-1, IL-6, and/or IL-8 and are also involved in encapsulating one or more inflammatory modulators into target responsive vesicles. For example, two distinct aptamers capable of partial overlapping hybridization are copolymerized into a polyacrylamide-based hydrogel. One of the two aptamers is a recognition element that binds to a proinflammatory mediator, e.g., IL-1. The interaction of IL-1 with the aptamer recognition element causes the two partially overlapping aptamers to separate from one another and to change the properties of the hydrogel, resulting in release of the contents of the hydrogel. The hydrogel is loaded with one or more inflammatory modulator, e.g., an IL-1 receptor antagonist. In this aspect, an increase in IL-1 in the peripheral blood of a subject leads to increased binding to the aptamer/hydrogel complex, separation of the aptamer pair, and increased release of the IL-1 receptor antagonist. The target-responsive vesicles are retained in one or more compartments of the intracorporeal device. The compartments include a membrane or screen through which inflammatory mediators and inflammatory modulators may diffuse but otherwise prevents the release of the target-responsive vesicles into the peripheral circulation.

The interaction of one or more inflammatory mediators with the target responsive vesicles can be monitored using fluorescence resonance energy transfer (FRET). For example, the two overlapping aptamers incorporated into the hydrogel can be modified with a fluorescence emitting molecule, e.g., AF 647 (Molecular Probes—Invitrogen, Carlsbad, Calif.) and a fluorescence quenching molecule, e.g., QSY 21 (Molecular Probes—Invitrogen, Carlsbad, Calif.). In the absence of binding a proinflammatory mediator, e.g., IL-1, the two aptamers remain linked to one another, fluorescence associated with the aptamers remains quenched and the inflammatory modulator remains encapsulated in the hydrogel. Upon binding IL-1, the aptamers change configuration relative to one another separating the fluorescence emitting molecule and the quenching molecule resulting in a measurable fluorescent signal. The fluorescent signal is measured by a CCD device or other light capture device within the intracorporeal device and transmitted wirelessly to an external controller. Alternatively, the fluorescent signal is measured through the skin using near infrared imaging and fluorescent dyes or quantum dots that fluoresce in the near infrared wavelengths. See, e.g., Frangioni *Curr. Opin. Chem. Biol.* 7:626-

634, 2003, which is incorporated herein by reference. An example of a near infrared dye FRET pair would be IRDye 800CW and IRDye QC-1 Quencher (LI-COR, Lincoln, Nebr.).

Example 5

Extracorporeal Device for Sensing and Sequestering Inflammatory Mediators

A method for treating an inflammatory disease is provided and includes an extracorporeal device configured to sense and sequester one or more inflammatory mediators in the peripheral blood of a subject to achieve a desired target value. The extracorporeal device includes a flow route for extracting blood from a subject, a component for optionally fractionating the whole blood into separate components, one or more sensors for sensing the levels of one or more inflammatory mediators, a controller to receive data regarding the sensed levels of one or more inflammatory mediators, one or more binding elements incorporated into one or more treatment chambers to sequester one or more inflammatory mediators, and a flow route for returning the processed blood to the subject.

Blood is withdrawn from a subject through a catheter inserted into a vein or artery of the subject. The catheter is further attached to one or more conduits that flow into the extracorporeal device. The whole blood is fractionated by centrifugation and/or filtration within the extracorporeal blood processing device to isolate the plasma. Alternatively, whole blood from a subject is fractionated using commercially available apheresis instrumentation (from, e.g., CardianBCT, CO, USA; Baxter, Ill., USA) and the resulting plasma is sent from the apheresis instrument to the extracorporeal device for further processing.

The whole blood or plasma is passed over one or more sensors associated with the extracorporeal device. The one or more sensors are configured to sense one or more inflammatory mediators and include one or more recognition elements. In this example, the recognition elements are antibodies configured to selectively recognize the proinflammatory mediators, e.g., TNF-α, IL-1, IL-6, and IL-8. The recognition element antibodies are immobilized on one or more solid substrates, e.g., a CM5 sensor chip (Biacore, Inc.—GE Healthcare, Piscataway, N.J.), by crosslinking free amino acid groups associated with the antibodies to N-hydroxylsuccinimide carbodiimide-activated carboxyl groups associated with the sensor chip. The levels of TNF-α, IL-1, IL-6, and/or IL-8 in the whole blood or plasma are sensed via surface plasmon resonance. An example of instrumentation that uses surface plasmon resonance is the BIACORE system which includes a sensor microchip, a laser light source emitting polarized light, an automated fluid handling system, and a diode array position sensitive detector. See, e.g., Biacore, Inc.—GE Healthcare, Piscataway, N.J.; and Raghavan & Bjorkman *Structure* 3:331-333, 1995, which are incorporated herein by reference.

Data regarding the levels of TNF-α, IL-1, IL-6, and/or IL-8 are transmitted to a controller associated with the extracorporeal device. The controller compares the current levels of TNF-α, IL-1, IL-6, and/or IL-8 with one or more target values, e.g., desired concentrations of TNF-α, IL-1, IL-6, and/or IL-8. As appropriate, the controller diverts all or part of the whole blood or plasma to one or more treatment chambers in the extracorporeal device to treat the blood to achieve a target value of the one or more inflammatory mediators. Diversion of blood into one or more treatment chambers of the extracorporeal device continues until the target value of the one or more inflammatory mediators has been achieved.

The one or more treatment chambers include one or more binding agents configured to bind and sequester one or more inflammatory mediators. In this example, the binding agents are polymer based, artificial binding substrates formed by molecular imprinting and are designed to selectively bind and sequester TNF-α, IL-1, IL-6, and/or IL-8 within the one or more treatment chambers. In one configuration, all or part of the whole blood or plasma passes through a single treatment chamber that includes binding agents directed towards multiple inflammatory mediators. In an alternative configuration, all or part of the whole blood or plasma passes through multiple treatment chambers, each configured with a binding agent directed to one specific inflammatory mediator. For example, all or part of the whole blood may pass sequentially through a series of treatment chambers configured to selectively bind and sequester TNF-α, IL-1, IL-6, or IL-8, respectively, to achieve a target value for each of these inflammatory mediators. The treated blood is returned to the peripheral circulation of the subject through a conduit leaving the extracorporeal device.

Example 6

Extracorporeal Device for Sensing, Binding and Altering Inflammatory Mediators

A method for treating an inflammatory condition or disease is provided and includes an extracorporeal device configured to sense one or more inflammatory mediators, and to bind and alter the functional structure of the one or more inflammatory mediators in the peripheral blood of a subject to achieve a desired target value. The extracorporeal device includes a flow route for extracting blood from a subject, a component for optionally fractionating the whole blood into separate components, one or more sensors for sensing the levels of one or more inflammatory mediators, a controller to receive data regarding the sensed levels of one or more inflammatory mediators, one or more binding elements incorporated into one or more treatment chambers, one or more reactive components designed to alter the functional structure of one or more inflammatory mediators, and a flow route for returning the processed blood to the subject.

Blood is removed from a subject through a catheter inserted into the subject. The catheter is further attached to one or more conduits that flow into the extracorporeal device. The whole blood is fractionated by centrifugation and/or filtration within the extracorporeal blood processing device to isolate plasma. The plasma containing inflammatory mediators but free of blood cells is optionally further fractionated using one or more semi-permeable membranes to isolate a plasma fraction enriched in blood components ranging in molecular weight from about 1,000 to about 150,000 dalton.

The fractionated plasma is passed over one or more sensors associated with the extracorporeal device. The one or more sensors include one or more recognition elements and are configured to sense one or more inflammatory mediators. In this example, the recognition elements linked to the one or more sensors are antibodies configured to selectively recognize the proinflammatory mediators TNF-α, IL-1, IL-6, and IL-8. The levels of TNF-α, IL-1, IL-6, and/or IL-8 in the plasma are sensed, and the data are transmitted to a controller associated with the extracorporeal device. The controller compares the current levels of TNF-α, IL-1, IL-6, and/or IL-8 with one or more target values, e.g., desired concentrations of TNF-α, IL-1, IL-6, and/or IL-8. As appropriate, the controller diverts all or part of the fractionated plasma to one or more treatment chambers in the extracorporeal device to treat the blood to achieve a target value of the one or more inflammatory mediators.

The one or more treatment chambers include one or more binding elements that capture and retain one or more inflammatory mediators in the treatment chamber. In this example, the binding agents are oligonucleotide-based DNA aptamers directed towards binding the inflammatory mediators TNF-α, IL-1, IL-6, and IL-8. The aptamers directed towards TNF-α, IL-1, IL-6, and IL-8 are attached to beads using one or more of the crosslinking methods described herein. The aptamer-modified beads are retained within the treatment chamber of the extracorporeal device via size exclusion using a membrane or screen that is otherwise permeable to blood components. The pro-inflammatory mediators TNF-α, IL-1, IL-6, and IL-8 in the plasma bind to the aptamer-modified beads and are retained in the treatment chamber. Non-bound components of the plasma flow out of the treatment chamber and are returned to the peripheral blood of the subject.

Altering the functional structure of TNF-α, IL-1, IL-6, and/or IL-8 occurs in the treatment chamber by denaturation and/or degradation of the pro-inflammatory mediators using one or more proteases configured to cleave one or more peptide bonds of the bound TNF, IL-1, IL-6 and/or IL-8. The treatment chamber is isolated from the peripheral blood flow of the subject and flooded with the one or more proteases to digest the peptide bonds of the one or more inflammatory mediators. Following protease treatment, the treatment chamber may be washed with an appropriate physiological solution, e.g. 0.9% saline solution, prior to receiving more plasma for processing.

The fractionated plasma in which the one or more inflammatory mediators has been altered or destroyed is combined with other components of the whole blood and may be returned to the subject.

Example 7

Extracorporeal Device for Sensing Inflammatory Mediators and Controllably Releasing Inflammatory Modulators A method for treating an inflammatory condition or disease is provided and includes an extracorporeal device designed to sense one or more inflammatory mediators in the peripheral blood of a subject and to controllably release one or more inflammatory modulators to achieve a desired target value of the one or more inflammatory mediators. The extracorporeal device includes one or more sensors for sensing one or more inflammatory mediators, a controller to receive data regarding the sensed levels of the one or more inflammatory mediators, one or more reservoirs containing one or more inflammatory mediators controllably opened or closed by the controller, and optionally a transmitter for wirelessly transmitting the sensed levels of one or more inflammatory mediators to the subject and/or one or more caregivers.

Blood is removed from a subject through a catheter inserted into the subject. The catheter is further attached to one or more conduits that flow into the extracorporeal device. All or part of the flow of whole blood, plasma, or fractionated plasma, may be analyzed for the level of one or more inflammatory mediators. In some aspects, the extracorporeal device includes a component for separating a small sample of blood from the bulk blood flow. The small stream of blood passes through a compartment of the device that includes one or more sensors for sensing the level of one or more inflammatory mediators. The level of one or more inflammatory mediators in a small sample of blood flow is believed to be representative of the level of one or more inflammatory mediators in the blood as a whole.

The one or more sensors associated with the device may use any of a number of methodologies including surface plasmon resonance, piezoelectric, and/or molecular beacons as described herein. In one configuration, the one or more sensors are an array of sensor chips capable of detecting multiple inflammatory mediators simultaneously. The sensor chips include recognition elements that interact with any of a number of proinflammatory mediators, e.g., TNF-α, IL-1, IL-6, IL-8, IL-12 and any of a number of anti-inflammatory mediators, e.g., IL-4, IL-10, IL-13 and TGFβ. In this example, the recognition elements are antibodies selective for a given inflammatory mediator, but could also include aptamers, receptors, ligands or any other biomolecule that binds to an inflammatory mediator. As peripheral blood from the subject passes over the sensor surface, inflammatory mediators present in the blood interact with the cognate recognition elements on the sensor chips, causing a signal to be transmitted to the controller. The controller compares the data regarding the current levels of one or more inflammatory mediators in the peripheral blood of a subject with target values, e.g., desired concentrations for the one or more inflammatory mediators. As appropriate, the controller signals release of one or more reactive components, e.g., one or more inflammatory modulators, from one or more reservoirs associated with the extracorporeal device to achieve the target values. Alternatively, the controller may transmit a message to the subject and/or a third party individual regarding the level of one or more inflammatory mediators and the assessment of which reactive components or modulators, if any, should be released into the peripheral blood of the subject to modulate an inflammatory response. In response, the subject and/or a third party individual may choose to administer one or more modulators into the peripheral blood of the subject.

The intracorporeal device includes one or more reservoirs containing one or more inflammatory modulators. In this example, the inflammatory modulators alter the functional levels of any of a number of proinflammatory mediators, e.g., TNF-α, IL-1, IL-6, IL-8, IL-12 and any of a number of anti-inflammatory mediators, e.g., IL-4, IL-10, IL-13 and TGF-β and are contained in separate reservoirs within the extracorporeal device. For example, one set of reservoirs contains a soluble TNF-α receptor, e.g., etanercept; a second set of reservoirs contains an IL-1 receptor antagonist, e.g., anakinra; a third set of reservoirs contains recombinant IL-10; and a fourth set of reservoirs contains recombinant TGF-β. Release of the inflammatory modulators from the one or more reservoirs is controlled by signals sent from the controller and is based on the sensed levels of TNF-α, IL-1, IL-10 and/or TGF-β in the peripheral blood. In this configuration, the levels of the proinflammatory mediators TNF-α and IL-1 may be controllably decreased and the levels of the anti-inflammatory mediator IL-10 and TGF-β may be controllably increased to achieve appropriate target values of each inflammatory mediator.

Example 8

Combined Intracorporeal and Extracorporeal Device for Sensing, Binding and Inactivating Inflammatory Mediators A method for treating an inflammatory condition or disease is provided and includes a device having combined intracorporeal and extracorporeal components to sense one or more inflammatory mediators, and to bind and alter the one or more inflammatory mediators in the peripheral blood of a subject to achieve a target value. The device includes one or more intracorporeal components to sense the level one or more inflammatory mediators in the peripheral blood, a controller to receive data regarding the sensed levels of the one or more inflammatory mediators, an extracorporeal component to withdraw the peripheral blood, one or more reactive components to alter the functional structure of the one or more inflammatory mediators, and a transmitter for wirelessly transmitting the sensed levels of one or more inflammatory mediators to the subject and/or one or more caregivers.

The one or more intracorporeal components of the device are placed in or proximal to one or more blood vessels of a subject. The intracorporeal component of the device may be a stent-like structure that resides in a fixed position in a blood vessel. Alternatively, the intracorporeal component of the device may be free to travel in the lumen of one or more blood vessels. See, e.g., U.S. Patent Application 2007/0156211 A1, which is incorporated herein by reference.

The one or more intracorporeal components of the device include one or more sensors for sensing the level of the one or more inflammatory mediators in the peripheral blood of a subject. The sensors can be any of a number of sensor types as described herein. The one or more sensors include one or more recognition elements that interact with one or more inflammatory mediators as described herein. The sensed data are transmitted wirelessly to a controller associated with the extracorporeal component of the device.

The controller receives the data regarding the level of one or more inflammatory mediators in the peripheral blood of a subject. The controller compares the current levels of one or more inflammatory mediators with a target value, e.g., a desired concentration or concentration range for one or more inflammatory mediators. Based on the comparison between the current levels and the target value, the controller automatically initiates extracorporeal treatment of the blood to achieve the appropriate target values of the one or more inflammatory mediators to control an inflammatory response in a subject. In this example, the subject is constantly connected to the extracorporeal component of the device via a flow route or conduit and the controller is able to automatically initiate withdrawal of blood from the subject and into the extracorporeal treatment chamber. Alternatively, the controller sends data regarding the current levels of one or more inflammatory mediators and the desired target values to the subject and/or a caregiver. The subject and/or caregiver may choose to initiate extracorporeal treatment of the blood based on the information provided by the controller.

The extracorporeal component of the device releases or activates any of a number of reactive components designed to alter the functional structure of one or more inflammatory mediators as described herein. The reactive component may be non-selective, e.g., a filtering system that non-selectively captures and sequesters one or more inflammatory mediators. Alternatively, the reactive component may be binding agents such as antibodies or aptamers that bind specific inflammatory mediators, e.g., TNF-α and IL-1 and retain them in the treatment chamber. Other reactive components, e.g., one or more of a denaturing agent, a degradative agent, an enzyme, a chemical, an energy source, a modulator, or a combination thereof may be used to alter the functional structure of the inflammatory mediators retained in the treatment chamber. The treated blood having attained a target level of the one or more inflammatory mediators is returned to the peripheral circulation of the subject through a conduit leaving the extracorporeal device.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An extracorporeal device comprising:
    a treatment chamber including at least one flow route configured to receive and return peripheral blood of a subject;
    at least one sensor configured to detect one or more inflammatory mediators in the peripheral blood of the subject;
    at least one reservoir containing one or more reactive biological or chemical compounds that alter a functional structure of the one or more inflammatory mediators; and
    a controller in communication with the at least one sensor and the at least one reservoir and configured to modulate release of the one or more reactive biological or chemical compounds from the at least one reservoir and into the peripheral blood to substantially attain a target value of the detected one or more inflammatory mediators in the peripheral blood of the subject.

2. The device of claim 1, wherein the one or more reactive biological or chemical compounds includes a denaturing agent, a degradative agent or a binding agent.

3. The device of claim 2, wherein the one or more reactive biological or chemical compounds decreases an activity of one or more of anaphylatoxins, cytokines, chemokines, leukotrienes, prostaglandins, complement, coagulation factors, or proinflammatory cytokines.

4. The device of claim 2, wherein the denaturing agent includes an acid, base, solvent, cross-linking agent, chaotropic agent, disulfide bond reducer, enzyme, drug, cell, or radical ion.

5. The device of claim 2, wherein the degradative agent includes at least one of an enzyme, coenzyme, enzyme complex, catalytic antibody, proteasome, strong acid, strong base, radical, photoactivatable agent, drug, cell, or radical ion.

6. The device of claim 5, wherein the catalytic antibody generates the radical ion.

7. The device of claim 2, wherein the one or more binding agents on a matrix adapted to the treatment chamber are configured to sequester at least one of the one or more inflammatory mediators from the blood.

8. The device of claim 2, wherein the one or more binding agents include one or more of antibodies, receptors, or cognates and binds to at least one of the one or more inflammatory mediators.

9. The device of claim 2, wherein the one or more binding agents include one or more of lectin, binding protein, catalytic antibody, catalytic aptamer, protease conjugate, or photoactivatable agent conjugate.

10. The device of claim 1, wherein the one or more reactive biological or chemical compounds decreases an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

11. The device of claim 1, wherein the one or more reactive biological or chemical compounds modulates an activity of an intermediate that modulates an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

12. The device of claim 11, wherein the one or more reactive biological or chemical compounds increases an activity of an intermediate that decreases an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

13. The device of claim 11, wherein the one or more reactive biological or chemical compounds decreases an activity of an intermediate that decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

14. The device of claim 1, wherein the target value includes a desired concentration of the one or more inflammatory mediators in the peripheral blood.

15. The device of claim 1, wherein the target value includes a desired range of concentrations of the one or more inflammatory mediators in the peripheral blood.

16. The device of claim 1, wherein the target value includes a desired ratio of concentrations of two or more inflammatory mediators in the peripheral blood.

17. The device of claim 1, wherein the target value includes a desired ratio of levels of two or more inflammatory mediators in the peripheral blood.

18. The device of claim 1, wherein the at least one sensor and the controller are configured to control levels of the one or more inflammatory mediators to achieve the target value.

19. The device of claim 1, wherein the controller is configured to control interaction between the one or more reactive components and the one or more inflammatory mediators in the treatment chamber.

20. The device of claim 1, wherein the controller is configured to control access to the treatment chamber by the peripheral blood.

21. The device of claim 1, wherein the at least one sensor includes a biosensor, chemical sensor, physical sensor, or optical sensor.

22. The device of claim 21, wherein the at least one sensor includes one or more of an aptamer, antibody, or receptor.

23. The device of claim 21, wherein the at least one sensor includes one or more of a recognition-based substrate, an aptamer-based substrate, an antibody-based substrate, surface plasmon resonance, genetically-modified cells, or genetically-modified cells with receptor-linked signaling.

24. The device of claim 23, wherein the genetically-modified cells include receptor-linked signaling by fluorogen-activating proteins.

25. The device of claim 1, wherein the at least one sensor is configured to detect cytokines, T-lymphocytes, B-lymphocytes, or antibodies.

26. The device of claim 1, wherein the at least one sensor is configured to detect body temperature, vital signs, edema, oxygen level, or pathogen/toxin level of the subject.

27. The device of claim 1, wherein the at least one sensor is configured to detect anaphylatoxins, chemokines, leukotrienes, prostaglandins, complement, coagulation factors, or proinflammatory cytokines.

28. The device of claim 27, wherein the at least one sensor is configured to detect TNF-α, IL-1, IL-1β, IL-6, IL-8, IL-10, IL-12, LPB, IFN-γ, LIF, MIF, MIP-1, MCP-1, C3-a, C5-a, exotoxins or endotoxins.

29. The device of claim 1, wherein the device includes a dialysis device, hemoperfusion device, apheresis device, intravenous device, or patch device.

30. The device of claim 1, wherein the at least one sensor includes at least one physical sensor.

31. The device of claim 30, wherein the at least one physical sensor includes at least one of a recognition-based substrate, an aptamer-based substrate, an antibody-based substrate, or surface plasmon resonance.

32. A system comprising:
an extracorporeal device including a treatment chamber configured to receive peripheral blood of a subject through a flow route, the treatment chamber including one or more reactive biological or chemical compounds that alter a functional structure of one or more inflammatory mediators in the peripheral blood of the subject; and
at least one sensor configured to detect the one or more inflammatory mediators in the peripheral blood and configured to provide an output related thereto; and
a controller configured to receive the output of the at least one sensor and configured to control interaction between the one or more biological or chemical compounds and the one or more inflammatory mediators in the treatment chamber by modulating release of the one or more reactive biological or chemical compounds into the treatment chamber;
wherein the at least one sensor and the controller function relative to a target value of at least one of the one or more inflammatory mediators in the peripheral blood.

33. The system of claim 32, wherein the one or more reactive biological or chemical compounds includes a denaturing agent, a degradative agent or a binding agent.

34. The system of claim 32, wherein the one or more reactive biological or chemical compounds decreases an activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

35. The system of claim 32, wherein the one or more reactive biological or chemical compounds increases an activity of an intermediate that decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

36. The system of claim 32, wherein the one or more reactive biological or chemical compounds decreases an activity of an intermediate that decreases the activity of one or more of TNF-α, IL-1, IL-1β, IL-6, IL-8, IL-10, IL-12, LPB, IFN-γ, LIF, MIF, MIP-1, MCP-1, C3-a, C5-a, exotoxin, or endotoxin.

37. The system of claim 33, wherein the one or more reactive biological or chemical compounds decreases an activity of one or more of anaphylatoxins, cytokines, chemokines, leukotrienes, prostaglandins, complement, coagulation factors, or proinflammatory cytokines.

38. An extracorporeal device comprising:
a treatment chamber configured to receive peripheral blood of a subject through a flow route;
at least one sensor configured to detect one or more inflammatory mediators in the peripheral blood of the subject;
at least one reservoir containing one or more modulators that alter a functional structure of the one or more inflammatory mediators; and
a controller in communication with the at least one sensor and the at least one reservoir and configured to adjust release of the one or more modulators from the at least one reservoir and into the peripheral blood to substantially attain a target value of the detected one or more inflammatory mediators in the peripheral blood of the subject.

* * * * *